(12) United States Patent
Brunner et al.

(10) Patent No.: US 7,557,109 B2
(45) Date of Patent: *Jul. 7, 2009

(54) TREATMENT FOR ATTENTION-DEFICIT HYPERACTIVITY DISORDER

(75) Inventors: Daniela Brunner, Riverdale, NY (US); Daniel W. Goodman, Riverside, CT (US)

(73) Assignee: Psychogenics, Inc., Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/219,416

(22) Filed: Sep. 2, 2005

(65) Prior Publication Data

US 2006/0004023 A1 Jan. 5, 2006

Related U.S. Application Data

(63) Continuation of application No. 10/199,634, filed on Jul. 19, 2002.

(60) Provisional application No. 60/306,825, filed on Jul. 20, 2001, provisional application No. 60/382,931, filed on May 23, 2002.

(51) Int. Cl.
*A61K 31/495* (2006.01)
*A61K 31/496* (2006.01)

(52) U.S. Cl. .............................. 514/255.03; 514/254.11

(58) Field of Classification Search ............. 514/224.2, 514/230.5, 253.05, 253.06, 254.09, 254.11, 514/253.03
See application file for complete search history.

(56) References Cited

U.S. PATENT DOCUMENTS

| | | | |
|---|---|---|---|
| 4,459,296 A | 7/1984 | Guerret et al. | |
| 4,772,604 A | 9/1988 | Van Wijngaarden et al. | |
| 4,782,061 A | 11/1988 | Hartog et al. | |
| 4,831,031 A | 5/1989 | Lowe | |
| 4,833,142 A | 5/1989 | Hartog et al. | |
| 4,874,770 A | 10/1989 | Van Wijngaarden et al. | |
| 4,889,852 A | 12/1989 | Hartog et al. | |
| 5,194,437 A | 3/1993 | Peglion et al. | |
| 5,424,313 A | 6/1995 | Hartog et al. | |
| 5,462,942 A | 10/1995 | Hartog et al. | |
| 5,463,050 A | 10/1995 | Ten Hoeve et al. | |
| 5,464,834 A | 11/1995 | Peglion et al. | |
| 5,576,318 A | 11/1996 | Turconi et al. | |
| 5,710,149 A | 1/1998 | Cliffe | |
| 5,741,789 A | 4/1998 | Hibschman et al. | |
| 5,846,982 A * | 12/1998 | Audia et al. ................ 514/318 |
| 5,914,263 A | 6/1999 | Buizer et al. | |
| 5,958,927 A | 9/1999 | Peglion et al. | |
| 5,968,954 A | 10/1999 | Peglion et al. | |
| 6,046,329 A | 4/2000 | Boer et al. | |
| 6,060,487 A | 5/2000 | Peglion et al. | |
| 6,090,812 A | 7/2000 | Feenstra et al. | |
| 6,114,334 A | 9/2000 | Kerrigan et al. | |
| 6,124,283 A | 9/2000 | Berg et al. | |
| 6,127,357 A | 10/2000 | Cliffe et al. | |
| 6,140,331 A | 10/2000 | Moltzen et al. | |
| 6,159,970 A | 12/2000 | Berg et al. | |
| 6,159,971 A | 12/2000 | Berg et al. | |
| 6,159,972 A | 12/2000 | Berg et al. | |
| 6,166,020 A | 12/2000 | Howard et al. | |
| 6,214,829 B1 | 4/2001 | Feenstra et al. | |
| 6,225,312 B1 | 5/2001 | Feenstra et al. | |
| 6,242,448 B1 | 6/2001 | Kelly et al. | |
| 6,245,766 B1 | 6/2001 | Watsky | |
| 6,251,908 B1 | 6/2001 | Bottcher et al. | |
| 6,306,859 B1 | 10/2001 | Childers et al. | |
| 6,310,066 B1 | 10/2001 | Kelly et al. | |
| 6,313,126 B1 | 11/2001 | Mewshaw et al. | |
| 6,376,494 B1 | 4/2002 | Childers et al. | |
| 6,387,904 B2 | 5/2002 | Howard | |
| 6,413,966 B1 | 7/2002 | Orjales et al. | |
| 6,465,482 B2 | 10/2002 | Mewshaw et al. | |
| 6,469,007 B2 | 10/2002 | Childers et al. | |
| 6,476,035 B1 | 11/2002 | Moltzen et al. | |
| 6,518,272 B2 | 2/2003 | Childers et al. | |
| 6,586,436 B2 | 7/2003 | Childers et al. | |
| 6,596,722 B2 | 7/2003 | Moltzen et al. | |
| 6,638,936 B1 | 10/2003 | Briner et al. | |
| 6,689,792 B2 | 2/2004 | Kelly et al. | |
| 6,713,626 B2 | 3/2004 | Feigelson et al. | |
| 6,727,263 B2 | 4/2004 | Moltzen et al. | |
| 6,784,294 B2 | 8/2004 | Chan et al. | |
| 6,828,325 B2 | 12/2004 | Feenstra et al. | |

(Continued)

FOREIGN PATENT DOCUMENTS

EP 138 280 B1 6/1988

(Continued)

OTHER PUBLICATIONS

Vries et al., Euro. J. Clin. Pharmacol. (1991) 41:485-488.*
Connor et al. Expert Opinion Ther. Patent (1998) 8(4):349-359.*
Quist et al., J. Am. Acad. Child Adolesc. Psychiatry, 40 (2) 253-257, Feb. 2001.*
Crime Times, "Linking Brain Dysfunction to Disordered/Criminal/Psychopathic Behavior," Crime Times, vol. 4, No. 2, pages 1 and 4, 1998.
American Psychiatric Association, "Attention-Deficit/Hyperactivity Disorder," *Diagnostic and Statistical Manual of Mental Disorders*, 4th Edition, pp. 85-93.
American Psychiatric Association, "Attention Deficit Disorders," *Diagnostic and Statistical Manual of Mental Disorders*, 3rd Edition, pp. 41-45.

(Continued)

*Primary Examiner*—Michael G Hartley
*Assistant Examiner*—Shirley V Gembeh
(74) *Attorney, Agent, or Firm*—King & Spalding LLP; Kenneth H. Sonnenfeld; Jonathan D. Ball

(57) ABSTRACT

A method for treating Attention Deficit/Hyperactivity Disorder (ADHD) in humans and the symptoms associated therewith, inattentiveness, and hyperactivity with impulsivity, using eltoprazine and related compounds is provided.

28 Claims, 16 Drawing Sheets

U.S. PATENT DOCUMENTS

| | | | |
|---|---|---|---|
| 6,867,284 | B1 | 3/2005 | Berger et al. |
| 6,911,448 | B2 | 6/2005 | Feenstra et al. |
| 6,930,110 | B2 | 8/2005 | Barkoczy et al. |
| 7,034,029 | B2 | 4/2006 | Kelly et al. |
| 2002/0013324 | A1 | 1/2002 | Childers et al. |
| 2002/0016334 | A1 | 2/2002 | Watsy et al. |
| 2003/0050306 | A1 | 3/2003 | Rhuland et al. |
| 2003/0162777 | A1 | 8/2003 | Leonardi et al. |
| 2003/0181446 | A1 | 9/2003 | Leonardi et al. |
| 2003/0186838 | A1 | 10/2003 | Van der Heijden et al. |
| 2003/0204087 | A1 | 10/2003 | Chan et al. |
| 2003/0208075 | A1 | 11/2003 | Jirkovsky et al. |
| 2004/0002500 | A1 | 1/2004 | Kramer et al. |
| 2004/0014768 | A1 | 1/2004 | Gottschlich et al. |
| 2004/0014972 | A1 | 1/2004 | Gottschlich et al. |
| 2004/0034219 | A1 | 2/2004 | Del Castillo Nieto et al. |
| 2004/0072839 | A1 | 4/2004 | Leonardi et al. |
| 2004/0092512 | A1 | 5/2004 | Maag et al. |
| 2004/0142926 | A1 | 7/2004 | Evrard et al. |
| 2004/0147581 | A1 | 7/2004 | Stephenson et al. |
| 2004/0180874 | A1 | 9/2004 | Putman et al. |
| 2004/0220184 | A1 | 11/2004 | Watsky et al. |
| 2004/0248883 | A1 | 12/2004 | Rottlaender et al. |
| 2005/0004105 | A1 | 1/2005 | Leahy et al. |
| 2005/0004137 | A1 | 1/2005 | Romano |
| 2005/0004138 | A1 | 1/2005 | Romano |
| 2005/0014764 | A1 | 1/2005 | Romano et al. |
| 2005/0038015 | A1 | 2/2005 | Bronzova et al. |
| 2005/0038036 | A1 | 2/2005 | Romano et al. |
| 2005/0043309 | A1 | 2/2005 | Clark et al. |
| 2005/0065158 | A1 | 3/2005 | Naylor et al. |
| 2005/0107395 | A1 | 5/2005 | Greenblatt et al. |
| 2005/0107396 | A1 | 5/2005 | Zwier et al. |
| 2005/0124613 | A1 | 6/2005 | Berger et al. |
| 2005/0130962 | A1 | 6/2005 | Berger et al. |

FOREIGN PATENT DOCUMENTS

| | | |
|---|---|---|
| EP | 372657 | 6/1990 |
| EP | 0 281 309 | 12/1991 |
| EP | 189 612 B1 | 11/1992 |
| EP | 376607 B1 | 3/1994 |
| EP | 650964 | 5/1995 |
| EP | 710481 | 5/1996 |
| EP | 985414 B1 | 8/2003 |
| WO | WO 91/09853 | 7/1991 |
| WO | WO 9511243 | 4/1995 |
| WO | WO 95/25733 | 9/1995 |
| WO | WO 97/03982 A1 | 2/1997 |
| WO | WO 97/07120 | 2/1997 |
| WO | WO 97/34883 | 9/1997 |
| WO | WO 98/16530 A1 | 4/1998 |
| WO | WO 98/42344 | 10/1998 |
| WO | WO 99/14213 | 3/1999 |
| WO | WO 99/55672 A1 | 11/1999 |
| WO | WO 99/65887 A1 | 12/1999 |
| WO | WO 00/29397 | 5/2000 |
| WO | WO 00/40554 A1 | 7/2000 |
| WO | WO 01/09111 | 2/2001 |
| WO | WO 01/14330 | 8/2001 |
| WO | WO 02/36562 | 5/2002 |
| WO | WO 02066473 C1 | 8/2002 |
| WO | WO 03/074518 | 9/2003 |
| WO | WO 03/078396 A1 | 9/2003 |
| WO | WO 03/078417 A1 | 9/2003 |
| WO | WO 2004/043465 | 5/2004 |
| WO | WO 2004/046124 | 6/2004 |
| WO | WO 2004/054972 | 7/2004 |
| WO | WO 2005/014552 | 2/2005 |
| WO | WO 2005/063296 | 7/2005 |

OTHER PUBLICATIONS

J. M. Halperin et al., "Discriminant Validity of Attention-Deficit Hyperactivity Disorder," *J. Am. Acad. Child Adolesc. Psych.*, 32(5):1038-1043, Sep. 1993.

M. L. Wolraich et al., "Stimulant Medication Use by Primary Care Physicians in the Treatment of Attention Deficit Hyperactivity Disorder," *Pediatrics*, 86(1):95-101, Jul. 1990.

D. M. Ross & S. A. Ross, "Hyperactivity - An Overview," *Hyperactivity-Current Issues, Research, and Theory*, Second Edition, New York, Chapter 1, pp. 1-9, 1982.

D. J. Safer & J. M. Krager, "A Survey of Medication Treatment for Hyperactive/Inattentive Students," *J. Am. Med. Assoc.*, 206(15):2256-2258, Oct. 1998.

T. Spencer et al., "A Double-blind, Crossover Comparison of Methylphenidate and Placebo in Adults With Childhood-Onset Attention-Deficit Hyperactivity Disorder," *Arch. Gen. Psychiatry*, 52:434-443, 1995.

W. E. Pelham Jr. et al., "Empirically Supported Psychosocial Treatment for Attention Deficit Hyperactivity Disorder," *J. Clin. Child Psychol.*, 27(2):190-205, 1998.

F. X. Castellanos et al., "Quantitive Brain Magnetic Resonance Imaging in Attention-Deficit Hyperactivity Disorder," *Arch. Gen. Psychiatry*, 53:607-616, Jul. 1996.

C. K. Conners et al., "Nicotine and Attention in Adult Attention Deficit Hyperactivity Disorder (ADHD)," *Psychopharmacology Bulletin*, 32(1):67-73, 1996.

P. de Koning et al., "Eltoprazine in aggressive mentally handicapped patients: a double-blind, placebo- and baseline-controlled multi-centre study," *International Clinincal Psychopharmacology*, 9:187-194, 1994.

J. Schipper et al., "Neurochemical Profile of Eltoprazine," *Drug Metabolism and Drug Interactions*, 8(1-2): 85-114, 1990.

K. P. Schulz et al., "Relationship between central serotonergic function and aggression in prepubertal boys: effect of age and attention-deficit/hyperactivity disorder," *Psychiatry Res.* 101:1-10, 2001.

G. Malleret et al., "5-HT1B Receptor Knock-Out Mice Exhibit Increased Exploratory Activity and Enhanced Spatial Memory Performance in the Morris Water Maze," *J. Neurosci.*, 19(14):6157-6168, Jul. 1999.

G. Maura & M. Raiteri, "Cholinergic terminals in rat hippocampus possess 5-HT $_{1B}$ receptors mediating inhibition of acetylcholine release," *Euro. J. Pharmacol.*, 129:333-337, 1986.

D. A. Amara et al., "Serotonin 1B Receptor Regulation After Dorsal Subiculum Deafferentation," *Brain Research Bulletin*, 38(1):17-23, 1995.

M.C. Buhot & S. Naili, "Changes in Exploratory Activity Following Stimulation of Hippocampal 5-HT1A and 5-HT1B Receptors in the Rat," *Hippocampus*, 5:198-208, 1995.

M. H. de Vries et al., "Dose-proportionality of eltoprazine: Pharmacokinetics of single oral doses in healthy subjects," *Eur. J. Clin. Pharmacol.*, 41:485-488, 1991.

E. J. Nestler et al, "Sleep, Arousal, and Attention," *Molecular Neuropharmacology: A Foundation for Clinical Neuroscience*, Chapter 18, pp. 409-432, 2001.

S. R. Pliszka et al., "Inhibitory Control in Children with Attention-Deficit/Hyperactivity Disorder: Event-Related Potentials Indentifying the Processing Component and Timing of an Impaired Right-Frontal Response-Inhibition Mechanism," *Biol. Psychiatry*, 48:238-246, 2000.

M. C. Wilson, "Coloboma mouse mutant as an animal model of hyperkinesis and attention deficit hyperactivity disorder," *Neurosci. Biobehav. Rev.*, 24:51-57, 2000.

E. J. Hess et al., "Spontaneous Locomotor Hyperactivity in a Mouse Mutant with a Deletion Including the *Snap* Gene on Chromosome 2," *J. Neurosci.*, 12(7):2865-2874, 1992.

E. J. Hess et al., "Mouse Model of Hyperkinesis Implicates Snap-25 in Behavioral Regulation," *J. Neurosci.*, 16(9):3104-3111, 1996.

C. J. Heyser et al, "Coloboma hyperactive mutant exhibits delayed neurobehavioral developmental milestones," *Dev. Brain Res.*, 89:264-269, 1995.

S. C. Steffensen et al., "Coloboma Contiguous Gene Deletion Encompassing *Snap* Alters Hippocampal Plasticity," *Synapse*, 22:281-289, 1996.

J. Raber et al, "Coloboma Hyperactive Mutant Mice Exhibit Regional and Transmitter-Specific Deficits in Neurotransmission," *J. Neurochem.*, 68(1):176-186, 1997.

E. J. Hess et al., "Deletion Map of the Coloboma (*Cm*) Locus on Mouse Chromosome 2," *Genomics*, 21:257-261, 1994.

T. Sagvolden et al., "Altered reinforcement mechanisms in attention-deficit/hyperactivity disorder," Behav. Brain Res., 94:61-71, 1998.

T. Sagvolden & J. A. Sergeant, "Attention deficit/hyperactivity disorder—from brain dysfunctions to behaviour," Behav. Brain Res., 94:1-10, 1998.

R. J. Rodgers et al., "Anxiogenic-like effects of fluprazine and eltoprazine in the mouse elevated plus-maze: profile comparison with 8-OH-DPAT, CGS 12066B, TFMPP and mCPP," *Behav. Pharmacol*, 3:621-634, 1992.

G. Griebel et al., "Serenics fluprazine (DU 27716) and eltoprazine (DU 28853) enhance neophobic and emotional behaviour in mice," *Psychopharmacology*, 102:498-502, 1990.

F. Saudou et al., "Enhanced Aggressive Behavior in Mice Lacking 5-HT $_{1B}$ Receptor," *Science*, 265:1875-1878, Sep. 1994.

D. Brunner & R. Hen, "Insights into the Neurobiology of Impulsive Behavior from Serotonin Receptor Knockout Mice," *Annals N.Y. Acad. Sci.*, 836:81-105, Dec. 1997.

S. Ramboz et al., "Serotonin receptor 1A knockout: An animal model of anxiety-related disorder," *Proc. Nat'l Acad. Sci. USA*, 95:14476-14481, Nov. 1998.

X. Zhuang et al., "Altered Emotional States in Knockout Mice Lacking 5-HT1A or 5-HT1B Receptors," *Neuropsychopharmacol.*, 21(2S):52S-60S, 1999.

J. Monterosso & G. Ainslie, "Beyond discounting: possible experimental models of impulse control," *Psychopharmacol.*, 146:339-347, 1999.

J. P. C. De Bruin et al., "Role of the prefrontal cortex of the rat in learning and decision making: effects of transient inactivation," *Prog. Brain Res.*, 126:103-113, 2000.

A. Tomie et al., "Ethanol induces impulsive-like responding in a delay-of-reward operant choice procedure: impulsivity predicts autoshaping," *Psychopharmacol.*, 139:376-382, 1998.

L. De Groote et al., "The Effects of selective serotonin reuptake inhibitors on extracellular 5-HT levels in the hippocampus of 5-HT $_{1B}$ receptor knockout mice," *Eur. J. Pharmacol.*, 439:93-100, 2002.

R. R. Gaindtdinov et al., "Role of Serotonin in the Paradoxical Calming Effect of Psychostimulants on Hyperactivity," *Science*, 283:397-407, Jan. 1999.

E. Taylor, "Developmental neuropsychopathology of attention deficit and impulsiveness," *Dev. and Psychopathol.*, 11:607-628, 1999.

S. Ramboz et al., "Territorial and maternal aggression in mice lacking 5-HT1B receptors," Regular Research Article.

D. Kohen, "Eltoprazine for aggression in mental handicap," *Lancet*, letter, 341:628-629, Mar. 1993.

J. Tiihonen et al., "Eltoprazine for aggression in schizophrenia and mental retardation," *Lancet*, letter, 341:307, Jan. 1993.

E. W. Fish et al., "Aggression heightened by alcohol or social instigation in mice: reduction by the 5-HT $_{1B}$ receptor agonist CP-94,253," *Psychopharmacology*, 146:391-399, 1999.

T. Pattij et al., "Operant learning and differential-reinforcement-of-low-rate 36 sec responding in 5-HT $_{1A}$ and 5-HT $_{1B}$ receptor knockout mice," Chapter 5, Dissertation Thesis.

M. Raghoebar et al., "Pharmacokinetics of eltoprazine in healthy male subjects after single dose oral and intravenous administration," *Br. J. Clin. Pharma.*, 30:879-883, 1990.

D. R. Cherek et al., "Acute Effects of Eltoprazine on Aggressive and Pint-Maintained Responding of Normal Male Participants: Phase I Study," *Exp. Clin.Psychopharma.*, 3(3):287-293, 1995.

A. A. Harrison et al., "Central 5-HT depletion enhances impulsive responding without affecting the accuracy of attentional performance: interactions with dopaminergic mechanisms," *Psychopharmacology*, 133:329-342, 1997.

S. C. Steffensen et al., "Transgenic rescue of SNAP-25 restores dopamine-modulated synaptic transmission in the coloboma mutant," *Brain Research*, 847:186-195,1999.

C. L. Parks et al., "Increased anxiety of mice lacking the serotonin1A receptor," *Proc. Natl. Acad. Sci.* USA, 95:10734-10739, Sep. 1998.

M. L. Verdonk et al., "Structure of Eltoprazine," *Acta Cryst.*, C48(12):2271-2273, Dec. 1992.

S. V. Faraone et al., "Separation of DSM-III attention deficit disorder and conduct disorder: evidence form a family-genetic study of American child psychiatric patients," *Psychological Medicine*, 21:109-121, 1991.

R. L. Findling et al., "Psychopharmacology of ADHD: Children and Adolescents," *J. Clin. Psychiatry*, 59(S7):42-49, 1998.

W. M. A. Verhoeven, "Eltoprazine in mentally retarded self-injuring patients," *Lancet*, letter, 340:1037-1038, Oct. 1992.

B. Boutrel et al., "Key role of 5-HT 1B Receptors in the Regulation of Paradoxical Sleep as Evidenced in 5-HT1VB Knock-Out Mice," *Journal of Neuroscience*, 19(8):3204-3212, Apr. 1999.

J. J. Lucas et al., "Absence of Fenfluramine-Induced Anorexia and Reduced c-fos Induction in the Hypothalmus and Central Amygdaloid Complex of Serotonin 1B Receptor Knock-Out Mice," *Journal of Neuroscience*, 18(14):5537-5544, Jul. 1998.

O. Massot et al., "5-HT1B Receptors: A Novel Target for Lithium: Possible Involvement in Mood Disorders," *Neuropsychopharmacology*, 21(4):530-540,1999.

T. Puumala et al., "Changes in Activities of Dopamine and Serotonin Systems in the Frontal Cortex Underlie Poor Choice Accuracy and Impulsivity of Rats in an Attention Task," *Neuroscience*, 83(2):489-499, 1998.

J. L. Evenden, "The pharmacology of impulsive behavior in rats VII: the effects of serotonergic agonists and antagonists on responding under a discrimination task using unreliable visual stimuli," *Psychopharmacology*, 146:422-431, 1999.

B. Olivier et al., "Discriminative Stimulus Properties of Eltoprazine in the Pigeon," *Pharmacol. Biochem. Behav.*, 64(2):421-427, 1999.

J. M. Odonnell and L. S. Seiden, "Differential-Reinforcement-of-Low-Rate 72-Second Schedule: Selective Effects of Antidepressant Drugs," *J. Pharm. Exp. Therap.*, 224(1): 80-88, 1983.

J. B. Richards et al., "DRL Interresponse-Time Distributions: Quantification By Peak Deviation Analysis," *J. Exp. Anal. Behav.*, 60(2): 361-385, Sep. 1993.

K. E. Sabol et al., "Amphetamine analogs have differential effects on DRL 36-s schedule performance," *Psychopharmacology*, 121:57-65, 1995.

S. V. Faraone and J. Biederman, "The neurobiology of attention deficit hyperactivity disorder," *Neurobiology Of Mental Illness*, Chapter 60, pp. 788-801, 1999.

J. Mos et al, "The effects of dorsal raphe administration of eltoprazine, TFMPP and 8-OH-DPAT on resident intruder aggression in the rat," *European J. Pharm.*, 238:411-415, 1993.

K. Brophy et al, "Synaptosomal-associated protein 25 (SNAP-25) and attention deficit hyperactivity disorder (ADHD): evidence of linkage and association in the Irish population," *Molecular Psychiatry*, 7:913-917, 2002.

C. L. Barr et al., "Identification of DNA variants in the SNAP-25 gene and linkage study of these polymorphisms and attention-deficit hyperactivity disorder," *Molecular Psychiatry*, 5:405-409, 2000.

D. Brunner et al. "Anxiety, Motor Activation, and Meternal-Infant Interactions in 5HT $_{1B}$. Knockout Mice," *Behavioral Neuroscience*, 113(3): 1-15, 1999.

Z. Hawi et al, "Serotonergic system and attention deficit hyperactivity disorder (ADHD): a potntial susceptibility locus at the 5-HT $_{1B}$ receptor gene in 273 nuclear families from a multi-centre sample," *Molecular Psychiatry*, 7:718-725, 2002.

International Search Report, Dec. 12, 2002.

Adamec et al., The interaction of hunger, feeding, and experience in alteration, of topography of the rats predatory response to mice. Behav. Biol. vol. 22, pp. 230-243, 1978.

Adams, DB. "Brain mechanisms for offense, defense and submission." Behav. Brain Sci., vol. 2, pp. 201-241, 1979.

Adams, DB. "The relation of scent-marking, olfactory investigation, and specific postures in the isolation-induced fighting of rats." Behaviour, vol. 56, pp. 286-297, 1976.

Adams, DB. Motivational systems of agonistic behavior in muroid rodents: A comparative review and neural model. Aggr. Behav., vol. 6, pp. 295-346, 1980.

Ader et al., Free 3-methoxy-4-hydroxyphenylethyleneglycol in the central nervous system of the rat: semi-automated fluorometric assay, turnover and effects of drugs. J Neurochem vol. 32, pp. 1761-1768, 1979.

Ahlenius et al., "Effect of a new type of 5-HT receptor agonist on male rat sexual behavior." Pharmacol. Biochem. Behav. vol. 15, pp. 7$5-792, 1981.

Ahlenilis et al., "Further evidence for an inhibitory role of central 5-HT in male rat sexual behaviour." Psychopharmacology vol. 68, pp. 217-220, 1980.

Ahlenius et al., "Lisuride, LY-141865 and 8-OH-DPAT facilitate male rat non-dopaminergic mechanism." Psychopharmacology vol. 83, pp. 330-334, 1984.

Albert et al., "The inhibitory modulation of agonistic behaviour in the rat brain: a review." Neurosci. Biobehav. Rev, vol. 6, pp. 125-143, 1982.

Andreassi et al., "Electrodermal activity and behaviour." Psychophysiology: human behaviour and psycholo ical response. Andreassi (Ed.) pp. 173-198, 1980.

Asarch et al., ".5-HT-IA and 5-HT-1B selectivity of two phenylpiperazine derivatives: evidence for 5-HT-1B heterogeneity." Life Sci. vol. 36, pp. 1265-1273, 1985.

Asberg et al. "Biological Factors in Suicide" Suicide. Roy (Ed.) pp. 47-71, 1986.

Babbini et al., "Anorexic and behavioural effects of a new imidazo-isoindole derivative (Mazindol) in comparision with d-amphetamine in the rat." Pharmacology vol. 15, pp. 46-56, 1977.

Baenninger, R. "Some aspects of predatory behavior." Aggr. Behav. vol. 4, pp. 287-311, 1978.

Banki et al. "Animal and human aspects of aggression." Serotonin-related psychiatric syndromes: clinical and therapeutic links. Cassano and Akiskal (Eds.), pp. 27-33, 1991.

Bardin et al, "Profound, non-opoid analgesia produced by the high-efficacy 5-HTIA agnist F 13640 in the formalin model of tonic nociceptive pain." Pharmacology, vol.. 67, No. 4, pp. 182-194, 2003.

Barfield et al., "Gonadal influence on agonistic behavior in the male domestic rat." Horm. Behav. vol. 3, pp. 247-259, 1972.

Barfield, RJ. "The hypothalamus and behaviour with special reference to the hormonal control of sexual behaviour." Poultry Sci. vol. 58, pp. 1625-1632, 1979.

Barr et al., "Neuropharmacological regulation of mousekilling by rats." Behav. Biol., vol. 17, pp. 143-159, 1976.

Bean et al., "Effects of benzazecpine (Sch-12679) on shock-induced fighting and locomotor behaviour in rats." Psychopharmacology vol. 59, pp. 189-192, 1978.

Bell et al. "Drugs as research tools in psychology: cholinergic drugs and aggression." Neuropsychobiology, vol. 14, pp. 181-192, 1985.

Bell et al., "The effects of two "anti-aggressive" compounds, an indenopyridine and a benzothiazcpin, on shock-induced defensive fighting in rats." Prog. Neuro-Psychopharmacol. vol. 3, pp. 399-402, 1979.

Bennet et al., "Serotonin and lysergic acid diethylamide binding in rat brain membranes: relationship to postsynaptic serotonin receptor." Mol. Pharmacol. vol. 12, pp. 373-389, 1976.

Benton et al., "Behavioural examinations of the anti-aggressive drug fluprazine." Behav. Brain Res. vol. 10, pp. 325-338, 1984.

Benton, D. "The extrapolation from animals to man: the example of testerone and aggression." Multidisciplinary approaches to aggression research. Brain and Benton (Eds.) pp. 401-418, 1981.

Bergen et al. "The course of tardive dyskinesia in patients on long-term neuroleptics." Br. J. Psychiatry, vol. 154, pp. 523-528, 1989.

Bermond et al., "Aggression induced by stimulation of the hypothalamus: effects of androgens." Pharmacol. Biochem. Behav. vol. 16, pp. 41-45, 1982.

Bevan ct al., "Serotonergic function and aggression in animals." Serotonin: actions, receptors, pathophysiology. Mylecharane et al. (Eds.) pp. 101-108, 1990.

Bioulac et al. "Serotoninergic dysfunction in the 47 XYY syndrome." Biological Psychiatry, vol. 15, pp. 917-923, 1980.

Birch et al, "N-Substituted (2,3-dihydro-I, 4-benzodioxin-2yl)methylamine dderivatives as D2 antagonists/5-HT IA partial agonists with potential as atypical antipsychotic agents." J. Medicinal Chemistry, vol. 42, No. 17, pp. 3342-3355, 1999.

Blanchard et al., "Attack and defensive behaviors in the albino mouse." Aggr. Behav. vol. 5, pp. 341-352, 1979.

Blanchard et al., "Pain and aggression in the rat," Behav. Biol. vol. 23, pp. 291-305, 1978.

Blundell, JE. "Is there a role for serotonin (5-hydroxytryptamin) in feeding?" Int. J. Obesity2 vol. 1, pp. 15-42, 1977.

Bond et al., "A method to elicit aggressive feelings and behaviour via provocation." Biological Psychology, vol. 22, pp. 69-79, 1986.

Bond et al., "Benzodiazepines and aggression." Psychopharmacology of aggression. M. Sandler (Ed.) pp. 173-182, 1979.

Bond, AJ., "pharmacological manipulation of aggressiveness and impulsiveness in healthy volunteers." Prog. Neuro-Psychopharmacol. & Biol. Psychiat., vol. 16, pp. 1-7, 1992.

Bradford et al., "Serenics: the pharmacology of fluprazine and DU 28412." Ethopharmacological Aggression Research. Miczek, Kruk and Olivier (Eds) pp. 191-201, 1984.

Braestrup et al., Pharmacological characterisation of benzodiazepine receptors in the brain. Eur. J. Pharmacol. vol. 48, pp. 263-270, 1978.

Brain et al., "A preliminary ethological analysis of the effects of DU 21716 on intcrimale aggression in Swiss-Webster mice." Aggr. Behav. vol. 9, pp. 117, 1983.

Brain, PF. "Biological explanations of human aggression and the resulting therapies offered by such approaches: a critical evaluation." Advances in the study of aggression. Blanchard and Blanchard (Eds.) vol I: pp. 63-102, 1984.

Brain, PF. "Hormones and aggression in infra-human vertebrates." The biology of aggression. Brain and Benton, (Ed.) pp. 181-213, 1981.

Brown et al. "Aggression, suicide, and serotonin: relationship in CSF amine metabolites." American Journal of Psychiatry, vol. 139, pp. 741-746, 1982.

Brown et al. "Clinical assessment of human aggression and impulsivity in relationship to biochemical measures." Violence and suicidality: Perspectives in clinincal and psychobiological research., VanPraag, Plutchik and Apter (Eds.), pp. 184-217, 1990.

Brown et al. "Human aggression and suicide, Their relationships to neuropsychiatric diagnosis and serotonin metabolism." Serotonin in Biological Psychiatry. Ho et al (Eds.) pp. 287-307, 1982.

Brown et al., "Aggression in human correlates with cerebrospinal fluid amine metabolites." Psychiatry Research Reports, vol. 1, pp. 131-139, 1979.

Burt et al., "Properties of (3H) haloperidol and (3H) dopamine receptors in calf brain membranes." Mol. PharmacoL, vol. 12, pp. 800-812, 1976.

Campbell et al., "Drugs in aggressive behavior." J. Am. Acad. Child Psychiatry. vol. 21, pp. 107-117, 1982.

Carli et al, "S 15535, a benzodioxopiperazine acting as presynaptic agonist and postsynaptic 5-HT IA receptor antagonist, prevents the impairment of spatial learning caused by intrahippocampal scopolamine." British J. Pharmacology, vol. 128, No. 6, pp. 1207-1214, 1999.

Carvalho et al, "Rational planning of antagonist analogues for imaging serotomin 5-HT1A receptor subtypes based on 99mTc." Technical Reports Seris—International Atomic Energ Agency, vol. 426, pp. 19-36, 2004.

Charig et al. "L-tryptophan and prolactin release: evidence for interation between 5Htl and 5HT2 receptors." Human Psychopharmacology, vol. 1, pp. 93-97, 1982.

Charney et al. "The efffects of intravenous L-tryptophan on prolactin and growth hormone and mood in healthy subjects." Psychopharmacology, vol. 77, pp. 217-222, 1982.

Cherek et al. "Effects of acute diazepam and d-ampehtamine administration on aggressive and escape responding of normal male subjects." Psychopharmacology, vol. 100, pp. 173-181, 1990.

Cherek et al. "Effects of alcohol on human aggressive behaviour." J. Stud. On Alcohol, vol. 46, pp. 321-328, 1985.

Cherek et al. "Effects of drugs on human aggressive behaviour." Psychiat. Res., vol. 8, pp. 137-145,1983.

Cherek et al. "Effects of drugs on human aggressive behaviour." Advanced in human psychopharmacology, vol. IV, Burrows and Werry (Eds.), pp. 239-290, 1987.

Cherek et al. "Effects of triazolam on human aggressive, escape and point-maintained responding." Pharmac. Biochem. Bchav., vol. 40, pp. 835-839, 1991.

Cherek et al., "Effects of amphetamine on human aggressive behaviour." Psychopharmacology, vol. 88, pp. 381-386, 1986.

Cherek et al., "Effects of secobarbital on human aggressive and non-aggressive responding." Drug Ale. Depend., vol. 24, pp. 21-29, 1989.

Cherek, DR., "Effects of smoking different doses of nicotine on human aggressive behaviour." Psychopharmacology, vol. 75, pp. 339-345, 1981.

Claassen et al., "Fluvoxamine, a specific 5-hydroxytryptamine uptake inhibitor." Br. J. Phannacol., vol. 60, pp. 505-516,1977.

Claassen et al., "Pharmacology of clovoxatnine, a new non-tricyclic antidepressant." Arzneim. Forsch/Drug Res. vol. 28, pp. 1756-1766, 1978.

Clark et al., "Enhancement of sexual motivation in male rats by yohimbine." Science vol. 225, pp. 847-849, 1984.

Clemens et al., "Further evidence that serotonin is a neurotransmitter involved in the control of prolactin secretion." Endocrinology vol. 100, pp. 692-698, 1977.

Cloninger, CR. "Antisocial behavior." Clinical Psychopharmacology. Hippius and Winokur (Eds.) Excerpta Medica, pp. 353-370, 1983.

Coccaro, EF. "Central serotonin and impulsive aggression." British Journal of Psychiatry, vol. 166 (suppl. 8), pp. 52-62, 1989.

Cocchi et al., "Conformational analysis and theoretical quantitative size and shape-affinity relationships of N4-protonatedNI-arylpiperazine 5-HTIA serotoninergic ligands," Theochem, vol. 397, pp. 129-145, 1997.

Cook et al., "Reinforcement schedules and extrapolations to humans from animals in behavioural pharmacology." Fed. Proc., vol. 34, pp. 1889-1897, 1975.

Cools, A. "Psychopharmacology and aggression: an appraisal of the current situation." The Biology of aggresssion. Brain and Benton (Eds.) pp. 131-145, 1981.

Coppola et al., "Psychotropic drug profiles: Comparison by topographic maps of absolute power." Neuropsychobiology, vol. 18, pp. 97-104, 1987.

Costall et al., "Climbing behaviour induced by apomorphine in mice: a potential model for the detection of neuroleptic activity." Eur. J. Pharmacol. vol. 50, pp. 39-46, 1978.

Cowen et al. "Neuroendocrine responses to tryptophan in major depression." Arch. Gen. Psychiatry, vol. 44, pp. 958-966, 1987.

Coyle et al., "Catecholantinc uptake by synaptosomes in homogenate of rat brain; stereospecificity in different areas." J. Phannacol. Exp. Ther. vol. 170, pp. 221-231, 1969.

Crawley et al., "Preliminary report of a simple animal behavior model for the anxiolytic effects of V benzodiazepines." Pharmacol. Bioch. Behav. vol. 13, pp. 167-170, 1980.

Creese et al., "(3H) Spiroperidol labels dopamine receptors in rat pituitary and brain." Eur. J Pharmacol., vol. 46, pp. 377-381, 1977.

Creese et al., "(3H) Spiroperidol labels serotonin receptors in rat cerebral cortex and hippocampus." Eur. J. Pharmacol. vol. 49, pp. 201-202, 1978.

Crowley et al., "The neurochemical control of mating behavior." Neuroendocrinology of reproduction. Physiology and behavior. Adler NT, (Ed.); pp. 451-484, 1981.

Dantzcr ct al., "Effccts of lithium on aggressive behaviour in domestic pigs." J. Vet. Pharmacol. Therap. Vol. 2, pp. 299-303, 1979.

Dar ula, JH., "Patterns of brain monoamine activity and aggressive behavior." Neurosci. Biobehav. Rev., vol. 2, pp. 101-113, 1978.

Day, K., "Psychiatric disorder in the middle-aged and elderly mentally handicapped." Br. J. Psychiatry, vol. 147, pp. 660-667, 1985.

De Boer et al., "Assay and properties of 4-aminobutyric 2-oxoglutaric acid transaminase anc succinic semialdehyde dehydrogenase in rat brain tissue." J. Neurochem, vol. 28, pp. 471-478, 1977.

DeBold et al., "Aggression persists after ovariectomy in female rats." Horm. Behav. vol. 18, pp. 177-190, 1984.

Dekeyne et al, "Generalization of serotonin (5-HT IA) agonists and the antipsychotics, clozapine, ziprasidone and S 16924, but not haloperidol, to the discriminative stimuli elicited by PD 128,907 and 7-OH-CPAT." Neuropharmacology, vol. 40, No. 7, pp. 899-910, 2001.

Dekeyne et al, "The selective scrotonin (5-HT) 1A receptor ligand, 515535, displays anxiolytic-like effects in the social interaction and Vogel models and suppresses dialysate levels of 5-HT in the dorsal hippocampus of freely-moving rats: a comparison with other anxiolytic agents." Psychopharmacology, vol. 152, No. 1, pp. 55-66, 2000.

Delina-Stula et al., "Differential effects of psychoactive drugs on aggressive responses in mice and rats." Psychopharmacology of aggression. Sandler M, (Ed.) pp. 41-60, 1979.

Delina-Stula et al., "The effects of antidcpressants on aggressiveness induced by social deprivation in mice." Pharmacol. Biochem. Behav., vol. 14 (Suppl 1) pp. 33-41, 1981.

Depue et al., "Conceptualizing a serotonintrait: A behavioural dimension of constraint." Anr NY Acad. Sci., vol. 487, pp. 47-62, 1986.

DiChiari et al., Nature, vol. 233, pp. 272-273, 1971.

Dixon, AK. "A. possible olfactory component in the effects of diazepam on social behavior of mice." Psychopharmacology vol. 77, pp. 246-252, 1982.

Dourish et al., "Characteristics of feeding induced by the serotonin agonist 8-hydroxy-2-(di-n-propylamino) tetrlin (8-OH-DP AT)." Brain Res. Bull., vol. 15, pp. 377-3 84, 1985.

Eichelman, B. "The Biology and sanatic experimental treatment of aggressive disorders." American Handbook of Psychiatry. Berger, Keith and Brodie (Eds.) vol. 8, pp. 651-678, 1986.

Eichelman, B. "Toward a rational pharmacotherapy for aggressive and violent behaviour." Hosp, Comm. Psychiatry, vol. 39, pp. 31-39, 1988.

Elliott, FA., "Propanolol for the control of the Belligerent behavior following acute brain damage." Annals of Neurology, vol. 1, pp. 489-491, 1977.

Erskine et al,, "Aggression in the lactating rat: effects of intruder age and test arena." Behav. Biol. vol. 23, pp. 52-66, 1978.

Erskine et al., "Intraspecific fighting during late pregnancy and lactation in rats and effects of litter removal." Behav. Biol., vol. 23, pp. 206-218, 1978.

Erskine et al., "Postpartum aggression in rats: II Dependence on material sensitivity to young and effects of experience with pregnancy and parturition." J. Comp. Physiol. Zoo]. vol. 94, pp. 495-505, 1980.

Essman, WB. "Benzodiazepines and aggressive behavior." Mod. Probl. Pharmacopsychiatry; vol. 13, pp. 13-28, 1978.

Essmann, WB., "Drug effects upon aggressive behaviour." Aggrression and violence, a psychological and clinical approach. Valzelli and Morgese (Eds.) pp. 150-175, 1981.

Flannelly et al., "Specific antiaggressive effects of fluprazine hydrochloride." Psychopharmacology, vol. 87, pp. 86-89, 1985.

Floody et al., "Aggressive behaviour among female hamsters: the hormonal basis for fluctuations in female aggressivenes correlated with estrous state," J. Comp. Physiol. Psychol. vol. 91, pp. 443-446, 1977.

Floody, Or. "Hormones and agression in female animals." Hormones and aggressive behaviour. Svare, BB (Ed.) pp. 39-89, 1983.

Frankenheim, J. "Effects of antidepressants and related drugs on the quantitatively analyzed EEG of beagles." Drug Devl. Res. vol. 2, pp. 197-213, 1982.

Fraser, D. "The behaviour of growing pigs during experimental social encounters." J. Agric. Sci. Cambridge, vol. 82, pp. 147-163, 1974.

Gandelman, R., "Androgen and fighting behavior." The Biology of Aggression. Brain and Benton, (Eds.), pp. 215-230, 1981.

Geller et al., The effects of meprobamate, barbiturates, d-amphetamine and promazine on experimentally induced conflict in the rat. Psychopharmacologia, vol. 1, pp. 482-492, 1960.

Gianutsos et al., "Aggression in mice after p-chloroamphetamine." Res. Comm. Chem. Pathol. Pharmacol., vol. 10, pp. 379-382, 1975.

Gibbons et al. "Manipulations of dietary tryptophan: effects on mouse killing and brain serotonin in the rat." Brain Res., vol. 169, pp. 139-153, 1979.

Glennon et al, "5-HT1D serotonin receptors: results of a structure-affinity investigation." Drug Development Research, vol. 22, No. 1, pp. 26-36, 1991.

Glennon, RA., "Site selective serotonin agonists as discriminative stimuli." Psychopharmacology, vol. 89, p. 135, 1986.

Gobert et al, "Modulation of the activity of central serotoninergic neurons by novel serotonin IA receptor agonists and antagonists: a comparision to adrenegic and dopaminergic neurons in rats." J.Pharmacology and Experimental Therapeutics, vol. 273, No. 3, pp. 1032-1046, 1995.

Goldberg et al. "The comparative efficacy of buspirone and diazepam in the treatment of anxiety." Am. J. Psychiatry, vol. 136, pp. 1184-1187, 1979.

Gozlan et al., Identification of presynaptic serotonin autoreceptors using a new ligand: 3H-PAT, Nature, vol. 305, pp. 140-142, 1983.

Grabowska, M. Influence of quipazine on sexual behaviour in male rats. Sexual behaviour: Pharmacology and Biochemistry. Sandier and Gessa, (Eds.) pp. 59-62, 1975.

Greenberg et al., "Alph-noradrenergic receptor binding in mammalian brain: differential labeling of agonist and antagonist states." Life Sci. vol. 19, pp. 69-76, 1976.

Guccione et al, "3D-QSAR using "multiconformer" alignment: the use of HASL in the analysis of 5-HT1A thienopyrimidinone ligands." J. Computer Aided Molecular Design, vol. 14, No. 7, pp. 647-657, 2000.

Gunn, 3. "Drugs in the violence clinic." Psychopharmacology of aggression. Sandier, M. (Ed.), pp. 183-195, 1979.

Hall, TR, "Control of prolactin secretion in the vertebrates—a comparative survey." Gen. Pharmacol., vol. 15: 189-195, 1984.

Handley et al., "Effects of alpha-adrenergic agonists and antagonists in a maze-exploration model of "fear"-motivated behaviour." NS Arch. Pharmacol., vol. 327, pp. 1-5, 1984.

Hartog et al., "Eltoprazine hydrochloride." Drugs Future, vol. 13, pp. 222-223, 1988.

Heinrich et al, "Synthesis and structure-activity relationship in a class of indolebutylpiperazines as dual 5-HT IA receptor agonists and serotonin reuptake inhibitors." J. of Medicinal Chemistry, vol. 47, No. 19, pp. 4684-4692, 2004.

Heninger et. al. "Serotonergic function in depression," Arch. Gen. Psychiatry, vol. 41, pp. 398-402, 1984.

Herman et al., "Effects of morphine and naloxone on separation distress and approach attachment: evidence for opiate mediation of social affect." Pharmacol. Biochem. Behav., vol. 9, pp. 213-220, 1978.

Herschel et al., "Evidence for two types of binding of (3H)GABA and (3H)muscimol in rat cerebral cortex and cerebellum." Life Sci., vol. 1849-1854, 1979.

Herz, A. "Drugs and the conditional avoidance response." International Review of Neurobiology. Pfeiffer and Smythies (Eds.), vol. 2, pp. 229-277, 1960.

Hilleret al., "Specific high affiininty (3H)ethylketocyc I azocine binding in rat central nervous system: lack of evidence for k-receptors." J. Pharmacol. Expt. Ther., vol. 214, pp. 516-519, 1980.

Hinde, RA. "The bases of aggression in animals." Psychosom. Res., vol. 13, pp. 213-219, 1969.

Hindmarch et al., "A 1,4 benzodiazepine, Ternazepam: Its effects on some psychological aspects of sleep and behaviour." Arzneimittel Forschung, vol. 25, No. 11, pp. 1836-1839, 1975.

Hindmarch et al., "Critical flicker fusion frequency (CFFF): the effects of psychotropic compounds" Pharmacopsychiatrica, vol. 15, Suppl 1, pp. 44-48, 1982.

Hindmarch et al., "The effect of subchronic administration of three dose levels of a 1, 5 benzodiazepine derivative, clobazam, on subjective aspects of sleep and assessment of psychomotor performance the morning following night time medication." Arzneimittel Forschung, vol. 28, No. 11, pp. 2169-2172, 1978.

Hindmarch et al., "The effects of midazolam in conjunction with alcohol on sleep, psychomotor performance and car driving ability." Int. J. Clin. Pharm. Res., vol. 5, pp. 323-329, 1983.

Hoebel, BG. "Pharmacologic control of feeding." Ann. Rev. Pharmacol. Toxicol., vol. 17, pp. 605-621, 1977.

Hoebel, BG. "Three anorectic drugs: similar structures but different effects on brain and behavior." Int. 3. Obesity, vol. 2, pp. 157-166, 1978.

Horovitz et al., "Selective block of rat mouse-killing by antidepressants." Life Sci., vol. 4, pp. 1909-1912, 1965.

Inamdar et al. "Violent and suicidal behavior in psychotic adolescents." Am J. Psychiatry, vol. 139, poages 932-935, 1982.

Iti 1, TM. "Drug treatment in the management of aggression." MultidiscipUnary approaches of aggression research. Brain and Benton, (Eds.), pp. 489-502, 1981.

Itil et al., "Drug treatment of human aggression." Prog. Neuro-Psychopharmacol. vol. 2, pp. 659-669, 1978.

Itil et al., "Pharmacological management of human violence." Mod. Probl. Pharmacopsychiatry, vol. 13, pp. 139-158, 1978.

Itil, TM. "The discovery of psychotropic drugs by computer analyzed cerebral bioelectric potentials (CEEG)." Drug Dev. Res., vol. 1, pp. 373-407, 1981.

Jacobs et al., "An animal behavior model for decreased central serotonergic function." Adv. Ex. Med. Biol., vol. 133, pp. 657-680, 1981.

Jacobs et al., "An animal behavioral model for studying the actions of LSD and related hallucinogens." Science, vol. 194, pp. 741-743, 1976.

Jacobs et al., "Behavioural effects of LSD in the cat: proposal of an animal behaviour mode for studying the actions of hallucinogenic drugs." Brain Res., vol. 132, pp. 301-314, 1977.

Jacobs et al., "Cats develop tolerance to d-amphetamine's effects upon locomotion and stercoyped behaviors." Eur. J. Pharmacol., vol. 69, pp. 353-356, 1981.

Jacobs et al., "Comparative effects of hallucinogenic drugs on behaviour of the cat." Commun. Ps cho.harmacol., vol. 1, .ales 243-254, 1977.

Jacobs, BL. "An animal bwehavior model for studying central serotonergic synapses." Life Sci., vol. 19, pates 777-786, 1976.

Jahn et al., "Pharmkologische und toxikologische Prufung des neuen Antiphlogisticums Azapropazon + 3 Dinethylamino—7—methyl—1,2—(m-propylmaloxyl)—1,2 dihydro—1,2,4—benzotriazin." Arzneim Forsch, vol. 19, pp. 36-52, 1969.

Jalowiec et al., "Opioid modulation of ingestive behavior." Pharmacol. Biochem. Behav., vol. 15, pp. 477-484, 1981.

Janssen et at., "Chemistry and pharmacology of compounds related to 4-(4-hydroxy-4-phenylpiperidino)-butyrophenone. Part IV. Influence of haloperidol (R 1625) and of chlorpromazine on the behaviour of rats in an unfamiliair "open field" situation." Psyhoparmacologia, vol. 1, pp. 389-392, 1960.

Jansse et al., "Effects of various drugs on isolation-inducing fighting behavior of male mice." J. Phannoacol. Ex.. Ther., vol. 129, pp. 471-475 1960.

Janssen et al., "Is it possible to predict the clinical effects of neuroleptic drugs (major tran, uillizers from animal data." Arzneim Forsch, vol. 17, pp. 848-854, 1967.

Janssen et al., "The peripheral and central anticholinergic properties of benzetimide (R 4929) and other atropine-like drugs as measured in a new anti-pilocarpine test in rats." Ps cho.harmacolo:ia, vol. 11, a:es 231-254, 1967.

Jenkins et al. "Therapeutic use of propanolol for intermittent explosive disorder." Mayo Clinic Proceddin:s vol. 62, ,a_es 204-214, 1987.

Kane et al. "Tardive dyskinesia workgroup report." Psychopharmacol. Bull., vol. 16, pp. 35-36, 1980.

Kantak et al., "Facilitation of shock-induced fighting following intraventricular 5,7- dihydrotryptamine and 6-hydroxy DOPA." Psychopharmacology, vol. 74, pp. 157-160, 1981.

Karli et al., "Rat-mouse interspecific aggressive behaviour and its manipulation by brain ablation and by brain stimulation." Aggressive Behaviour. Garattini and Sigg (Eds.). pp. 47-55, 1969/.

Karli, P. "Conceptual and methodological problems associated with the study of brain mechanisms underlying aggressive behaviour." The biology of aggression. Brain and Benton Eds. pp. 323-361, 1981.

Karli, P. "The Norway rat's killing response to the white mouse: an experimental analysis." Behaviour, vol. 10, a:es 81-103, 1956.

Kato et al., "Effect on starvation on NADPH-dependent enzymes in liver microsomes of male and female rats." J. Pharmacol Exp. Ther., vol. 150, pp. 279-284 1969.

Katz, R. "Role of serotonergic mechanisms in animal models of predation." Progr. Neuro.s cho.harmacol. Biol. Psychia., vol. 4, pp. 21-231, 1980.

Koolbaas, IM. "Hypothalamically induced intraspecific aggressive behaviour in the rat." Ex.. Brain Res., vol. 32, pp. 365-375, 1978.

Kostowski, E. "Effects of sedatives and major tranquilizers on aggressive behavior." Mod. Probl. Pharmacopsychiatry, vol. 13, pp. 1-12, 1978.

Krijzer et al., "Classification of psychotropic drugs by rat EEG analysis: the anxiolytic profile in comparison to the antidepressant and neuroleptic profile." Neuropsychobiology, vol. 18, pp. 51-56, 1987.

Krijer et al., "Comparision of the (pro)convulsive properties of fluvoxamine and clovoxamine with eight other antidepressants in an animal model." Neuropsychobiology, vol. 12, pp. 249-254, 1984.

Krijzer et al., "Effects of antidepressants on the EEG of the rat." Neuropsychobiology, vol 9, pp. 167-173, 1983.

Krsiak et al. "Can social agonistic interations be used to detect anxiolytic activity of drugs?" Etho pharmacological aggression research. Mczek et al. (Eds.) pp. 93-144, 1984.

Krsiak et al., "Psychopharmacological aspects of aggression: A review of the literature and some new experiments." J. Psychosom. Res., vol. 13, pp. 243-252, 1969.

Krsiak, M. "Behavioral changes and aggessivity evoked by drugs in mice." Res. Comm. Chem. Pathol. Pharmacol., vol. 7, pp. 253-257, 1974.

Krsiak, M. "Effects of drugs on behaviour of aggressive mice." Br. J. Pharmacol., vol. 65, pp. 525-533, 1979.

Krsiak, M. "Timid singly-housed mice: their value in preduction of psychotropic activity of drugs." Br. J. Pharmacol., vol. 55, pp. 141-150, 1975.

Kruk et al., "Brain-stimulation induced agonistic behavior: A novel paradigm in ehopharmacological aggression research." Ethopharmacological Aggression Research, Miczek, Kruk and Olivier (Eds.) pp. 157-177, 1984.

Kruk et al., "Comparison of aggressive behaviour induced by electrical stimulation in the ethothalamus of male and female rats," Progr. Brain Res., vol. 61 pp. 303-314, 1984.

Kruk et al., "Discriminant analysis of the locatization of aggression-inducing electrode placements in the hypothalamus of male rats." Brain Res., vol. 260, pp. 61-79 1983.

Kruk et al., "Ethopharmacology of hypothalmic aggression in the rat." Ethopharmacology of agonistic behavior in animals and humans, Olivier, Mos and Brian (Eds.), pp. 33-45 1987.

Kruk et al., "Is there evidence for a neural correlate of an aggressive behavioural system in the hypothalamus of the rat?" Progr. Brain Res., vol. 53, pp. 385-390, 1980.

Kruk et al., "The induction of aggressive behaviour by eletrical stimulation in the bA-othalamus of male rats." Behaviour, vol. 70, pp. 292-322,1979.

Kuipers et al., "5-HT IA versus D2-receptor selectivity of Flesinoxan and analogous N4- substituted N1 - arylpiperazines." J. Medicinal Chemist, vol. 40, No. 3, pp. 300-312, 1997.

Kuipers et al, "N4-Unsubstituted N1-arylpiperazines as high-affinity 5-HTIA receptor ligands." J. Medicinal Chemis-, vol. 38 No. 11, pp. 1942-1954, 1995.

Kulkarni, AS., Life Sci., vol. 7, pp. 125-128, 1968.

Kuribana et al., "Correlation between anti avoidance activities of antipsychotic drugs in rats and daily clinical doses." Pharmacol. Biochem. Behav., vol. 14, -pp. 181-192, 1981.

Lagerspetz, K. "Combining aggression studies in infra-humans and man." Multidisciplinary approaches to aggression research. Brain and Benton (Eds.), pp. 389-400, 1981.

Lammers et al, "Pharmacokinetics of eltoprazme in the dog." Drug Metabolism and Drug Interactions, vol. 8, No. 1-2, pp. 141-148, 1990.

Lapierre et al. "Pharmacologic management of aggressivity and self-mutilation in the mentally retarded." Psychiatric. Clin. North America, vol. 4, pp. 745-754, 1986.

Lehman et al., "A statistical and motivational analysis of the social behaviors of the male laboratory rat." Behaviour, vol. 61, pp. 238-275, 1977.

Leslie et al., "Opioid binding properties of brain and peripheral tissues: evidence for heterogeneity in opioid ligand binding sites." J. Pharmacol. Exp. Ther., vol. 214, pp. 395-402, 1980.

Levi, L., "stress and distress in response to psychosocial stimuli." Acta Med. Scand. Suppl. 548, 1972.

Lidberg et al., "5Hydroxyindoleacetic acid levels in attempted suicides who have killed their children." Lancet, vol. 2, pp. 928, 1984.

Lidberg et al., "Homocide, suicide and CSF 5-HIAA." Acta Psychiatr. Scand., vol. 71, pp. 230-236, 19.85.

Linnoila et al. "Low cerebrospinal fluid 5-hydroxyindoleacetic acid concentration differeniates impulsive from non-impulsive violent behaviour." Life Sci., vol. 33, pp. 2609-2614, 1983.

Linnoila ct al. "Monoamines, glucose metabolism and impluse control." Violence and suicidality: pcrspcctives in clinical and psycho-biological research. pp. 218-241 1990.

Lisk, RD. "Neural localization far androgen activation of copulatory behavior in the male rat." Endocinolof, vol. 80, pp. 754-761, 1967.

Lopez-Thor, JJ., "Serotonin and psychiatric disorders." Int. Clin. Psychopharmacol. vol. 7, su.. 12, pp. 5-11, 1992.

Lopez-Rodriguez et al, "Design and synthesis of S-(-)-2-[[4-napth-1-yl)piperazin-1- y]methyl]-1,4dioxoperhydropyrrolo[1,2-a]pyrazine (CSP-2503) using computational simulation. A 5-HT1A receptor agonist." Bioorganic and Medicinal Chemistry Letters, vol. .13, No. 8, pp. 1429-1432, 2003.

Lopez-Rodriguez et al, "Pd(0) amtivation of benzimidazoles as an efficient method towards new (benzimidazoyl)piperazines with high affinity for the 5-HT1A receptor." Tetrahedron, vol. 56, No. 20, pp. 3245-3253, 2000.

Lopez-Rodirgues et al, "Synthesis of new (benzirnidazoyl) piperazines with affinity for the 5-HT1A receptor via Pd(0) animation of bromobenzimidazoles." Bioorganic and Medicinal Chemise Letters, vol. 9, No. 16, pp. 2339-2342, 1999.

Lopez-Rodriguez et al., "Benzimidazole derivatives. Part 5." Bioorganic & Medicinal Chemis., vol. 12, No. 19, pp. 5181-5191, 2.004.

Lopez-Rodriguez et al., "Synthesis and Structure-Activity Relationships of a new Model of Arylpiperazines. 8." Journal of Medicinal Chemise, vol. 48, No. 7, pp. 2548-2558, 2005.

Madden et al., "Clinical management of aggression." Multidisciplinary approaches to aggression research. Brain and Benton -(Eds.), pp. 477-488, 1981.

Malick, JB. "The pharmacology of isolation-induced aggressive behaviour in nu e." Curr. Dev. Psvchopharmacol., vol. 5. pp. 1-27, 1979.

Malmnas, CO. "Monoaminergic influence on testerone-activated copulatory behavior in the castrated male rat." Acta Physiol. Scand., vol. 395S, pp. 1-128, 1973.

Marini et al., "On the specificity of a cat behavior model for the study of hallucinogens." Eur. J. Pharmacal. vol. 70, pp. 479-487, 1981.

McCance et al. "The effect of metergoline on endocime responses to L-tryptophan." Psychopharmacology, vol. 2, pp. 90-94, 1987.

McCann et al., "Peptidergic and dopaminergic control of prolactin release." Trends Pharmacol. Sci., pp. 127-131, 1984.

McCreary et al, "SLV308: a novel antiparkinsonian agent with antidepressant and anxiolytic properties." Solva Pharmaceutical Conferences, vol. 1, pp. 51-58, 2002.

McGlone et al., "Lithium and porcine aggression." J. Anim. Sci., vol. 51, pp. 447-455, 1981.

Meltzer et al., "Effect of buspirone on prolactin and growth hormone secretion in laboratroy rodents and man." J.Clin. Psychiatry, vol. 43, pp. 12 sec. 2, 1982.

Metysova et al., "Pharmakologische Eigenschaften der 6,11-Dihydrodibenz (b,c) thiepin Derivate." ArzneimForsch, vol. 13, pp. 1039-1043, 1963.

Mewshaw et al., "New generation dorninergic agents," Bioorganic and Medicinal Chemistry Letters, vol. 8, No. 19, pp. 2675-2680, 1998.

Miczek et al. "Drug effects on agonistic behavior." Advances in behavioural pharmacology vol. 2., pp. 87-162, 1979.

Miczek et al., "Mharmacological analysis of attack and flight." Multidisciplinary approaches to aggression research. Brain and Benton (Eds.), pp. 341-354, 1981.

Miczek et al., << Pharmacological, hormonal and behavioral manipulations in the analysis of aggressive behavior.>> Ethopharmacological Aggression Research. Miczek, Kruk and Olivier, (Eds.), pp. 1-16, 1984.

Miczek, et al., "Pharmacology of sex and aggression." Behavioral Pharmacology, Glick and Goldfarb (Eds.), pp. 176-257, 1976.

Miczek, KA. "A new test for aggression in rats without aversive stimulation: Differential effects of d-amm hetamine and cocaine." Psychopharmacology, vol. 60, pp. 253-259, 1979.

Miczek, KA. "Intraspecies aggression in rats: effects of d-amphetamine and chlordiazeepoxide."Psychopharmacology, vol. 39, pp. 275-301, 1974.

Miczek, KA., "The psychopharmacology aggression." Handbook of Psychopharmacology: vol. 19, Behavioral Pharmacology, Iversen, Iversen and Snyder (Eds.), pp. 183-327, 1987.

Middlerniss et al., "8-hydroxy-2(di-n-propylamino) tetralin discriminates between subtypes of the 5-HT recognition sites," Eur. J. Pharmacol., vol. 90, pp. 151-153, 1983.

Millan et al, "Novel benzodioxopiperazines acting as antagonists at postsynaptic 5-HT 1A receptors and as agonists at 5-HT1A autoreceptors: a comparitive pharmacological characterization with proposed 5-HT1A antagonists." J Pharmacology and Experimental Therapeutics, vol. 268, No. 1, pp. 337-352, 1994.

Millan et al. "Pro- and anticocieptive actions of serotonin (5-HT)1A agonists and antagonists in rodents: Relationship to algesiometric paradigm." Behavioural Brain Research, vol. 73, No. 1/2, pp. 69-77, 1995.

Millan et al, "S 15535, A novel bnezodioxopiperazine ligand of sertonin (5-HT)1A receptors: I. Interaction with cloned human (h)5-HT 1A, dopamine hD2/hD3 and ha 2A- adrenergic receptors in relation to modulation of cortical monoamine release and activity in models of potential antidepressant activity." J. Pharmacology and Experimental Therapeutics, vol. 282, No. 1, pp. 132-147, 1997.

Millan et al, "S 15535: a highly selective benzodioxopiperazine 5-HT1A receptor ligand which acts as an agonist and an antagonist at presynaptic and postsynaptic sites respectively." European J. Pharmacology, vol. 230, No. 1, pp. 99-102, 1993.

Millan et al, "Serotonin and pain: Evidence that activation of 5-HT 1A receptors does not elicit antinociception against noxious thermal, mechanical and chemical stimuli in mice." Pain, vol. 58, No. 1, pp. 45-61, 1994.

Millan et al, "The serotonin IA receptor partial agonists S15535 [4-(benzodioxan-5-yl)1-(indan-2-yl)piperazine] enhance cholinergic transmission and cognitive function in rodents: a combined neurochemical and behabioral analysis." J. Pharmacology and Experimental Therapeutics, vol. 311, No. 1, pp. 190-203, 2004.

Minnema et al., "Antinociceptive comparison of quipazine and morphine." Commun. Psychopharm., vol. 4, pp. 115-120, 1980.

Miyamoto et al., "Metabolism of a new positive inotropic agent, 3,4-dihydro-6-[4-(3,4-dimethoxybenzoyl)-1-piperazinyl]-2(1H)-quinolinone (OPC-8212) in the rat, mouse, dog, monkey and human." Xenobiotica, vol. 18, pp. 1143-1155, 1988.

Modica et al, "[[(Arylpiperazinyl)thieno][2,3-d]pyrimidinone derivatives as high-affinity affinity selective 5-HT 1A receptor ligands." J. Medicinal Chemistry, vol. 40, No. 4, pp. 574-585, 1997.

Mokrosz et al, "Structure relationship studies of CNS agents. Part 14: structural requirements for the 5-HT1A and 5-HT2A receptor selectivity of simple 1-(2-pyrimidinyl)piperazine derivatives." Pharmazie, vol. 49, No. 11, pp. 801-806, 1994.

Molewijk et al, "Conditioned ultrasonic distress vocalizations in adult male rats as a behavioral paradigm for screening anti-panic drugs." Psychopharmacology, vol. 117, No. 1, pp. 32-40, 1995.

Monroe, RR. "Anticonvulsants in treatment of aggression." 7. Nerv. Mental Disease, vol. 160, pp. 119-126, 1975.

Monroe, RR. "Drugs in the management of episodic behavioral disorders." Neural bases of violence and aggression. Fields and Sweet, (Eds.), pp. 328-348, 1975.

Mos et al., "Differential effects of selected psychoactive drugs on dominant and subordinate male housed in a colony." Neuroscience Research Communications, vol. 2, No. 1, pp. 29-36, 1988.

Mos et al., "Different test situations for measuring offensive aggression in male rats do not result in the same wound patterns." Physiol. Behav., vol. 32, pp. 453-456, 1984.

Mos et al., "Ethopharmacological analysis of the pro-aggressive action of low doses of benzodiazepines in rats." Psychopharmacology), vol. 89, pp. 25, 1986.

Mos et al., "Postpartum aggression in rats does not influence threshold currents for EBS- induced induced aggression." Brain Res. vol. 404, pp. 263-266, 1987.

Mos et al., "RO 15-1188 does not influence postpartum aggression in lactating famale rats."Psychopharmacology, vol. 90, pp. 278-280, 1986.

Moyer, KE. "Kinds of aggression and their physiological basis." Comm. Behav. Biol., pp. 65-87, 1968.

Mueller et al. "Further studies of the putative serotonin agonist m-chlorophenylpiperazine: evidence for a serotonin receptor mediated mechanism of action in humans." Psychopharmacology, vol. 89, pp. 388-391, 1986.

Muhlbauer, HD. "Human aggression and the role of central serotonin." Pharmacopsychiatria, vol. 18, pp. 218-221, 1985.

Mulder et al., "Calcium-dependent release of radiolabeled catecholamines and serotonin from rat brain synaptosomes in a superfusion system." Brain Res., vol. 99, pp. 419-424, 1975.

Muller et al., "Strychnine binding associated with synaptic glycine receptors in rat spinal cord membranes: ionic influences." Brain Res., vol. 147, pp. 101-116, 1978.

Muraoka et al., "The effects of DU 27716 on aggression and social behaviour in the rat." Aggr. Behav., vol. 9, p. 118, 1989.

Murphy et al., "Comparative anxiognic neuroendocrine and other physiological effects of m-chlorophenylpiperazine given intravenously or orally to healthy volunteers." Psychopharmacology, vol. 98, pp. 275-282, 1989.

Murphy et al., "Comparative anxiogenic, neuroendocrine and other physiological effects of m-chlorophenylpiperazine given intravenously or orally to healthy volunteers." Psychopharmacology, vol. 98, pp. 275-282, 1989.

Newman-Tancredi et al, "Agonist and inverse agonist efficacy at human recombinant serotonin 5-HT1A receptors as a function of receptor:G-protein stoichiometry." Neuropharmacology, vol. 36, No. 4/5, pp. 451-459, 1997.

Newman-Tancredi et al, "Antibody capture assay reveals bell-shaped concentration-response isotherms for H5-HT1A receptor-mediated $G\alpha$ i3 activation: Conformational selection by high-efficacy agonists, and relationship to trafficking of receptor signaling." Molecular Pharmacology, vol. 62, No. 3, pp. 590-601, 2002.

Newman-Tancredi et al, "Comparison of hippocampal G protein activation by 5-HTJA receptor agonists and the atypical antipsychotic clozapine and S 16924." Naunyn-Schrniedeber's Archives of Pharrnacology vol. 368, No. 3, pp. 188-199, 2003.

Newman-Tancredi et al, "Differential modulation by GTPγS of agonist and inverse agonist binding to h5-HT1A receptors revealed [Z3H-WAY] 00,635." British J. Pharmacology, vol. 132, No. 2, pp. 518-524, 2001.

Newman-Tancredi et al, "Labeling of recombinant human and native rat serotonin 5-HT 1A receptors by a novel, selective radioligand, [3H]-S15535: Definition of its binding profile using agonists, antagonists and inverse agonists." Naunyn-Schmiedeberg's Archives of Pharmacology, vol. 357, No. 3, pp. 205-217, 1998.

Newman-Tancredi et al, "S 15535 and WAY 100, 635 antagonize 5-HT-stimulated [35S]GTPγs binding at cloned human 5-HT1A receptors." European J. Pharmacology, vol. 307, No. 1, pp. 107-111, 1996.

Newman-Tancredi et al, "The 5HT1A receptor ligand, S15535, antagonizes G -protein activation: a [35S]GTPγS and [3H]S15535 autoradiography study." European J. Pharmacology, vol. 384, No. 2/3, pp. 111-121, 1999.

Nikulina et al., "Serotonin's influence on predatroy behavior of highly aggressive CBA and weakly aggressive DD strains of mice." Aggressive Behavior, vol. 12, pp. 277-283, 1986.

Nilsen, L. "Studies on algesimetry by electrical stimulation of the mouse tail." Acta. Phannacol. Toxicol., vol. 18, pp. 10-22, 1961.

O'Neil et al., "Tryptophan-trazodone treatment of aggressive behavior." Lancet, vol. 2, pp. 859-860, 1986.

Oficialdegui et al, "Design, synthesis and biological evaluation of new 3-[(4-aryl)piperazin-1-yl]-1-arylpropane dervaties as potential antidepressants with a dual mode of action; serotonin reuptake inhibition and 5-HT1A receptor antagonism." Farmaco, vol. 55, No. 5, pp. 345-353, 2000.

Olivier et al, "Behavorial Pharmacology of the serenic, eltoprazine." Drug Interactions, vol. 8, No. 1-2, pp. 32-83, 1990.

Olivier et al, "Serenics: an introduction." Drug Metabolism and Drug Interactions, vol. 8, No. 1-2, pp. 1-9, 1990.

Olivier et al, "Serotoneric modulation of social interacation in isolated male mice." Psychopharmacology, vol. 97, No. 2, pp. 154-156, 1989.

Olivier et al, "Ultrasonic vocalizations in rat pups: effects of serotonergic ligands." Neuroscience and Biobehavioral Reviews, vol. 23, No. 2, pp. 215-227, 1.998.

Olivier et al. "Serotonergic modulation of social interactions in isolated male mice." Psychopharm, vol. 97, pp. 154-156, 1989.

Olivier et al., "Animal models of anxiety and aggression in the study of serotonergic agents." Sertonio subtypes: pharmacological significance and clinical implications. Int. Acad. Biomed. Drug Res., vol. 1, Langer, Brunello, Racagni and Mendlewicz (Eds.), pp. 67-79, 1992.

Olivier et al., "Behavioral effects of psychoactive drugs on agonistic behavior of male territorial rats (resident-intruder model)." Ethopharmacological Aggression Research, Miczek, Kruk and Olivier (Eds.), pp. 137-156, 1984.

Olivier et al., "Effect of anterior hypothalamic and mammillary area lesions on territorial aggressive behaviour in male rats." Behav. Brain Res., vol. 9, pp. 59-81, 1983.

Olivier et al., "Effects of a new psychoactive drug (DU 27716) on different models of rat agonistic behaviour and EEG." Biological Perspectives on aggression. Blanchard, Flannelly, and Blanchard, (Eds.), pp. 261-279, 1984.

Olivier et al., "Maternal aggression in rats: Effects of chlordiazepoxide and fluprazine." Psychopharmacol., vol. 86, pp. 68-76, 1985.

Olivier et al., "Maternal aggression in rats: Lack of interaction between chlordiazepoxide and fluprazine." Pschychopharmacology, vol. 88, pp. 40-43, 1986.

Olivier et al., "Serotonergic aspects of agonistic behavior." New Directions in affective disorders. Lerer and Gershon (Eds.), pp. 40-44, 1989.

Olivier et al., "Serotonergic involvement in aggressive behaviour in animals." Violence and suicidality: perspectives in clinical and psychobiological research. VanPraag, Plutchik and Apter (Eds.), pp. 79-137, 1990.

Olivier et al., "Serotonergic receptors in anxiety and aggression: Evidence from animal harmacolo3." Human Psychopharmacology, vol. 6, talcs S73-78, 1991.

Olivier et al., "Serotonin and Aggressive behaviour in rat." Psychopharmacology, vol. 89, p. 26, 1986.

Olivier et al., "Social behavior in rats and mice: An ethologically based model for differentiation psychoactive drugs." Aggr. Behav., vol. 8, pp. 163-168, 1982.

Olivier, B. "The ventromedial hypothalamus and aggressive behaviour in rats." Aggr. Behav., vol. 3, pp. 47-56, 1977.

Olivier, B., "Selective anti-aggressive properties of DU27725: Ethological analysis of intermale and territorial aggression in the male rat." Pharmacol. Biochem Behav., vol. 14 (suppl 1) pp. 61-77, 1981.

Ortmann, R. "The 5-HT syndrome in rats as tool for the screening of psychoactive drugs." Drug Dev. Res., vol. 4, pp. 593-604, 1984.

Orus et al., "Synthesis and Molecular Modeling of New 1-Aryl-3-4-arylpiperazin 1-yl-1- propane Derivatives with High Affinity at the Serotonin Transporter and at 5-HT1A Rece.tors," Journal of Medicinal Chemist, vol. 45, No. 45, No. 19, pp. 4128-4139, 2002.

Owen, RT. "YG-19-2S6." Drugs of the Future, vol. 5, pp. 98-99, 1980.

Panksepp et al., "The psychobilology of play: Theoretical and methodological perspectives." Neurosci. Biobehav. Rev., vol. 8, pp. 465-492, 1984.

Payne et al., "Agonistic behaviour between pairs of hamsters of same and opposite sex in neutral observation area." Behaviour, vol. 36, pp. 259-269, 1970.

Pazos et al. Brain Research, vol. 346, pp. 205-230, 1985.

Pcglion et al., "Characterization of potent and selective antagonists as postsynaptic 5-HT1A receptors in a series of N4-substituted arylpiperazines." J. Medicinal Chemistry, vol. 38, No. 20, pp. 4044-4055, 1995.

Peroutka et al. "Modulation of neuronal activity in the hippocampus by 5-hydroxytryptamine and 5-hydroxytryptamine1A selective drugs." Neurophaarmacology, vol. 26, pp. 139-146, 1987.

Perrone et al, Trans-4-[4-(methoxypbenyl)cyclohexyl]-1-arylpiperazines: a new class of potent and selective 5-HT1A receptor ligands as conformationally constrained analogues of 4-[3-[5-methoxy-1,2,3,4-tetrahydronaphthalen-1-yl)propyl]Z-1-arylpiperazines. J. Medicinal Chemistry, vol. 44, No. 25, pp. 4431-4442, 2001.

Petrie et al., "Violence in geriatric patients." JAMA, vol. 248, pp. 443-444, 1982.

Pfaff et al., "Film analyses of lordosis in female rats." Hor. Behav., vol. 5: 317-335, 1974.

Porter et al., "Azaperone: a review of a new neuroleptic for swine." Vet. Med., pp. 88-92, 1985.

Potegal et al., "Effects on muricide of DU 27716 injected peripherally or into septum or dorsal raphe." Aggr. Behav., vol. 9, pp. 118, 1983.

Potegal, M. "The reinforcing value of several types of aggressive behavior: a review." Aggr. Behav., vol. 5, pp. 353-373, 1979.

Rabiner et al, "5-Hydroxytryptaminc 1A receptor occupancy by novel full antagonist 2-[4-[-(7-chloro-2,3-dihydro-1,4-benzdioxy-5-yl)-1 -piperazinyl]buty1]-1,2-benzisothiazol-3-(2H)- one-1,1-dioxide: A [11C][ 0-methy1-3H]-n-(2-(4-(2-methoxypbenyl)-1-piperaziny1)ethy1)-N- (2-pyridinyl) cyclohexacarboxanude trihydrochloride (WAY-100635) positron emission tomography study in humans." J. Pharmacology and Exp. Therapeutics, vol. 301, No. 3, pp. 144-1150, 2002.

Rabiner et al, "Drug action of the 5-HT 1A receptor invivo: autoreceptor and postsynaptic receptor occupancy examined with Pet and [carbonyl-11 C] Way-100635." Nuclear Medicine and Biology, vol. 27, No. 5, pp. 509-513, 2000.

Racine et al., "Anti-aggressive effects of DU 27716 on attack and defensive behaviours in male mice." Biological perspectives on Aggression. Flannclly, Blanchard and Blanchard, (Eds.), pp. 281-293, 1984.

Raleigh et al., "Serotonergic influences on the social behavior of vervet monkeys (*Cercopithecus gethiops subaeus*)." Exp. Neurol., vol. 68, pp. 322-339, 1980.

Raleigh et al., "Social and environmental influences on blood serotonin concentrations in monkeys." Arch. Gen. Psychiatry, vol. 41, pp. 405-410, 1989.

Ratey et al. "Autism: the treatment of aggressive behaviors." J. Clin. Psychopharmacology, vol. 7, pp. 35-41, 1987.

Reisberg et al., "Behavioral symptoms in alzheimer's disease: phenomenology and treatment." J. Clin. Psychiatry, vol. 48(Suppl. 5), pp. 9-15, 1987.

Risse et al. Pharmacologic treatment of agitation associated with dementia. Jags, vol. 34 pp. 368-376, 1986.

Rodgers, RJ. "Drugs, aggression and behavioural methods." Multidisciplinary approaches to aggression research. Brain and Benton, (Eds.), pp. 325-340, 1981.

Rodger, RJ. "Effects of nicotine, mecamylamine and hexamethomium on shock induced fighting, pain reactivity and locomotor behaviour in rats." Psychopharmacologia, vol. 66, pp. 93-99, 1979.

Rodgers, RJ. "Neurochemical correlates of aggressive behaviour: Some relations to emotion and pain sensitivity." Chemical influences on behaviour. Brown and Cooper, (Eds.) pp. 374-419, 1979.

Rossi, AC. "The "mouse-killing" rat: ethological discussion on an experimental model aggression." Pharmacol. Res. Commun., vol. 7, pp. 199-2 16, 1975.

Roubicek et al., "YG 19-256: EEG and clinical study in aggressive oligophrenics." Psychopharmacologia (Bert.) vol. 26 (suppl.), p. 71, 1972.

Roy et al. "Suicidal behavior, impulsiveness and serotonin." Acta Psychiatry Scandinavia, vol. pp. 529-535.

Rupniak et al., "Acute dystonia induced by neuroleptic drugs." Psychopharmacology, vol. 88, pp. 403-419, 1986.

Rusterholz et al., "Serotonergic and dopaminergic involvement in the mechanism of action of R (-)-2,5-Dimethoxy-4-bromo-amphetamine (DOB) in cats." Life Sci., vol. 23, pp. 1499-1506, 1978.

Sachs et al., "Functional analysis of masculine copulatory behaviour in the rat." Adv. Study Behav., vol. 7, pp. 91-154, 1976.

Samanin R, Bemasconi S, Quattrone A. Antinociceptive action of quipazine; relation to central serotonergic receptor stimulation. Psychopharmacology, vol. 41, pp. 219-222, 1976.

Sanger et al., "Differential effects of morphine on food and water intake in food deprived and freel feeding rats." Psychopharmacology, vol. 72, pp. 103-106, 1980.

Sanger et al., "The anorectic properties of opiate antagonists." Drug Devi. Res., vol. 3, pp. 137-142, 1983.

Sarteschi et al., "Pathological aggressiveness in man: some theoretical and practical considerations." Mod. Probl. Pharmacopsychiatry, vol. 13, pp. 159-174, 1978.

Sbordone et al., "An ethological analysis of drug-induced pathological aggression," Multidisciplinary approaches to aggression research. Brain and Benton, (Eds.), pp. 369-385, 1981.

Schipper et al, "Neurochemical profile of eltoprazine." Drug Metabolism and Drug Interactions, vol. 8, No. 1-2, axes 85-114, 1990.

Schipper et al, "Preclinical pharmacology of flesinoxan: a potential anxiolytic and antidepressant drug." Human Psychopharmacology, vol. 6 (suppl), pp. S53-S61, 1991.

Schreiber et al., "5-HT1A receptor ligands in animal models of anxiety, impulsivity and depression: multiple mechanisms of action." Prog. Neuro-Psychopharmacol. & Biol. Psychiat., vol. 17, pp. 87-104, 1993.

Schultz et al., "Prey-dependent effects of fluprazine hydrochloride on predatory aggression in northern grasshopper mice (Ony chomys leucogaster) and rats (Rattus norvegicus)." Aggr., vol. 89, pp. 267-275, 1986.

Scott, JP. "Agonistic behaviour in mice and rats: a review." Am. ZooL, vol. 6, pp. 683-701.

Sheard et al. "The effect of lithium on impulsive aggressive behaviour in man." American Journal of Psychiatry, vol. 133, pp. 1409-1413, 1976.

Sheard et al., "Psychopharmacology of aggression in humans." Ethopharmacology of agonistic behavior in animals and humans. Olivier, Mos and Brain (Eds.), pp. 257-266, 1987.

Sheard, MM. "Clinical Pharmacology of aggressive behavior." Clinical Neuropharmacology, vol. 7,173-183, 1984.

Shenker et al., "Peripheral serotonin2 receptor blockade does not inhibit 5- hydroxytryptophan-induced aldostcrone stimulation." J. Clin. Endocrinol & Metabolism, vol. 61, pp. 1201-1204, 1985.

Siderius, P. "Broncholytic effects of dl-N-tert.butyl arternol and 2-(O-methoxyphenyl) iso'ro• 1 meth lamine." Acta. Ph siol. Pharmacol. Neerl., vol. 2. pp. 546-552, 1952.

Sidman, M., "Behavioural pharmacology." Psychopharmacologia, vol. 1, pp. 1-19, 1959.

Sijbesma et al, "Eltoprazine, a drug which reduces aggressive behavior, binds selectively to 5-HT 1 receptor sites in the rat brain: an autoradiographic study." European J, Pharmacology, vol. 177, No. 1-2 pp. 55-66, 1990.

Sijbesma et al, "The anti-aggressive drug eltoprazine preferentially binds to 5-HT1,A and 5- HT 1B receptor subtypes in rat brain: sensitivity to guanine nucleotides." European J. Phannacolo -3, vol. 187 No. 2 pp. 209-223, 1990.

Sills et al., "Determination of selective and non-selective compounds for the 5-HT and 5- HT1B receptor subtypes in rat frontal cortex." J. Pharmacol. Exp. Ther., vol. 231, pp. 480-487, 1984.

Silver et al., "Aggressive behavior in patients with neuropsychiatric disorders. Special Issue: Treatment of aggressive disorders." Psychiatric-Annals, vol. 17, No. 6, pp. 367-370, 1987.

Silverman, AP. "Ethological and statistical analysis of drug effects on the social behaviour of laboratory rats." Br. J. Pharmacol., vol. 24, pp. 579-590, 1965.

Silverman, AP. "The social behaviour of laboratory rats and the chlorpromazine and other drugs." Behaviour, vol. 27, pp. 1-38, 1966.

Simantov et al., "The opiate receptor binding interactions of (3H) methionine enkephalin, an opioid peptide." Eur. J. Pharmacol., vol. 47, pp. 319-331, 1978.

Simonovic et al. "Effect of 8-hydroxy-2-(di-n-propylamino) tetralin on rat prolactin secrction." J,Ncural. Transmission, vol. 59, pp. 143-149, 1984.

Sleight et al, "Identification of 5-hydroxytryptamine I A receptor agents using a composite pharmacophore analysis and chemical data base screening." Naunyn-Schmiedeberg's Archives of Pharmacology, vol. 343, No. 2, pp. 109-116, 1991.

Smith DR, "Lithium, animal behaviour and monoamines: five questions and possible ways of answering them." Acta Pharmacol. Toxicol., vol. 56, pp. 198-202, 1985.

Smith et al., "Critical flicker frequency (CFF) and psychotropic drugs in normal human subiects. a review." Psychonhvsioloav. vol. 47, napes 175-182, 1976.

Sodersten et al., "Sexual behaviour in castrated male rats treated with monoamine synthesis inhibitors and testosterone." Pharmacol. Biochem. Behav., vol. 5, pp. 319-327, 1976.

Stockmeyer et al., "A Strong influence of serotonin axons on b-adrenergic receptors in rat brain." Science, vol. 230, pp. 323-325, 1985.

Stoof et al., "Opposing roles for 0-1 and D-2 dopamine receptors in efflux on c-AMD from rat neostria turn." Nature, vol. 294, pp. 366-368, 1981.

Sulser. F. "Deamplifcation of noradrenergic singnal hamper by antidepressants. A unified catecholamine-serotonin hypothesis of affective disorders." Psychopharm. Bull., vol. 19, pp. 300-304, 1983.

Svare et al., "Hormonal influences on maternal agression." Hormones and aggressive behaviour. Svare, (Ed.), pp. 91-104, 1983.

Svare et al., "Mice: Sucking stimulation but not lactation important for maternal aggression." Behav. Neural. Biol., vol- 29, pp. 453-462, 1980.

Svare et al., "Postpartum agression in mice: experimetal and envirronmental factors." Horm. Behav. vol. 4, pp. 323-334, 1973.

Svare, B. "Maternal aggression in mice: influence of the young." Biobehav. Rev., vol. 1, pp. 15 1-164, 1977.

Svare, B. "Models of aggression employing female rodents." The Biology of aggression. Brain and Benton, (Eds.), pp. 503-508, 1981.

Symoens et al., "Prevention and cure of aggressiveness in pigs using the sedative azaperone." Vet. Rec. vol. 85, pp. 64-77, 1969.

Takahashi et al., "Intermale and maternal aggression in adult rats tested at different ages." Physiol. Behav., vol. 29, pp. 1013-1018, 1982.

Tardiff et al., "Assault, suicide and mental illness." Arch. Gen. Psychiatry, vol. 73, pp. 164-169, 1980.

ardiff et al., "Assaultive behavior among chronic inpatients." Am. J. Psychiatry, vol. 139, pp. 212-215, 1982.

Tardiff, K. "Charactistics of assaultive patients in private hospitals." American Journal of Psychiatry, vol. 141, pp. 1232-1235, 1984.

Taylor et al., "Pharmacological and clinical effects of buspirone." Pharmacol. Biochem. Behav., vol. 23, pp. 687-694, 1985.

Taylor et al., "Preparation of 3H-[3-Me-His21] as an improved ligand for TRH receptors." Neuroendocrinology, vol. 32, pp. 310-316, 1981.

Teceschi et al., "Effect of various centrally acting drugs of fighting behaviour of mice." J. Pharmacol. Ex.. Ther., vol. 125, pp. 28-34 1959.

Teitler et al, "5-HT 1 A sertonin receptor binding: a preliminary structure-affinity investigation." Medicinal Chemist Research vol. 7, No. 4, pp. 207-218, 1997.

Terlecki et al., "Conditioned and unconhitioned defensive burying in the rat." Learn Motivation, vol. 10, pp. 337-350, 1979.

Testa et al, "Effect of serveral 5-hydroxytryptamine 1A receptor ligands on the micturition reflexi n rats: comparison with Way 100635." J. Pharmacology and Experimental Thera.eutics, vol. 290, pp. 1258-1269, 1999.

Thompson, T., "Behavioural mechanisms of drug dependence." Advances in behavioural pharmacology, vol. 4. Thomson Dews and Barrett (Eds.), pp. 1-45 1984.

Thor et al., "Sex-eliciting behavior of the female rat: discrimination of receptivity by anosmic and intact males." Behav. Biol., vol. 23, pp. 326-340, 1978.

Tran et al., "Histamine HI receptors identified in mammalian brain membranes with (3H) me, amine." Proc. Natl. Acad Sci. U.S.A., vol. 75, pp. 6290-6294, 1978.

Traskman et al., "Monoamine metabolites in CSF and suicidal behavior." Arch. Gen. Ps chia', vol. 38, pp. 631-636, 1981.

Treit et al., "Conditioned Defensive Burying: a new paradigm for the study of anxiolytic agents." Pharmacol. Biochem. Behav., vol. 15, pp. 619-626, 1978.

Treit et al., "The inhibitory effect of diazepam on conditioned defensive burying is reversed by picrotoxin." Pharmacol. Biochem. Behay., vol. 17, pp. 359-361 1982.

Treit, D. "Animal models for the study of anti-anxiety agents: a review." Neurosci. Biobehav. Rev., vol. 9, pp. 2033-2222, 1985.

Tricklebank, MD. "The behavioural response to 5-HT receptor agonists and subtypes of the central 5-HT receptor." Trends Pharmacol. Set., pp. 403-407, 1985.

Trimble, M. "New antidepressant drugs and the seizure threshold." Neuropharmacology, vol. 19, pp. 1227-1228, 1980.

Trimble, M. "Non-monoamine oxidase inhibitor antidepressants and epilepsy: a review." Epilepsia, vol. 10, pp. 241-250. 1978.

Trulson et al., "Behavioural effects of quipazine in the cat." Eur. J. Pharmacol., vol. 78, pp. 295-305, 1982.

Trulson et al., "Chronic administration to cats: behavioural and neurochemical evidence for decreased central serotonergic function." J. Pharmacol. Exp. Therap., vol. 211, pp. 375-384, 1979.

Tu et al. The eastern Ontario Survey: A study of drug-treated psychiatric problems in the mentally handicapped. Canadian J. Psychiatry, vol. 28, pp. 270-276, 1983.

Tupin, JP. "Psychopharmacology and aggression." Clinical treatment of the violent person. Roth LH, (Ed.), pp. 83-99, 1985.

Tyrer et al. Factors associated with a good response to lithium in aggressive mentally handicapped subjects. Prog. Neuro. Psychopharmacol and Biol. Psychiatry, vol. 8, pp. 751-755, 1984.

Ulrich et al., "Reflexive fighting in response to aversive stimulation." J. Exp. Anal. Behav., vol. 5, pp. 511-520, 1962.

U'Prichard et al., "In vitro modulation of CNS B-receptor number by antidepressants and B- agonists." Eur. J. Pharmacol., vol. 59, pp. 297-301, 1979.

U'Prichard et al., "Building characteristics of a radiolabelled agonist and antagonist at central nervous system alpha noradrenergic receptors." Mol. Pharmacol., vol. 13, pp. 435-473, 1977.

Ursin, H. "Aggression and the brain: reflex chains or network?" Behav. Brain. Sci., vol. 2, p. 227, 1979.

Ursin, H. "Neuroanatomical basis of aggression." Multidisciplinary approaches to aggression research. Brain and Benton, (Eds.), pp. 269-293, 1981.

Valzel li, L. "Effects of sedatives and anxiolytics on aggressivity." Modern problems of pharmacology of anxioltyics and sedatives. Boissier, (Eds.) pp. 143-156, 1979.

Valzelli et al., " Psychoactive drug effect on socio-environmental deprivation in rats." Pharmacol. Res Commun., vol. 12, pp. 279-282, 1980.

Valzelli, L. "Aggressive behaviour induced by isolation." Aggressive Behav., pp. 70-76, 1969.

Valzelli, L. "Reflections on experimental human pathology of aggression." Prog. Neuro-Psychopharmacol. And Biol. Psychiatry, vol. 8, pp. 311-325, 1984.

Valzelli, L. "The "isolation syndrome" in mice." Psychopharmacologia, vol. 31, pp. 305-320, 1973.

Valzelli, L., "Psychopharmacology of aggression: an overview." Intl. Pharmacopsychiatry, vol. 16, pp. 39-48, 1981.

Van de Kar et al, "Effect of selective scrotonin (5HT) agonists and 5HT2 antagonist on .rolactin secretion." Neuropharmacology, vol. 28, pp. 299-305, 1989.

Van de Poll NE et al., "Effects of fluprazine (DU 27716) upon aggressive and sexual behaviour of testosterone-treated female rats," Aggr. Behav, vol. 12, pp. 293-301, 1986.

Van dar Poel AM et al., "A motivational analysis of ambivalent actions in the agonistic behaviour of rats in tests used to study the effects of drugs on aggression." Ethopharmacological Aggression Research. Miczek, Kruk and Olivier, (Eds.), pp. 115-135, 1984.

Van der Poel AM et al., "Anti-aggressive effect of a new phenylpiperazine compound (DU 27716) on hypothalamically induced behavioural activities." Pharmacol. Biochem. Behav., vol. 17, pp. 147-153, 1982.

Van Leeuwen et al., "Assessment of the antiaggressive effects of a putative anxiolytic, GCP 361A, versus those of diazepam and placebo in humans using a novel experimental approach." Psychopharmacology, vol. 96, No. 232, p. 5358. 1988.

Van Praag. HM. "Depression, suicide and metabolites of serotonin in the brain." J. Affect Disorders, vol. 4, pp. 275-290, 1982.

Vergnes et al., "Effect of hypothalamic injections of 5,7-dihydroxytryptamine on elicitation of mouse-killing in rats." Behav. Brain Res., vol. 5, pp. 387-397, 1982.

Vergnes et al., "Parachloro-phenylalanine-induced serotonin depletion increases offensive but not defensive aggression in male rats." Physiol. Behav., vol. 36, pp. 653-658, 1986.

Vergnes et al., "Selective increase of offensive behavior in the rat following intrahpothalamic 5,7-DHT-induced serotonin depletion." Behav. Brain. Res., vol. 29, pp. 85-91, 1988.

Villimem et al. "CSF monoamine metabolites in male arsonists." Arch. Gen. Psychiatry, vol. 44, pp. 241-247, 1987.

Willner et al., "Subchronic treatment with the tricyclic antidepressant DMI increases isolation-induced fighting in rats." Pharmacol. Biochem. Behav., vol. 14, pp. 475479, 1981.

Winslow et al., "Alcohol effects on the aggressive behaviour of squirrel monkeys and mice are modulated by testosterone." Ethopharmacology of agonistic behaviour in animals and man. Olivier, Mos and Brain, (Eds.), 1987.

Wise, DA. "Aggression in the female golden hamster: effects of reproductive state and social isolation." Horm. Behav. val. 5, pp. 235-250, 1974.

Wolf et al, "SLV-308(Solvay)" Current Opinion in Investigational Drugs, vol. 4, No. 7, pp. 878-882,2003.

Worrall et al. "Lithium in Non-manic depressives: antiaggressive effect and red blood cell lithium values." British Journal of Psychiatry, vol. 126, pp. 464-468, 1975.

Wouters et al, "Plesinoxan lowers blood pressure and heart rate in cats via 5-HT1A rece.tors." European J. Pharmacology, vol. 149, No. 3, pp. 213-223, 1988.

Yamamura et al., "Muscarinic cholinergic binding in rat brain." Proc. Nat. Acad. Sci. U.S.A., vol. 71, pp. 1725-1729, 1974.

Yatham et al. Carbamazepine in the treatment of aggression: a case report and review of the literature. Acta Psychiatry Scandinavia, vol. 78, pp. 188-190, 1988.

Yen et al., "Ataracitc suppression of isolation-induced aggressive behavior." Arch. Intl. Pharmacod Ther., vol. 123, pp. 179-185, 1959.

Yodyingyuad et al., "Relationship between dominance hierarchy, cerebrospinal fluid levels of amine transmitter metabolites (5-hydroxyindole acetic acid and homovanillic acid) and plasma cortisol in monkeys." Neurosci., vol. 16, pp. 851-858, 1985.

Yudofsky et al. "harmacologic treatment of aggression. Special Issue: Treatment of aggressive disorders." Psychitric-Annals. vol. 17, No. 6, pp. 397-407. 1987.

Ratey et al., "The Psychopharmacology of Aggression, Toward a New Day", Psychopharmacology Bulletin , vol. 29, No. 1, pp. 65-73, 1993.

Baumgarten et al., "Psychopharmacology of Central Serotonergic Systems", Pharmacopyschiatry, vol. 28, No. 2, pp. 73-79, 1995.

Gibert-Rahola, "Treatment of Impulse Control Disorders", European Neuropsychopharmacology, vol. 3, No. 3, pp. 272-273, 1993.

Griebel et al., "Serenics Fluprazine (DU 27716) and Eltoprazine (DU 28853) Ehance Neophobic and Emotional Behaviour in Mice", Psychopharmacology, vol. 102, No. 4, pp. 498-502, 1990.

Olivier et al., "Behavioural Pharmacology of the Serenic, Eltoprazine", Drug Metabolism and Drug Interactions, vol. 8, No. 1-2, pp. 31-83, 1990.

U.S. Appl. No. 10/199,634, field Jul. 19, 2002, Daniela Brunner, et al.

J. Gibert-Rahola, Treatment of Impulse Control Disorders, European Neuropsychopharmacology, 1993, vol. 3, No. 3, pp. 272-273.

Nippon Nogeikagaku Kaishi, 1992, vol. 69, No. 5, pp. 574-577.

Nanzando, Encyclopedia of Medicine (deluxe), Nanzando Co., Ltd. Jan. 16, 1998, vol. 18, p. 300.

Office Action from corresponding Japanese Patent Application No. 2003-513563 dated Mar. 12, 2009; English translation provided.

* cited by examiner

FIGURE 6
6A
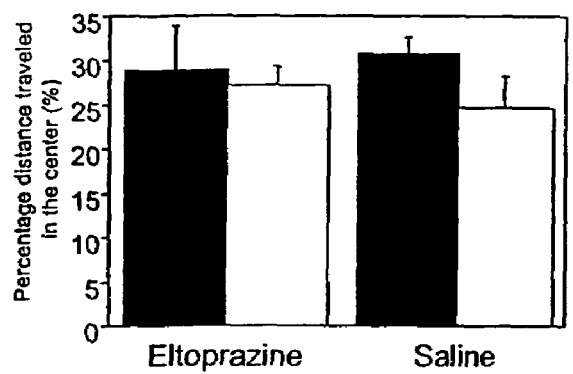
6B
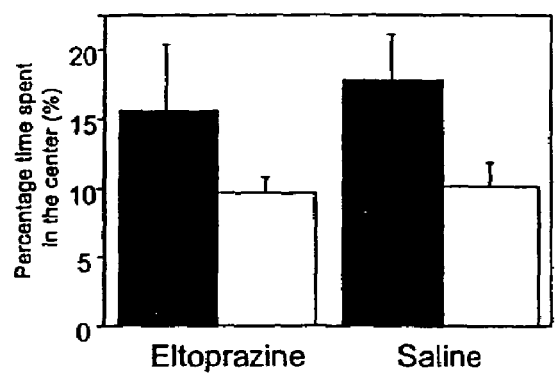
6C
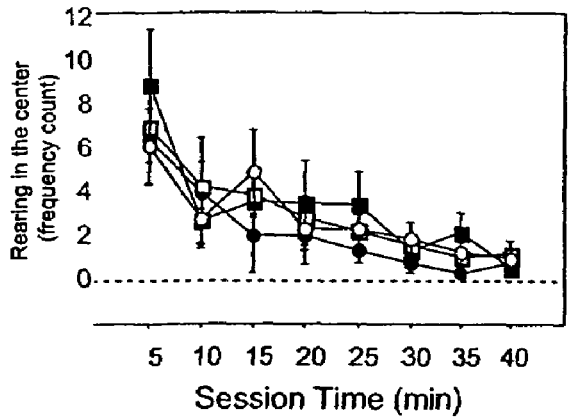
6D
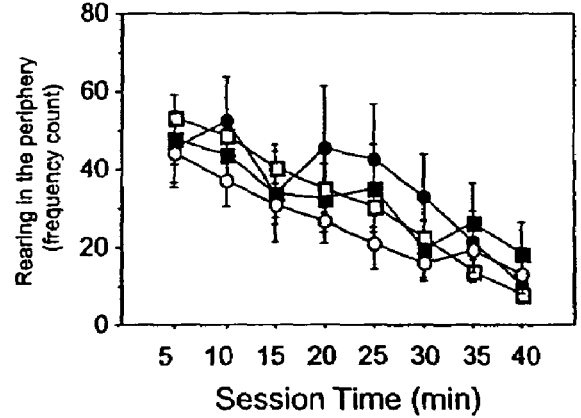

FIGURE 9
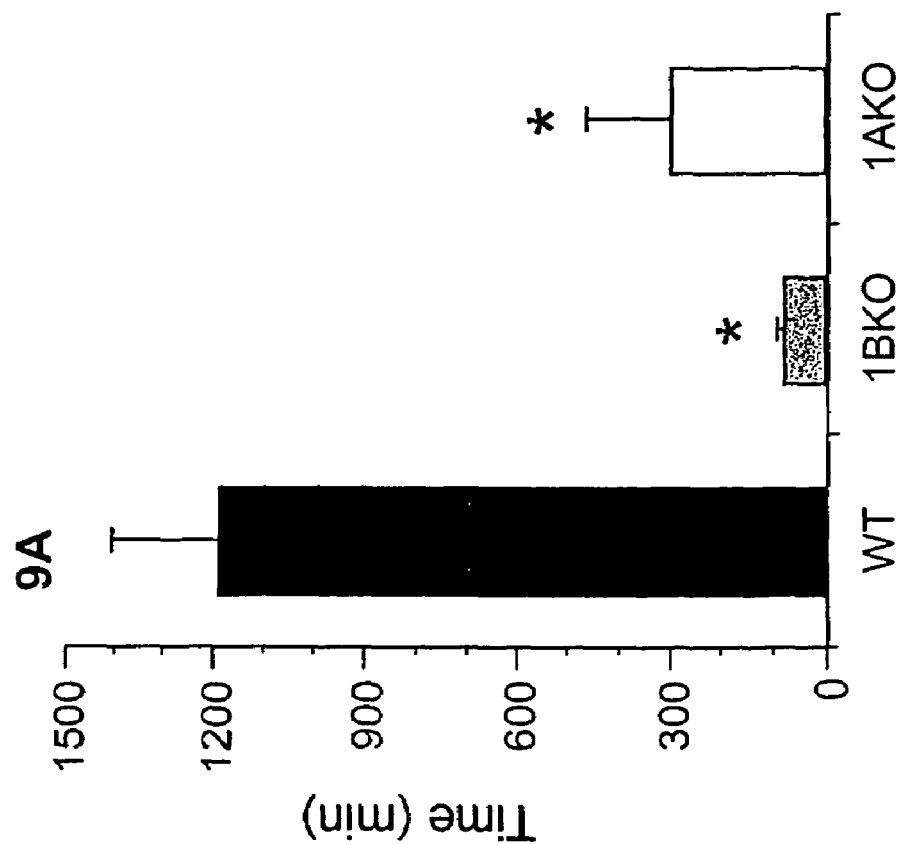
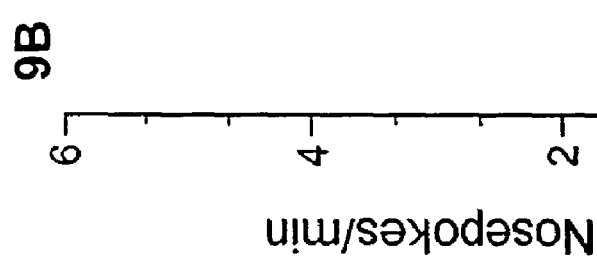

*p<.05 compared to vehicle; + p<.05 WT vs 1BKO

FIGURE 13
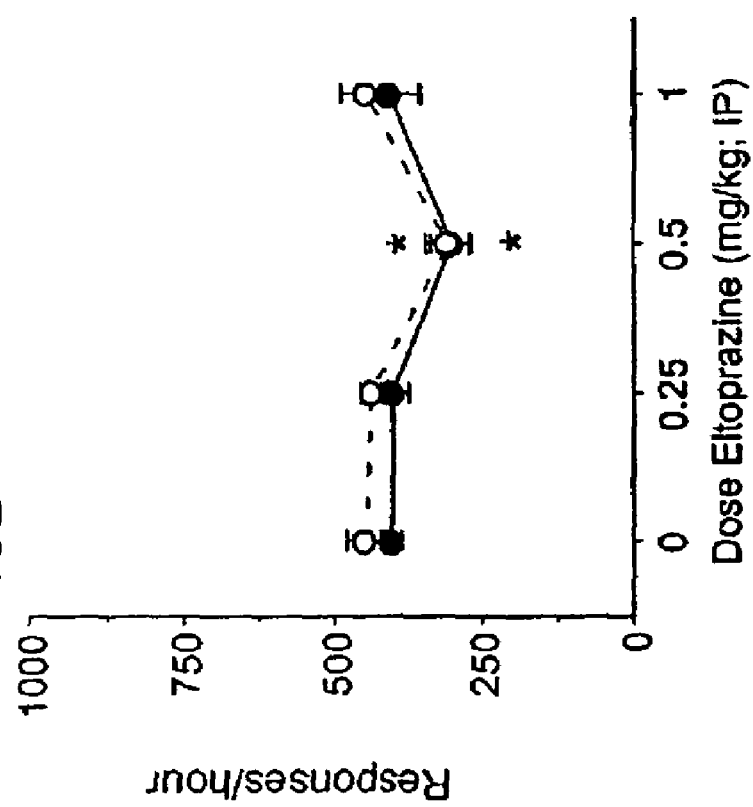
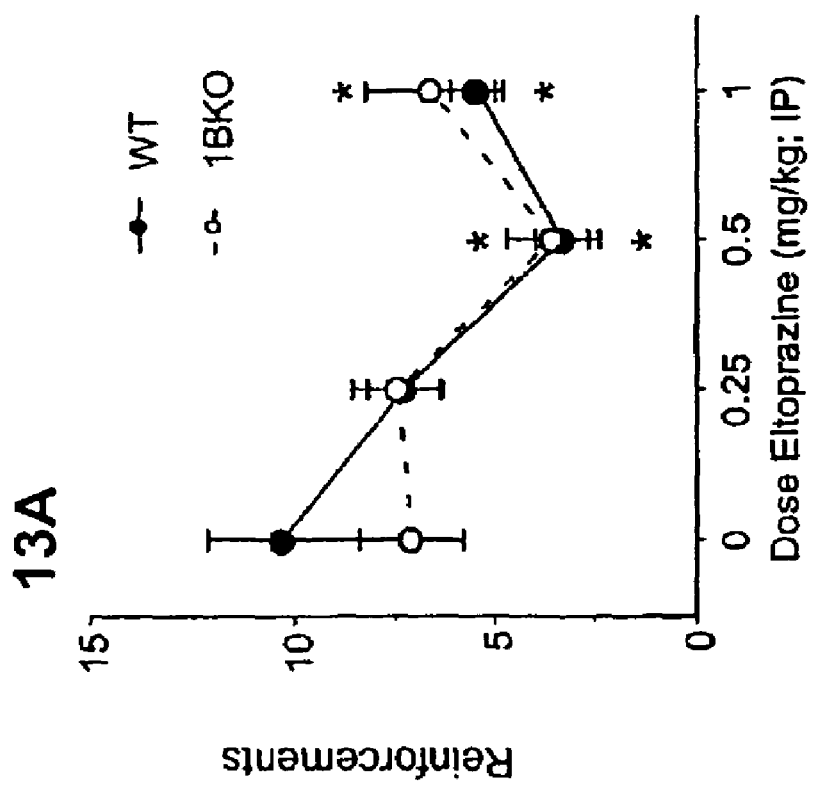
*p<.05 compared to vehicle

TREATMENT FOR ATTENTION-DEFICIT HYPERACTIVITY DISORDER

This application is a continuation under 35 U.S.C. §120 of U.S. non-provisional application No. 10/199,634, filed Jul. 19, 2002, allowed, which claims the benefit under 35 U.S.C. §119(e) of U.S. provisional application No. 60/306,825, filed Jul. 20, 2001 and U.S. provisional application No. 60/3 82,931, filed May 23, 2002. The present invention is directed to a novel method of treating Attention-Deficit/Hyperactivity Disorder ("ADHD"). This invention also relates to improving cognitive functioning.

FIELD OF THE INVENTION

Background Of The Invention

Attention-Deficit/Hyperactivity Disorder (ADHD) is a behavior disorder characterized by problems with control of attention and hyperactivity-impulsivity. The attentional difficulties and impulsivity associated with ADHD have been persuasively documented in laboratory investigations using cognitive tasks. Although these problems typically present together, one may be present without the other to qualify for a diagnosis (Am. Psychiatric Assoc. Diagnostic and Statistical Manual of Mental Disorders, $4^{th}$ Ed., Text Revision, 2000) (DSM-IV-TR). Generally, attention deficit or inattention becomes apparent when a child enters elementary school. A modified form of the disorder can persist into adulthood (Am. Psychiatric Assoc. Diagnostic and Statistical Manual of Mental Disorders, $3^{rd}$ Ed., 1987). With respect to the attention component, the child is easily distracted by outside stimuli, neglects finishing tasks, and has difficulty maintaining attention. Regarding the activity component, the child is often fidgety, impulsive, and overactive. The symptoms of ADHD may be apparent as young as preschoolers and are virtually always present prior to the age of 7 (Halperin et al., J. Am. Acad. Child Adolescent Psychiatry, 32:1038-1043, 1993).

According to the DSM-IV-TR, diagnostic criteria for Attention-Deficit/Hyperactivity Disorder relate to symptoms associated with inattention and/or hyperactivity-impulsivity. Three subtypes of ADHD are diagnosed based on the predominant symptoms presented.

Many of the symptoms that are characteristic of ADHD occur occasionally in normal children. Children with ADHD, however, exhibit these symptoms frequently, which tends to interfere with the child's day to day functioning. Such children are often challenged by academic underachievement because of excitability and impaired interpersonal relationships.

ADHD affects 2-6% of grade school children. Pediatricians report that approximately 4% of their patients have ADHD; however, in practice the diagnosis is made in children who meet several, but not all of the diagnostic criteria that is recommended in DMS-IV-TR (Wolraich et al., Pediatrics, 86(1):95-101, 1990). Boys are four times more likely to have the disorder than girls and the disorder is found in all cultures (Ross & Ross, *Hyperactivity*, New York, 1982).

Psychomotor stimulants are the most common treatment for ADHD. Safer & Krager (1988) reported that 99% of the children with ADHD were treated with stimulants, of which 93% were given methylphenidate hydrochloride (Ritalin), and the remainder were given dextroamphetamine sulfate (d-amphetamine) or pemoline (Safer & Krager, J.A.M.A., 260:2256-2258, 1988). Four separate psychostimulant medications consistently reduce the central features of ADHD, particularly the symptoms of inattention and ADHD associated hyperactivity-impulsivity: methylphenidate, d-amphetamine, pemoline, and a mixture of amphetamine salts (Spender et al., Arch. Gen. Psychiatry, 52:434-443, 1995). These drugs block uptake sites for catecholamines on presynaptic neurons or stimulate the release of granular stores of catecholamines. They are metabolized and leave the body fairly rapidly, and have a therapeutic duration of action of 1 to 4 hours. The psychostimulants do not appear, however, to make long-term changes in social or academic skills (Pelham et al., J. Clin. Child Psychology, 27:190-205, 1998). Stimulants are generally started at a low dose and adjusted weekly. Common stimulant side effects include insomnia, decreased appetite, stomachaches, headaches, and jitteriness. Psychostimulants also have the potential for abuse, because they are addictive. Thus, current methods of treating ADHD provide inadequate treatment for some patients and/or have side effects that limit their usefulness.

Children who cannot tolerate psychostimulants often use the antidepressant bupropion. While bupropion is not as effective as stimulants, it may be used as an adjunct to augment stimulant treatment.

Castellanos et al. concluded that ADHD is a genetically programmed disorder of brain development resulting from altered function of the frontal-striatal-pallidal-thalamocortical loops which regulate cognitive processes, attention, and motor output behaviors (Castellanos et al., Arch. Gen. Psychiatry, 53: 607-616, 1996). Although the precise etiology of ADHD is unknown, neurotransmitter deficits, genetics, and perinatal complications have been implicated.

Individuals with ADHD have been reported to have impairments in their ability to perceive intervals of time (Conners & Levin, Psychopharmacol. Bulletin, 32(1):67-73, 1996). Time perception is a useful measure of cognitive function, sensitive to dopaminergic and cholinergic manipulations in animals and humans. As in all behavioral tasks, several processes underlie good steady state performance in a temporal task. These behavioral tasks include: attention, motivation, short and long term memory, motor coordination, and instrumental learning. Scaling, discrimination, and reproduction are the three main types of temporal tasks that have been identified. In scaling, subjects must, for example, categorize a stimulus into a given set of categories ("that was a long duration") or verbally estimate the duration ("that was a 4 s duration"). In discrimination a comparison is made between two durations ("the second stimulus was longer than the first"). Finally, in reproduction a response is made that bears some relation with the stimulus (e.g. only responses that are as long or longer than the stimulus are correct).

Time perception is a particularly effective measure for testing cognitive deficits in ADHD individuals. For example, Conners & Levin (1996) showed that ADHD adults improve in measures of attention and timing with the administration of nicotine. Nicotine, like the psychostimulants methylphenidate and d-amphetamine, acts as an indirect dopamine agonist and improves attention and arousal. Studies indicate that adults and adolescents with ADHD smoke much more frequently than normal individuals or those with other psychiatric conditions, perhaps as a form of self-medication for ADHD symptoms. The results indicated that there was a significant clinician-rated global improvement, self-rated vigor and concentration, and improved performance on chronometric measures of attention and timing accuracy, and side effects were minimal (Conners & Levin, supra).

Eltoprazine hydrochloride [1-(2,3-dihyro-1,4-benzodioxin-5-yl) piperazine hydrochloride], a phenylpiperazine derivative, was originally developed as a "serenic." "Serenics" are drugs developed for the selective treatment of aggressive behavior, without negatively affecting general functioning or motor abilities, and which demonstrate minimal side effects. Thus, eltoprazine was developed to treat and manage inappropriate aggression with high specificity. While unsuccessful in clinical trials, eltoprazine did prove to be clinically safe (de Koning et al., Int. Clin. Psychopharmacol., 9:187-194, 1994).

It has been hypothesized that the mechanism of action for eltoprazine in aggression is associated with activation of central serotonergic (5-hydroxytryptophan, 5-HT) systems (Schipper, J. et al., Drug Metabolism & Drug Interactions, 8:85-114, 1990). In adults, central 5-HT neurotransmission is inversely correlated with aggression: diminished 5-HT function is associated with increased aggression. However, such a relationship is reported to be non-existent in children, including those having ADHD (Schulz et al., Psychiatry Res., 101: 1-10, 2001).

At present, seven main 5-HT receptor classes have been identified: $5\text{-}HT_1$, $5\text{-}HT_2$, $5\text{-}HT_3$, $5\text{-}HT_4$, $5\text{-}HT_5$, $5\text{-}HT_6$ and $5\text{-}HT_7$. Radioligand binding studies have revealed at least five subtypes of the $5\text{-}HT_1$ receptor (1A, 1B, 1D, 1E and 1F). Because the $5\text{-}HT_{1B}$ receptors are present in the hippocampal formation, it has been suggested that a potential role for these receptors is the modulation of memory processes (Malleret, J. Neurosci., 19:6157-68, 1999). Serotonin inhibits acetylcholine release through $5\text{-}HT_{1B}$ receptors located on septal terminals in the hippocampus (Maura and Raiteri, Eur. J. Pharmacol., 129:333-337, 1986) and glutamate release in the dorsal subiculum through $5\text{-}HT_{1B}$ receptors located on CA1 pyramidal neuron terminals (Aït Amara et al., Brain Res. Bulletin, 38(1):17-23, 1995). Stimulation of the hippocampal receptors in rats resulted in impaired spatial learning tasks and neophobic reactions in an object exploration task (Buhot and Naili, Hippocampus, 5:198-208, 1995). Thus, the blockade of $5\text{-}HT_{1B}$ receptors potentially affects attention and emotion and positively affects learning and memory processes (Buhot et al., supra). Therefore, $5\text{-}HT_{1B}$ agonists would be predicted not to enhance attention or cognitive function.

The binding profile of eltoprazine, together with the direct binding data obtained with [$^3$H] eltoprazine, shows the compound to be a selective $5\text{-}HT_1$ ligand (selective with respect to all receptors other than $5\text{-}HT_1$). Eltoprazine's binding affinity for the various 5-HT receptor subtypes closely resembles serotonin except for the relatively low affinity for the $5\text{-}HT_{1D}$ receptor with roughly equipotent affinity for the $5\text{-}HT_{1A}$, $5\text{-}HT_{1B}$, and $5\text{-}HT_{2C}$ receptors (Schipper, J. et al., supra). Eltoprazine acts as a mixed $5\text{-}HT_{1A/B}$ receptor agonist. Eltoprazine has no relevant affinity for dopamine receptors (i.e., $K_i > 1$ μM, Schipper et al., supra). Among the 5-HT receptors, the $5\text{-}HT_{1B}$ is located as an autoreceptor on axon terminals and is responsible for inhibiting neurotransmitter release, whereas it is also located postsynaptically as a heteroreceptor on axons and terminals of non-serotonergic neurons inhibiting their activity.

Pharmacokinetic studies have indicated that eltoprazine HCl is very well absorbed, with an absolute bioavailability of about 95%. The maximum plasma concentration of eltoprazine is attained within 1-4 hours after administration, followed by a decrease in plasma concentration with a terminal half-life of 7-9 hours. The cumulative renal excretion of unchanged eltoprazine is about 40%. The plasma elimination half-life ranges between 5-12 hours. Eltoprazine plasma concentrations increase in a linear dose-dependent manner (De Vries et al., Clinical Pharmacology, 41:485-488, 1991).

SUMMARY OF INVENTION

This invention relates to methods and compositions useful for treating ADHD in humans and the behaviors associated therewith. The compounds for use in the invention are believed to be effective in the treatment of ADHD and exhibit reduced side effects and are not expected to have abuse potential, as compared to other available therapeutics.

Treatment of ADHD according to this invention may be used to reduce one or more of any of the diagnostic criteria associated with ADHD. In a preferred embodiment of this invention, eltoprazine is administered to individuals to provide treatment of symptoms associated with ADHD. One object of the invention is to provide a method for treating ADHD by administering to an individual a therapeutically effective amount of a compound of formula 1

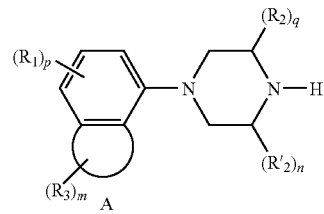

wherein
$R_1$ is hydrogen, alkyl, cycloalkyl, optionally esterified hydroxyalkyl, alkoxyalkyl, optionally substituted phenyl or heteroaryl, alkoxy, aryloxy, alkylthio, arylthio, acyl, alkoxycarbonyl, aminocarbonyl, alkyl- or dialkylaminocarbonyl, nitro, amino, alkyl- or dialkyl-amino, acylamino, alkylsulfonylamino, arylamino, cyano, halogen, trifluoromethyl, trifluoromethoxy, optionally esterified hydroxyl, alkyl- or amino-sulphonyl or -sulphinyl, alkyl- or dialkyl-aminosulphonyl or -sulphinyl, and p has the value 0-3;

$R_2$ and $R'_2$ are independently hydrogen or an alkyl group and n and q can have the value 0 or 1;

$R_3$ may have the same meaning as $R_1$, or is alkylidene, an oxo or thioxogroup, and m has the value 0-2;

A forms, with the two carbon atoms of the phenyl group, an optionally entirely or partly unsaturated cyclic group having 5-7 atoms in the ring, which comprises 1-3 hetero atoms from the group O, S, and N, with the proviso that the sum of the number of oxygen and sulphur atoms is at most 2; and wherein
the compound may be a racemate or a single diastereomer or enantiomer;
or a pharmaceutically acceptable acid addition salt thereof.

In addition, the present invention provides a method for improving cognitive function associated with ADHD.

Another object of the invention is to provide pharmaceutical compositions for the treatment of inattention and/or hyperactivity-impulsivity associated with ADHD that have reduced side effects as compared to other available treatments.

BRIEF DESCRIPTION OF THE DRAWINGS

The following drawings are illustrative of embodiments of the invention and are not meant to limit the scope of the invention as encompassed by the claims.

FIGS. 6 A-D—Graphs depict the effect of eltoprazine on exploratory preference in coloboma mutant and wild-type mice; 6A: percent (%) time spent in the center of open field arena; 6B: distance traveled in the center of open field arena as a percent (%) of total distance traveled in entire arena; 6C: frequency of rearing in the center of the arena per 5 minute block of the behavioral session; 6D: frequency of rearing in the periphery of the arena per 5 minute block of the behavioral session.

FIGS. 9 A-B—Graphs depict acquisition of operant responding in the autoshaping paradigm by wild-type, 5-$HT_{1B}$ knockout mice (1BKO), and 5-$HT_{1A}$ knockout (1AKO) mice. Time in minutes needed to reach criterion (9A) during autoshaping, and number of nose pokes made per min±SEM (9B). Data are depicted as means±SEM. * p<0.05 compared to wild-type.

FIGS. 13 A-B—Graphs depict effect of eltoprazine (0.25, 0.5 or 1 mg/kg, i.p.) on 13A: the number of reinforcements and 13B: the response rate of wild-type (WT) and 5-$HT_{1B}$ knockout (1BKO) mice with a history of fixed-ratio 5 second (FR5) responding, challenged on a DRL-36s schedule. * p<0.05 compared to vehicle.

DETAILED DESCRIPTION OF THE INVENTION

Figure 1:
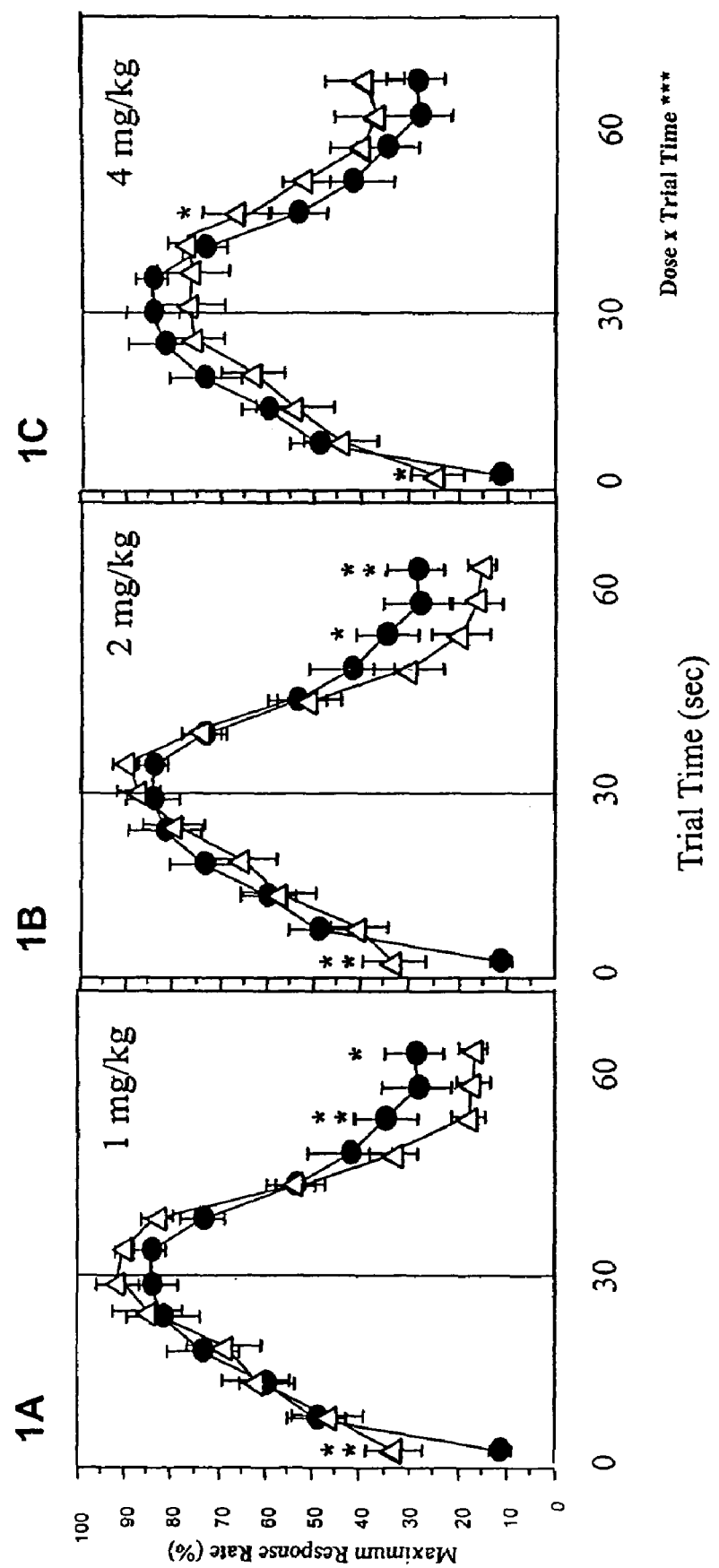
FIGS. 1 A-C—Graphs depict the relative response rate of C57BL/6J mice in the Peak Procedure (30 second reinforcement interval) after administration of 1, 2, or 4 mg/kg of d-amphetamine. * p<0.05;  p<0.01; * p<0.001.

The present invention provides a method of treating ADHD in humans. As used herein, ADHD is intended to comprise the distinct sets of symptoms associated with the three subtypes defined in DSM-IV-TR, inattention, hyperactivity/impulsivity, or combined, which present in an individual as ADHD. Impulsivity associated with ADHD is present with other symptoms, i.e., hyperactivity or hyperactivity and inattention.

ADHD of the predominantly inattentive type is diagnosed if six (or more) of the following symptoms of inattention (and fewer than six of the hyperactivity-impulsivity symptoms below) have persisted for at least 6 months to a degree that is maladaptive and inconsistent with developmental level. The inattention component of ADHD may include one or more of the following symptoms: (a) often fails to give close attention to details or makes careless mistakes in schoolwork, work, or other activities, (b) often has difficulty sustaining attention in tasks or play activities, (c) often does not seem to listen when spoken to directly, (d) often does not follow through on instructions and fails to finish school work, chores, or duties in the workplace (not due to oppositional behavior or failure to understand instructions), (e) often has difficulty organizing tasks and activities, (f) often avoids, dislikes, or is reluctant to engage in tasks that require sustained mental effort (such as schoolwork or homework), (g) often loses things necessary for tasks or activities (e.g., toys, school assignments, pencils, books, or tools), (h) is often easily distracted by extraneous stimuli, and (i) is often forgetful in daily activities (DSM-IV-TR, supra).

ADHD of the predominantly hyperactive/impulsive type is diagnosed if six (or more) of the following symptoms of hyperactivity-impulsivity (and fewer than six of the inattention symptoms above) have persisted for at least 6 months to a degree that is maladaptive and inconsistent with developmental level. The hyperactivity component of ADHD may include one or more of the following symptoms: (a) often fidgets with hands or feet or squirms in seat, (b) often leaves seat in classroom or in other situations in which remaining seated is expected, (c) often runs about or climbs excessively in situations in which it is inappropriate (in adolescents or adults, may be limited to subjective feelings of restlessness), (d) often has difficulty playing or engaging in leisure activities quietly, (e) is often "on the go" or often acts as if "driven by a motor," and (f) often talks excessively. The impulsivity component of ADHD may include one or more of the following symptoms: (g) often blurts out answers before questions have been completed, (h) often has difficulty awaiting turn, and (i) often interrupts or intrudes on others (e.g. butts into conversations or games) (DSM-IV-TR, supra).

The most common subtype of ADHD is the combined type, which comprises all three sets of symptoms, inattention, hyperactivity and impulsivity. Combined-type ADHD is diagnosed if six (or more) symptoms of inattention and six (or more) symptoms of hyperactivity/impulsivity have persisted for at least 6 months (DSM-IV-TR, supra). ADHD of the combined type, as well as the inattentive and hyperactive/impulsive subtypes, may be treated according to this invention.

Unlike traditional therapeutics, which have the potential to be abused and/or have undesirable side effects, the present invention is not expected to have the abuse potential of psychostimulants, the most widely prescribed current pharmacological treatment, and may have a side effect profile distinct from other types of pharmacologic therapeutics. Therefore, an advantage of the method of ADHD treatment provided by this invention is that certain of the undesirable side effects may be reduced or avoided.

As discussed above, ADHD is diagnosed based on an individual possessing symptoms in the symptom clusters inattentiveness, hyperactivity and impulsiveness, as defined according to the DSM-IV-TR and recognized in the art.

The compounds for use with this invention, preferably eltoprazine, may be used to treat ADHD and/or the specific symptoms or various combinations of the constellation of symptoms associated with ADHD. When symptoms associated with ADHD are treated according to this invention, preferably at least two symptoms associated with ADHD are present, and when a symptom in the impulsivity cluster is present, then another symptom of ADHD in the hyperactivity or inattentiveness cluster is also present.

Treatment of ADHD according to this invention is provided by administering to an individual in need of treatment a therapeutically effective amount of a compound of formula 1:

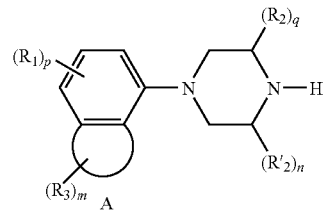

wherein
$R_1$ is hydrogen, alkyl, cycloalkyl, optionally esterified hydroxyalkyl, alkoxyalkyl, optionally substituted phenyl or heteroaryl, alkoxy, aryloxy, alkylthio, arylthio, acyl, alkoxycarbonyl, aminocarbonyl, alkyl- or dialkyl-aminocarbonyl, nitro, amino, alkyl- or dialkyl-amino, acylamino, alkylsulfonylamino, arylamino, cyano, halogen, trifluoromethyl, trifluoromethoxy, optionally esterified hydroxyl, alkyl- or amino-sulphonyl or -sulphinyl, alkyl- or dialkyl-aminosulphonyl or -sulphinyl, and p has the value 0-3;
$R_2$ and $R'_2$ are independently hydrogen or an alkyl group, and n and q can have the value 0 or 1;
$R_3$ may have the same meaning as $R_1$, or is alkylidene, an oxo or thioxogroup, and m has the value 0-2;
A forms, with the two carbon atoms of the phenyl group, an optionally entirely or partly unsaturated cyclic group having 5-7 atoms in the ring, which comprises 1-3 hetero atoms from the group O, S, and N, with the proviso that the sum of the number of oxygen and sulphur atoms is at most 2.

Unless otherwise defined, an alkyl is 1-10 carbons, aryl is 6-10 carbons, and cycloalkyl is 3-10 carbons.

When a halogen, $R_1$ is preferably fluoro, chloro or bromo, and when an alkyl group, $R_1$ is preferably a straight or branched, saturated or unsaturated group having 1-5 carbon atoms.

When an alkyl group, $R_2$ is preferably a methyl or ethyl group.

When a hydroxyalkyl group, $R_3$ preferably comprises 1-3 carbon atoms.

When $R_1$ or $R_3$ is an esterified hydroxyl group or hydroxyalkyl group, the ester group preferably has the formula O—CO—$R_4$ or —CS—$R_4$ in which $R_4$ is alkyl, aralkyl, aryl, heteroaryl, hetero aralkyl, wherein the alkyl group may be branched or unbranched, and the (hetero) aryl part may optionally be substituted, or $R_4$ may be an alkoxy, heteroalkoxy or dialkylamino group, in which the two alkyl groups can form a hetero-cyclic ring with the nitrogen atom.

When $R_1$ or $R_3$ is an etherified hydroxyl group or hydroxyalkyl group, the ether group preferably has the formula —O—$R_5$, wherein $R_5$ is a straight, branched or cyclic alkyl group having 1-5 C-atoms, or an alkoxyalkyl group having 1 or 2 C-atoms in both the alkoxy part and in the alkyl part thereof.

Eltoprazine (1-(2,3-dihydro-1,4-benzodioxanyl-5-yl) piperazine) is particularly preferred for use with this invention: $R_1$, $R_2$, $R'_2$ and $R_3$ are hydrogen and A, together with the phenyl ring to which it is attached, forms a 2,3-dihydro-1,4-benzodioxin, $C_{12}H_{16}N_2O_2$; or pharmaceutically acceptable salts thereof, preferably HCl. Another preferred compound that may be useful for this invention is batoprazine, (8-(1-piperazine)-2H-1-benzopyran-2-one). This invention also includes the use of prodrugs of the compounds of formula 1, specifically derivatives of the compounds of formula 1 that are inactive but are converted to an active form in the body following administration.

The compounds described above including eltoprazine and their method of synthesis are known in the art and are described in U.S. Pat. Nos. 4,833,142; 5,424,313; European Patent Nos. 189,612; and 138,280, which are incorporated herein by reference in their entirety.

ADHD and/or symptoms associated with ADHD are treated according to this invention by administering therapeutic dosages of compounds according to formula 1.

Eltoprazine's utility for treating ADHD and symptoms associated with ADHD, is based on the surprising discovery disclosed herein that eltoprazine shares certain activity profiles with other compounds known to be useful for treating such conditions. Amphetamines enhance monoaminergic transmission; however, their mechanism of action in ADHD is still the subject of much speculation. Without being bound by theory, one possible mechanism is the enhancement of dopamine release in those areas of the brain that are involved in attentional mechanisms, such as the frontal cortex, however, such a model seems to be overly simplistic and incomplete. (Nestler, Hyman, & Malenka, *Molecular Neuropharmacology: A Foundation for Clinical Neuroscience*, McGraw Hill, 2001). Psychoactive substances such as amphetamines typically show a U-shape curve, with low doses being cognitive enhancers, and high doses being disruptive of cognitive performance.

The mechanism underlying these U-shape curves is poorly understood, with one possibility being the differential action on pre- and postsynaptic dopamine D2 receptors. It is possible that low doses preferentially affect the post- (or pre-) synaptic receptors, and that only higher doses affect both types. The differential action could be the result of different binding characteristics (due to subtle changes in the receptors), or to differences in the amount of receptor reserve (where high receptor reserve results in a stronger effect). This dual pre- and postsynaptic action of dopamine (and of dopamine agonists) is mimicked in the serotonergic system, in which the $5\text{-HT}_{1A}$ and $5\text{-HT}_{1B}$ receptors exist as both autoreceptors (presynaptic) and heteroreceptors (postsynaptic) and have opposite effects. Presynaptic action typically results in a reduction of neurotransmitter release (and less activation of target receptors), whereas postsynaptic action results in enhanced activation of target receptors.

Although the main target of amphetamine-like drugs (and of bupropion, one antidepressant used for ADHD when adverse reactions prevent the use of psychostimulants) is the dopaminergic system, strong interactions between dopamine and serotonin are known. As a result, drugs that affect the serotonin system will very likely have secondary effects in the dopaminergic system. Moreover, serotonergic drugs that have a dual pre- and postsynaptic action would be expected to show U-shaped responses. Thus, a drug which acts as a cognitive enhancer at low doses, and disrupts performance at high doses, may be a drug that mimics amphetamine-like effects, and therefore may be of value in the treatment of ADHD.

The dose of the compound used in treating ADHD in accordance with this invention will vary in the usual way with the seriousness of the disorder, the weight, and metabolic health of the individual in need of treatment. The preferred initial dose for the general patient population will be determined by routine dose-ranging studies, as are conducted, for example, during clinical trials. Therapeutically effective doses for individual patients may be determined, by titrating the amount of drug given to the individual to arrive at the desired therapeutic or prophylactic effect, while minimizing side effects. A preferred initial dose for this compound, may be estimated to be between about 0.1 mg/day and 100 mg/day. More preferably, the initial dose is estimated to be between 0.1 mg/day and 30 mg/day. Even more preferred, the initial dose is estimated to be between 0.1 mg/day and 10 mg/day.

To achieve a therapeutic effect for ADHD and symptoms thereof, the preferred plasma concentration of the compounds for use with this invention is between about 0.06 ng/ml and about 200 ng/ml in a human. The preferred plasma concentration of eltoprazine for use with this invention is between about 0.2 ng/ml and about 65 ng/ml in a human.

Administration of the compounds of this invention may be by any method used for administering therapeutics, such as for example oral, parenteral, intravenous, intramuscular, subcutaneous, or rectal administration.

In addition to comprising the therapeutic compounds for use in this invention, especially eltoprazine [1-(2,3-dihyro-1,4-benzodioxin-5-yl) piperazine] or pharmaceutically acceptable salts (preferably HCl in the case of eltoprazine) or prodrug thereof, the pharmaceutical compositions for use with this invention may also comprise a pharmaceutically acceptable carrier. Such carriers may comprise additives, such as preservatives, excipients, fillers, wetting agents, binders, disintegrants, buffers may also be present in the compositions of the invention. Suitable additives may be, for example magnesium and calcium carbonates, carboxymethylcellulose, starches, sugars, gums, magnesium or calcium stearate, coloring or flavoring agents, and the like. There exists a wide variety of pharmaceutically acceptable additives for pharmaceutical dosage forms, and selection of appropriate additives is a routine matter for those skilled in art of pharmaceutical formulation.

The compositions may be in the form of tablets, capsules, powders, granules, lozenges, suppositories, reconstitutable powders, or liquid preparations such as oral or sterile parenteral solutions or suspensions.

In order to obtain consistency of administration it is preferred that a composition of the invention is in the form of a unit dose. Unit dose forms for oral administration may be tablets, capsules, and the like, and may contain conventional excipients such as binding agents, for example syrup, acacia, gelatin, sorbitol, tragacanth, or polyvinylpyrrolidone; and carriers or fillers, for example lactose, sugar, maize-starch, calcium phosphate, sorbitol or glycine. Additives may include disintegrants, for example starch, polyvinylpyrrolidone, sodium starch glycolate or microcrystalline cellulose; preservatives, and pharmaceutically acceptable wetting agents such as sodium lauryl sulphate.

In addition to unit dose forms, multi-dosage forms are also contemplated to be within the scope of the invention. Delayed-release compositions, for example those prepared by employing slow-release coatings, micro-encapsulation, and/or slowly-dissolving polymer carriers, will also be apparent to those skilled in the art, and are contemplated to be within the scope of the invention.

The solid oral compositions may be prepared by conventional methods of blending, filling, tabletting or the like. Repeated blending operations may be used to distribute the active agent throughout those compositions employing large quantities of fillers. Such operations are conventional in the art. The tablets may be coated according to methods well known in normal pharmaceutical practice, for example with an enteric coating.

Oral liquid preparations may be in the form of, for example, emulsions, syrups, or elixirs, or may be presented as a dry product for reconstitution with water or other suitable vehicle before use. Such liquid preparations may contain conventional additives such as suspending agents, for example sorbitol syrup, methyl cellulose, gelatin, hydroxyethylcellulose, carboxymethylcellulose, aluminum stearate gel, and hydrogenated edible fats; emulsifying agents, for example lecithin, sorbitan monooleate, or acacia; non-aqueous vehicles (which may include edible oils), for example almond oil or fractionated coconut oil, oily esters such as esters of glycerine, propylene glycol, or ethyl alcohol; preservatives, for example methyl or propyl p-hydroxybenzoate or sorbic acid; and if desired conventional flavoring or coloring agents.

For parenteral administration, fluid unit dosage forms are prepared utilizing the compound and a sterile vehicle, and, depending on the concentration used, can be either suspended or dissolved in the vehicle. In preparing solutions the compound can be dissolved in water or saline for injection and filter sterilized before filling into a suitable vial or ampoule and sealing. Advantageously, additives such as a local anaesthetic, preservative and buffering agent can be dissolved in the vehicle. Suitable buffering agents are, for example, phosphate and citrate salts. To enhance the stability, the composition can be frozen after filling into the vial and the water removed under vacuum. Parenteral suspensions are prepared in substantially the same manner, except that the compound is suspended in the vehicle instead of being dissolved, and sterilization cannot be accomplished by filtration. The compound can be sterilized by conventional means, for example by exposure to radiation or ethylene oxide, before being suspended in the sterile vehicle. Advantageously, a surfactant or wetting agent is included in the composition to facilitate uniform distribution of the compound.

The invention will be explained in more detail below by way of examples, which illustrate the effectiveness of prototypical compound eltoprazine in alleviating symptoms associated with ADHD.

EXAMPLE 1

The peak procedure is a behavioral model designed to assess an animal's ability to learn an appropriate time period in which to perform a task and a time period in which the animal will be rewarded if the task is performed. The model provides information concerning excitatory and inhibitory components of behavior, as subjects must respond to perform a task when appropriate and stop responding in an "empty trial" when time for reward has elapsed and the reward has not been delivered. The task is sensitive to conditions where there is a failure in inhibitory mechanisms, such as seems to be the case for ADHD (Pliszka et al., Biol. Psychiatry, 48:238-46, 2000).

In the peak procedure, mice are trained to work for food that is delivered at the same time in each trial, but withdrawn in some unreinforced trials. Typically, the response rate increases up to a maximum around the reinforcement time, and then decreases to a low toward the end of the trial. The shape of the response rate indicates whether the animal is sensitive to the time of reinforcement. To be able to perform well in this model, the animals need to be able to learn several tasks. First, the animal must make an association between a response (lever pressing, nose poking or key pecking) and the delivery of reward. Second, the animal must be able to perceive and remember time. Third, the animal must act on its remembered time by starting and then stopping or inhibiting the response. Fourth, the animal must be able to compare the elapsed time in the trials with its remembered time to reinforcement. In each trial the time clock is reset, and the animal must reset its internal "counter," i.e., at the beginning of each trial animals should start "timing" the trial time from zero. The ability to perform this task depends on the animal's working memory. Starting the internal clock at the beginning of the trial requires that the animal pays attention to the trial start time, which could be in the form of a visual signal, or as reported herein, the introduction of a lever into the experimental chamber. Failure to attend resulted in higher variability and a loss of accuracy during trial performance. Accuracy is measured by looking at the shape of the response function; therefore, if the response function is sharper and centered on the reinforcement time it supports a conclusion that attentional processes have been heightened.

Mice were food deprived to 85-90% of their free-feeding body weight by supplementing food earned during experimental sessions with a measured amount after the session had ended. For the amphetamine dose response curve, C57BL/6J mice were used (n=14). For the eltoprazine study, C3H mice were used (n=14). Once deprived, animals were trained to lever-press in an operant box (Med Associates) using ultra-sensitive levers. During the training, food was delivered after any one press of the lever. Once lever-pressing was robust (about 1 week), a fixed interval of 10 seconds was introduced between the beginning of a trial (when the lever is introduced into the chamber) and the reinforced response. All premature responses had no programmed consequences. After one week the fixed interval was increased to 30 seconds and animals were trained on this new fixed interval until response curves were stable. The last phase of training included empty or "peak" trials in which reinforcement was withdrawn and the trial continued for 3 times the fixed interval.

Once the performance during peak trials was stable, a dose response study was initiated. Drug injections were delivered 30 minutes prior to the session. Doses were scheduled on Monday, Wednesday and Friday, with Tuesday and Thursday being normal sessions without a drug. Eltoprazine dose responses were done on the same mice with at least 1 week of washout period. During this time all responses were unreinforced. Responses during these peak trials were recorded and transformed into a relative responding measure by dividing the number of responses in each 5 minute bin by the maximum response rate at any time interval in that trial. After relative responses had been calculated for each trial, an Analysis of Variance (ANOVA) with trial time and dose as within factors was performed. Significant interactions were followed up by planned pair-wise comparisons between the saline response and the corresponding drug dose response.

In subjects with problems of inhibition and response control, it will be beneficial to find a drug that improves performance by sharpening the response curve and providing the subject with greater control over the start and stop time for response. The experiments with mice and the timing procedure were designed to maximize the chance of finding drugs that improve performance. Amphetamine was tested in low to moderately high doses. Amphetamine, a drug of abuse, is used by humans as a cognitive enhancer at low doses, and as a recreational drug (that results in a "high" state) at much higher doses (more than five times the cognitive enhancing dose).

FIG. 1 shows the response pattern obtained with d-amphetamine. At the lower doses, 1 and 2 mg/kg, the amphetamine curve demonstrates a higher peak in the curve followed by a rapid decrease, relative to saline (FIGS. 1A, 1B). Conversely, at the higher 4 mg/kg dose, the amphetamine curve does not peak as high as the lower dose and the curve is flatter (FIG. 1C). Times at which pairwise comparisons between saline and amphetamine reached significance are indicated on the graphs. ANOVA revealed a significant dose×trial time interaction, p<0.001.

The lowest two doses acted as cognitive enhancers as they sharpened the curve. The highest dose disrupted performance, flattening the curve. Improved performance is demonstrated by a sharp peak in the curve followed by a rapid decrease. A less marked peak in the curve followed by a flattening is indicative of deteriorated performance. Cognitive enhancement, as used herein, refers to heightened attentional processes.

EXAMPLE 2

Figure 2:
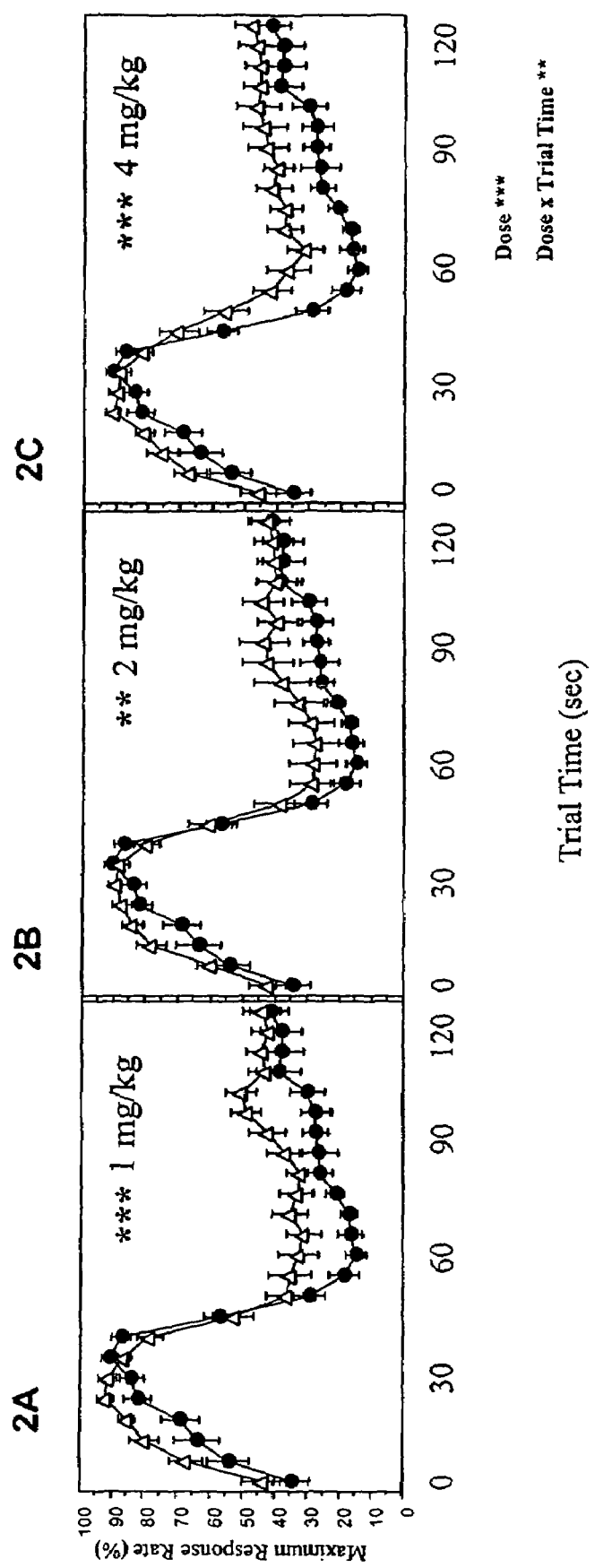
FIGS. 2 A-C—Graphs depict the relative response rate of C3H mice in the Peak Procedure (30 second reinforcement interval) after administration of 1, 2, or 4 mg/kg of eltoprazine.  p<0.01; * p<0.001.

The following results were obtained using the methods described in Example 1. Eltoprazine was investigated using a very wide dose range: 0.1-4 mg/kg. FIG. 2 demonstrates decreased cognitive enhancement at higher doses of eltoprazine. At 1, 2, and 4 mg/kg eltoprazine, the performance curves were flatter than the saline curve (FIGS. 2A, 2B, and 2C, respectively). ANOVA revealed a significant dose main effect, p<0.001, and a significant dose×trial time interaction, p<0.01.

Figure 3:
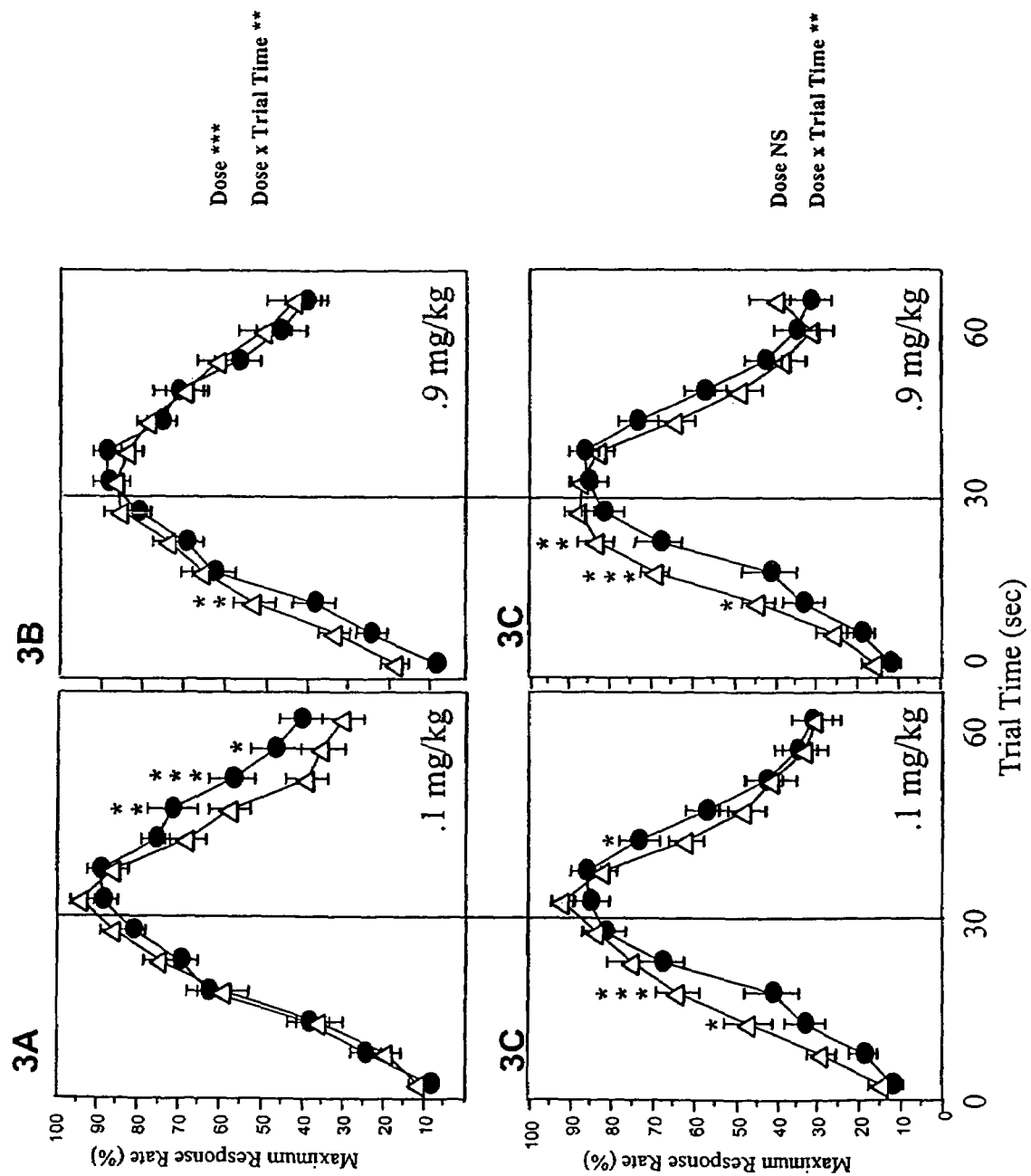
FIG. 3-Graphs depict the relative response rate of C3H mice in the Peak Procedure (30 second reinforcement interval) after administration of low doses, 0.1 and 0.9 mg/kg, of eltoprazine. * p<0.05;  p<0.01; * p<0.001.

At lower doses of eltoprazine, however, cognitive enhancement was observed, as illustrated in FIG. 3. In two separate studies of 0.1 and 0.9 mg/kg eltoprazine, the peaks of the response curves are higher and the curves are sharper. Times at which pairwise comparisons between saline and amphetamine reached significance are indicated on the graphs. ANOVA revealed a significant dose main effect in one study, p<0.001, and a significant dose×trial time interaction in both studies, p<0.01. In conclusion, eltoprazine at low doses, may act as a cognitive enhancer and is expected to be useful in the treatment of ADHD and associated symptoms thereof.

EXAMPLE 3

The coloboma (Cm) mutant mouse has been proposed as a rodent model for ADHD (for review, see Wilson, Neurosci. Biobehav. Rev., 24:51-57, 2000). The rationale for this proposal is three fold: first, Cm mutants (heterozygote) exhibit elevated spontaneous locomotor hyperactivity which averages three to four times the activity of wild-type littermates (Hess et al., J. Neurosci., 12:2865-2874, 1992; Hess et al., J. Neurosci., 16:3104-3111, 1996); second, this Cm mutation-associated hyperactivity can be ameliorated by low and moderate doses (2-16 mg/kg) of D-amphetamine (Hess et al., 1996, supra), a psychostimulant commonly prescribed to treat ADHD; and lastly, Cm mutant mice exhibit delays in achieving complex neurodevelopmental milestones in behavior (Heyser et al., Brain Res. Dev. Brain Res., 89:264-269, 1995) and deficits in hippocampal physiology and learning performance (Steffensen et al., Synapse, 22:281-289, 1996; Raber et al., J. Neurochem., 68:176-186, 1997) which may correspond to impairments seen in ADHD.

The genetic defects associated with Cm mutant mice include a deletion of the gene Snap (Hess et al., 1992, supra; Hess et al., Genomics, 21:257-261, 1994). Snap encodes SNAP-25, which is a key component of the synaptic vesicle docking and fusion complex required for regulated synaptic transmission. As a result, Cm mutant animals show marked deficits in $Ca^{2+}$-dependent dopamine release (Raber et al., supra). This hypofunctioning DA system, which may involve meso-cortical, meso-limbic, as well as nigro-striatal circuitries has been suggested as a possible mechanism underlying hyperactivity associated with Cm mutation (Sagvolden, et al., Behav. Brain Res., 94:61-71, 1998; Sagvolden and Sergeant, Behav. Brain Res., 94:1-10, 1998).

Amphetamine, but not methylphenidate, normalizes the hyperactivity in Cm mutant mice; in both control and Cm mutants, methylphenidate increases locomotor activity in a dose-dependent manner (Hess et al., 1996, supra). The differential effect of these two ADHD medications, which both act at the presynaptic terminal, has been attributed to the differing mechanisms of action of increasing synaptic DA concentrations (Hess et al., 1996, supra).

It has now been surprisingly found that eltoprazine, a $5\text{-HT}_{1A/1B}$ receptor agonist, produces an amphetamine-like effect on hyperactivity in coloboma mice.

Animals

Heterozygote coloboma mice were originally purchased from The Jackson Laboratory (Bar Harbor, Me.) and were bred and maintained in our colony. In the current study, 20 mutant mice and 25 wild-type littermates, all aged 8 to 10 weeks, were used. Animals were divided into 4 groups: mutant/drug-treatment (n=11), mutant/vehicle-control (n=9), wild-type/drug-treatment (n=13), wild-type/vehicle-control (n=12). Age and gender were balanced among groups. All animals were housed as littermates (2-4 mice per cage) and were maintained on ad libitum food and water with a 12 hr light/dark cycle.

Behavioral Testing

Open-field testing was performed under normal lighting conditions. Mice were brought into the experimental room and allowed at least 1 hr of acclimatization. Thirty minutes prior to testing, animals received an ip. injection of either d-amphetamine (4 mg/kg), eltoprazine (0.5 mg/kg) or saline. The mice were then placed in the activity monitor arenas (27×27×20 cm, Med Associates). Four animals of matching genotype and treatment were tested at one time. Each testing session lasted 40 minutes, after which animals were returned to their home cages. An automated infrared beam array system measured locomotor activity (total distance traveled) and number of center entries (zone crossings).

Results

Figure 4:
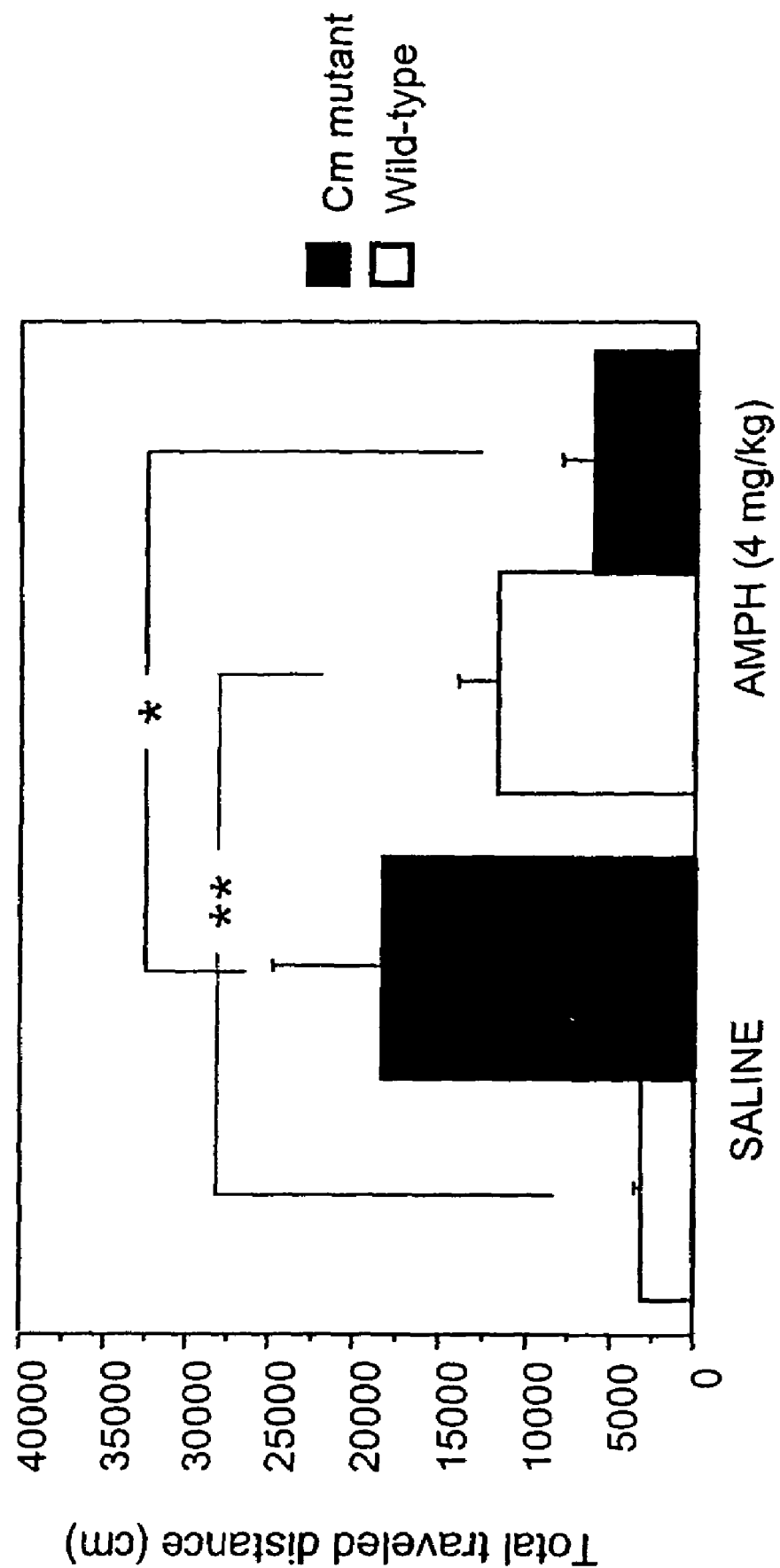
FIG. 4-Graph depicts the effect of 4 mg/kg amphetamine on locomotor activity in coloboma mutant and wild-type mice, as measured by total distance traveled in a fixed time period. * p<0.05; ** p<0.01.
Figure 5:
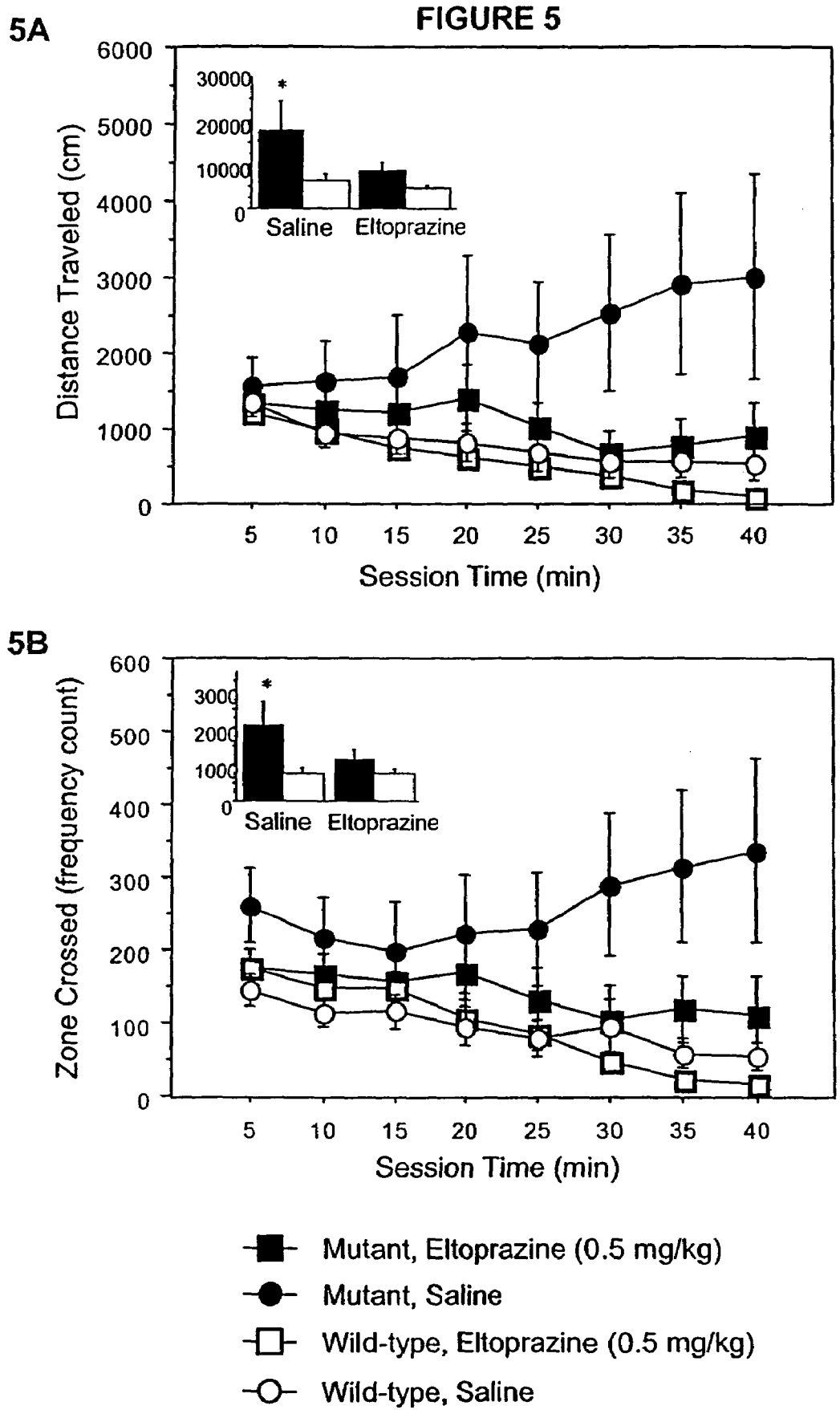
FIGS. 5 A-B—Graphs depict the effect of 0.5 mg/kg eltoprazine on locomotor activity in coloboma mutant and wild-type mice; 5A: distance traveled per 5 minute block of the behavioral session; insert shows total distance traveled in the session; 5B: depicts the frequency of zone crossings per 5 minute block of the behavioral session; insert shows total number of crossings in the session. * p<0.05 compared to eltoprazine.

The data reveal a significant genotypic effect on parameters of hyperactivity that is reduced by eltoprazine treatment. Coloboma mutant mice are hyperactive relative to wild-type mice, as measured by increased locomotor activity. A genotypic effect on total ambulatory distance is depicted in FIGS. 4 and 5A (inset) and a genotypic effect on total crossed zones is depicted in FIG. 5B (inset). FIG. 4 and inset of FIG. 5A illustrate that saline-treated mutant Cm mice traveled roughly three-six times further in distance than did their saline-treated wild-type littermates (18,386±6387 vs. 3116±338 cm, FIG. 4; 17725±6636 vs. 6288±1565 cm, FIG. 5A), the scale of which is consistent with previously reported findings (Hess et. al., 1992, 1996 supra). Analysis of variance (ANOVA) revealed that this genotypic effect on total ambulatory distance was significant ($F_{(1,41)}$=6.798, p=0.0127) (FIG. 5A). FIG. 5B illustrates that saline-treated mutant mice crossed zones more frequently than did their saline-treated wild-type littermates. ANOVA revealed this genotype effect on total crossed zones also is significant ($F_{(1,41)}$=7.577, p=0.0088).

The genotype-related difference in locomotion was, however, largely and significantly diminished in eltoprazine-treated animals and reversed in amphetamine-treated animals.

Administration of amphetamine, 4 mg/kg, to wild-type mice had a stimulatory effect, significantly increasing total distance traveled, as illustrated in FIG. 4 (3116±338 vs.

11657±2370 cm; ANOVA F(1,15)=11.276, p=0.0043). By contrast, the same dose of amphetamine administered to Cm mutant mice significantly decreased total distance traveled relative to saline-treated Cm mutants (18386±6387 vs. 5966±1938 cm; ANOVA F(1,11)=5.355, p=0.0459) to within the range of saline-treated wild-type mice. Amphetamine effectively normalized the hyperactive locomotor behavior of the coloboma mutant mice, significantly decreasing locomotion in the Cm mutant mice. ANOVA revealed a significant treatment×genotype interaction (F(1,25)=11.038, p=0.0027).

Eltoprazine did not influence the locomotor activity of wild-type mice, however, the effects of eltoprazine on Cm mutant mice were surprisingly similar to amphetamine. Indeed, administration of eltoprazine (0.5 mg/kg, i.p.) reduced the total ambulatory distance of the Cm mutants to 8641±1811, more than 50% reduction from that of saline-treated Cm mutants, as illustrated in FIG. 5A. Likewise, as depicted in FIG. 5B, eltoprazine decreased the number of zone crossings in Cm mutants to within the range of saline-treated wild-type mice. Notably, eltoprazine only marginally affected locomotion in wild-type animals, as measured by distance traveled or zones crossed. This differential drug effect made the locomotor activity of eltoprazine-treated mutant and wild-type animals indistinguishable from that of saline-treated wild-type animals. In other words, eltoprazine effectively normalized the hyperactivity associated with the Cm mutation.

Eltoprazine has been tested in a variety of species, including human, over a broad range of doses, and the overall safety and tolerance of the compound are good (de Koning et al., supra). Importantly, no sedative effect of eltoprazine was observed at the dose used. Indeed, the activity of eltoprazine-treated animals is comparable to that of normal animals in this study, which rules out the possibility that the calming (i.e., anti-hyperactive) effect of eltoprazine is due to a general reduction in mobility.

It has previously been shown that the psychostimulant anti-ADHD agents d-amphetamine, but not methylphenidate, reinstated normal locomotor activity of the Cm mutants, suggesting an inconsistent effect of psychostimulants on this model of hyperactivity (Hess et. al., 1996, supra). However, the findings of this invention suggest that eltoprazine has a specific regulatory role over hyperactivity. In summary, eltoprazine is acting like the anti-ADHD agent amphetamine in the Cm animal model of ADHD, but lacks the adverse stimulant properties of amphetamine observed in wild-type mice, demonstrating the therapeutic potential and advantages of eltoprazine as an anti-ADHD agent.

EXAMPLE 4

Eltoprazine-induced normalization of locomotion in Cm mutant mice was found not to be associated with altered exploratory preference or frequency of rearing. Although some researchers have argued that eltoprazine may enhance neophobia in rodents (Rodgers et. al., Behav. Pharmacol., 3:621-634, 1992; Griebel et al., Psychopharmacology (Berl), 102:498-502, 1990), the doses (1.25 mg/kg or higher) and the tests used (elevated plus maze or light-dark box) in these studies were different from those used in the present study.

Open-field testing was performed as described in Example 3. Rodents by nature are neophobic as measured by two parameters in the open-field test including: exploratory preference for the periphery over center of the arena and the frequency of rearing. Eltoprazine did not alter either parameter in this study. As FIG. 6 illustrates, eltoprazine had no effect on exploratory preference in either Cm or wild-type mice. Animals of both treatment groups spent a comparable amount of time traveling in the center and ambulated a similar distance (FIG. 6A, 6B); they also exhibited the same pattern of rearing behavior (FIG. 6C, 6D).

Taken together, Examples 3 and 4 indicate that eltoprazine selectively dampens locomotor activity in the Cm mutant mouse without affecting other behaviors of the animal. Thus, the regulatory effect of eltoprazine over Cm-induced hyperactivity is highly specific.

EXAMPLE 5

The primary targets for eltoprazine are reported to be $5\text{-HT}_{1A}$ and $5\text{-HT}_{1B}$ receptors (see Schipper et al., supra). It surprisingly has been discovered, however, that the effects of eltoprazine in alleviating or normalizing symptoms associated with ADHD, such as hyperactivity, may be mediated by mechanisms other than agonist action at $5\text{-HT}_{1B}$ receptors. If $5\text{-HT}_{1B}$ receptors are important in mediating the anti-ADHD effects of eltoprazine, a specific $5\text{-HT}_{1B}$ receptor agonist should mimic the effects of eltoprazine in models of ADHD. $5\text{-HT}_{1B}$ receptor agonists were found not to produce the same effects as eltoprazine on locomotor activity.

Figure 7:
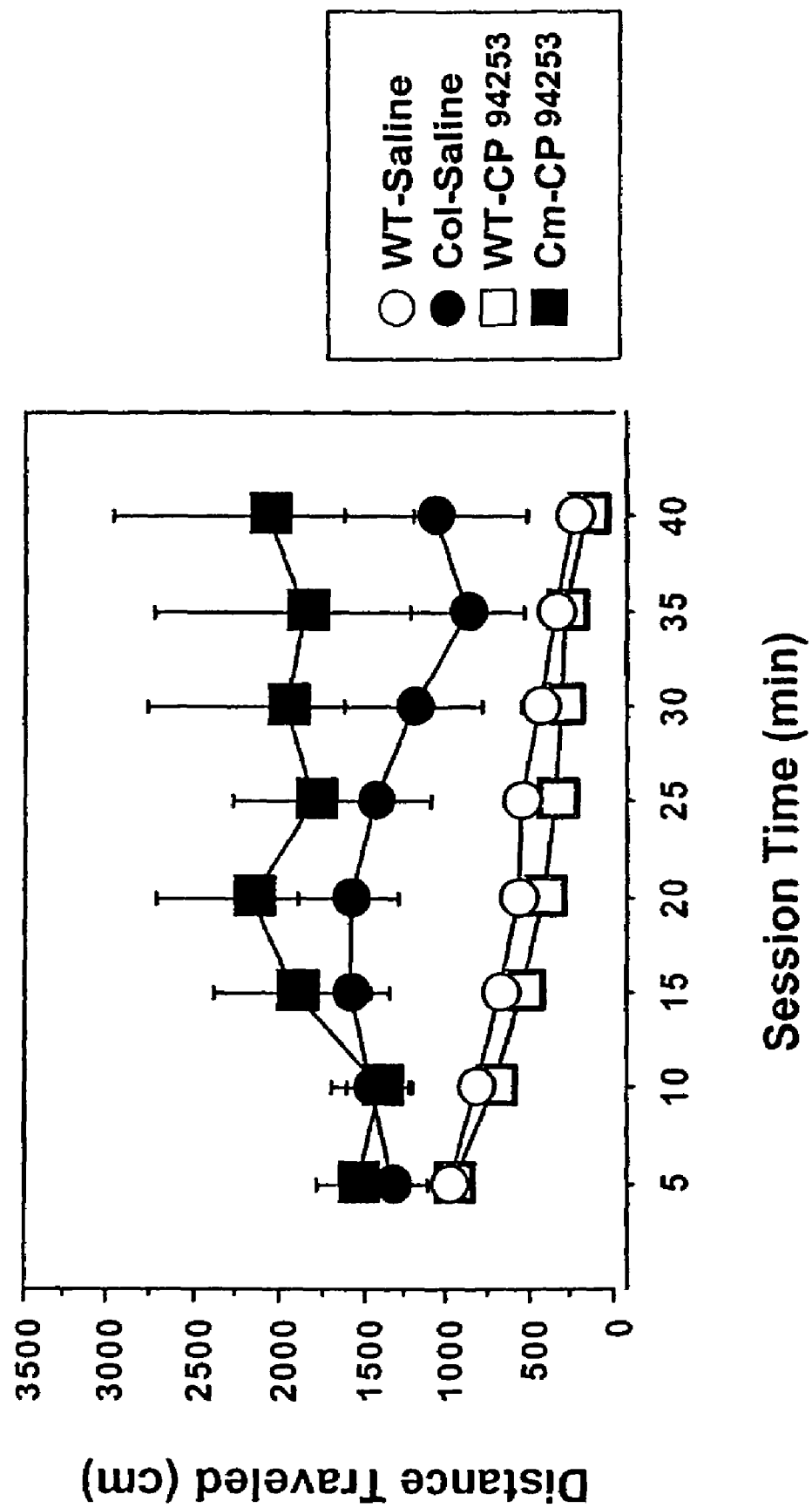
FIG. 7-Graph depicts the effect of 5-$HT_{1B}$ receptor agonist CP 94253, 0.5 mg/kg, on locomotor activity in coloboma mutant and wild-type mice.

The $5\text{-HT}_{1B}$ receptor agonist CP 94253 was tested in coloboma mutant mice in the open field test for locomotor activity using the methods described in Example 3. FIG. 7 demonstrates that, unlike eltoprazine, CP 94253 fails to normalize the hyperactive behavior of coloboma mice. CP 94253, at 0.5 mg/kg, did not decrease significantly the distance traveled in coloboma mutants, but rather tended to increase distance traveled. CP 94253 also had no effect on the locomotor activity of wild-type mice. The effects of CP 94253 on locomotor activity in coloboma mice contrasts with the effects of both eltoprazine and amphetamine, surprisingly suggesting that the calming effects of eltoprazine are mediated by mechanisms other than the $5\text{-HT}_{1B}$ receptor.

EXAMPLE 6

Figure 8:
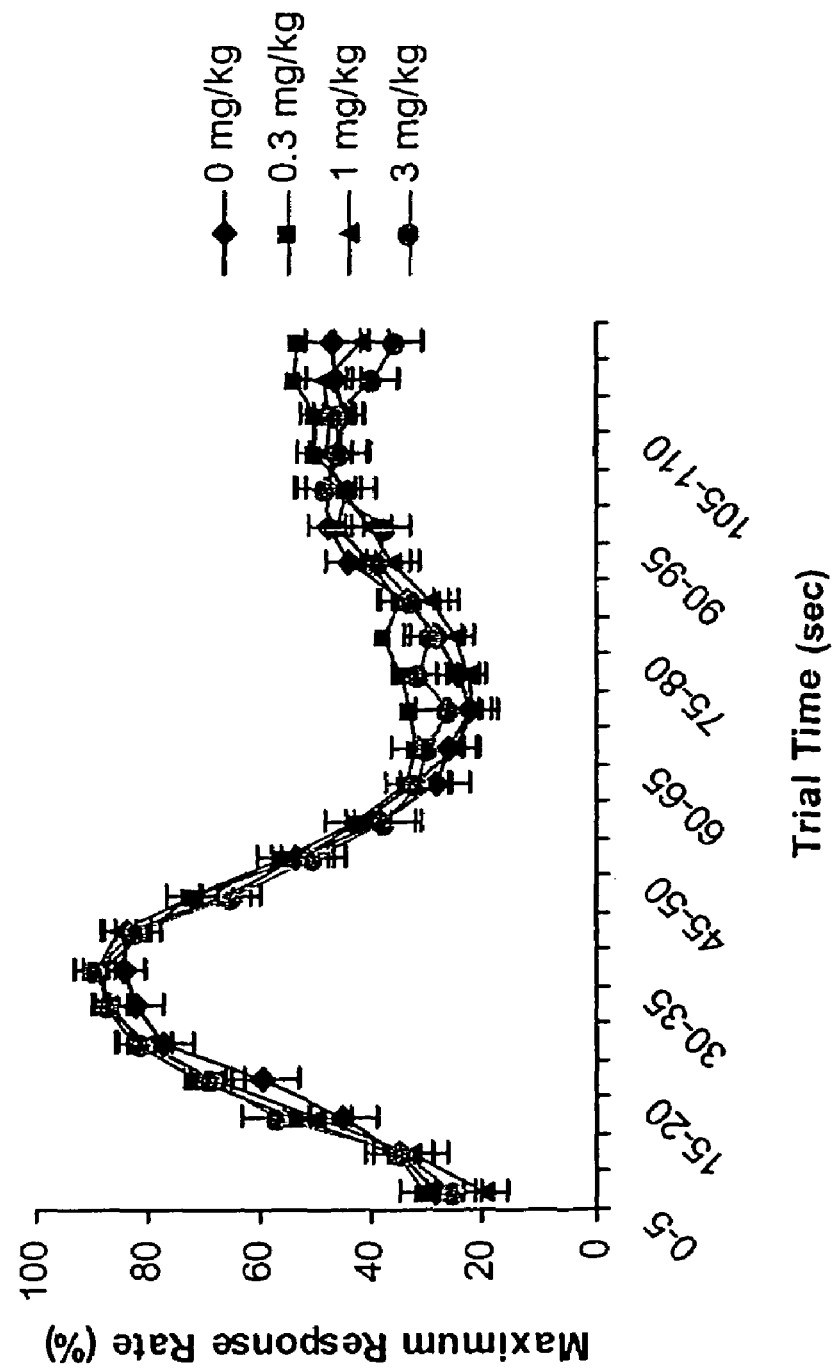
FIG. 8-Graph depicts the effect of 5-$HT_{1B}$ receptor agonist CP 94253, 0.3, 1 or 3 mg/kg, i.p., on response rate of C3H mice in Peak Procedure (30 second reinforcement interval).

Another surprising discovery further indicates that the effects of eltoprazine in alleviating or normalizing ADHD-associated behaviors such as inattentiveness may be mediated by mechanisms other than agonist action at $5\text{-HT}_{1B}$ receptors. $5\text{-HT}_{1B}$ receptor agonists were found not to produce the same effects as eltoprazine on the Peak Procedure. The $5\text{-HT}_{1B}$ receptor agonist, CP 94253, was tested in C3H mice in the peak procedure using the methods described in Example 1. At doses between 0.3 to 3.0 mg/kg, CP 94253 had no effect on timing in the peak procedure in C3H mice, as depicted in FIG. 8. This contrasts with the effects of both eltoprazine and amphetamine in this paradigm (see Examples 1 and 2). These results provide further evidence that eltoprazine's therapeutic anti-ADHD effect of cognitive enhancement occurs by a mechanism other than its known $5\text{-HT}_{1B}$ agonist activity.

EXAMPLE 7

To further determine whether or not $5\text{-HT}_{1B}$ receptors play a role in the effectiveness of eltoprazine as an anti-ADHD therapeutic, mice in which the $5\text{-HT}_{1B}$ receptor was deleted by genetic knock out (Saudou et al., Science, 265:1875-1878, 1994) were tested on a delay of reinforcement behavioral paradigm, a differential reinforcement of low rate-36 second schedule (DRL-36s). Homozygous $5\text{-HT}_{1B}$ (1BKO) mice exhibit difficulty waiting for a specified time period to obtain a reward (Brunner and Hen, supra). This difficulty provides a useful model for assessing the ability of a drug to alter animal behavior which may reflect the hyperactivity-impulsivity symptoms of ADHD.

The hyperactivity-impulsivity of 1BKO mice was evaluated by comparing their behavior on a DRL-36s schedule with that of wild-type litter mates and homozygous 5-HT$_{1A}$ knockout (1AKO) mice. In contrast to 1BKO mice, 1AKO mice are hypoactive in the open field (Ramboz et al., Proc. Nat'l Acad. Sci., USA, 95:14476-81, 1998). 1AKO mice have been shown to display opposite behavioral phenotypes compared to 1BKO mice (Zhuang et al., Neuropsychopharmacology 21:52-60, 1999).

DRL schedules were originally developed and are used to screen putative antidepressant drugs (O'Donnell and Seiden, J. Pharmacol. Exp. Ther., 224:80-88, 1983; Seiden et al., Psychopharmacology (Berl), 86:55-60, 1985). Based on the ability to assess an animal's time perception capacity and ability to obtain an award for learning to wait for a specific time interval, measurements of DRL performance may be used to measure hyperactivity-impulsivity associated with ADHD (Monterosso and Ainslie, Psychopharmacology, 146:339-47, 1999).

Animals

Male homozygote 5-HT$_{1A}$ and 5-HT$_{1B}$ receptor knockout and wild type mice were bred within the laboratory animal facilities of the Utrecht University (GDL, Utrecht, The Netherlands). The breeding founders were originally obtained from Dr. R. Hen (Columbia University, New York) and were derived from established colonies from the 129/Sv strain (Saudou et al., supra; Ramboz et al., supra). Mice were generated by breeding homozygote knockout and wild type mice with the same 129/Sv genetic background. Food consumption was restricted to keep the animals on approximately 85% of their free-feeding weight.

Behavioral Testing

Experiments were conducted in eight identical mouse operant chambers (16×14×13 cm) with stainless steel grid floors (ENV-307M; Med Associates Inc., Georgia, Vt., USA) housed in sound-insulating and ventilated cubicles. Each chamber was equipped with two ultra-sensitive retractable levers, one on each side of a food cup containing photocells to register nose poke behavior and in which a pellet dispenser delivered 20 mg food pellets (Formula A/I, P.J. Noyes Company Inc., Lancaster, N.H., USA). A red house light (50 lux) was located in the center of the wall opposite to the food cup and levers. Stimulus lights were located above each lever and above the food cup. Experimental sessions were controlled and data were recorded by a computer.

The operant conditioning procedures used were a modification of those described by De Bruin et al. for rats (De Bruin et al., Prog. Brain Res. 126:103-113, 2000), which is incorporated herein by reference. Three phases of conditioning were conducted: autoshaping, acquisition and reversal learning, and extinction. In autoshaping procedure, animals (n=8 per genotype) learned to lever-press for food under a fixed-ratio 1 (FR1) schedule of reinforcement on both the left and right lever. At the beginning of each trial, a stimulus light was illuminated on either the right or left, and the corresponding lever was inserted into the chamber. Pressing the lever below the stimulus light resulted in the immediate delivery of a reinforcer signaled by the illumination of the stimulus light above the food cup, after which the stimulus light above the lever was extinguished and the lever retracted. Alternatively, when the lever was not pressed, after 60 sec the stimulus light was extinguished and the lever retracted, without the delivery of a food pellet. In either case, after a nose poke response into the food cup or a 30 sec time out period, a new trial started with an inter-trial interval ranging from 5 to 25 sec (mean 15 sec). Criterion was reached when animals earned in total 15 reinforcements during autoshaping sessions.

In acquisition and reversal, two levers are introduced into the chamber without illuminating stimulus lights. A session consisted of 50 trials, and mice were subjected to discrimination learning, i.e. only one of two available levers was reinforced. When acquisition of discrimination learning was fully mastered (criterion: accuracy between 95 and 100% correct lever presses), the task demands were changed, in that the other lever was reinforced until criterion was reached. The extinction phase was identical to acquisition and reversal but there was no reinforcement.

Mice trained on DRL procedure first received operant conditioning. DRL-36s task was adapted from procedures used in rats (O'Donnell and Seiden, supra). Briefly, mice first learned to respond for food under a DRL 6 sec schedule, which means that mice had to wait at least 6 seconds between successive lever presses in order to obtain a food reward. Subsequently the schedule requirement was increased every session in steps of 6 sec to 36 sec (DRL 36 sec). Each session started with the illumination of the house light, the stimulus light above the food cup and the presentation of the left lever for the duration of the session. Pressing the lever resulted in delivery of a food pellet when the inter-response time was longer than the required DRL time. If the mouse presses too soon, no reinforcement is given, the clock is reset to zero, and a new 36-sec waiting period starts. In this way, the DRL-36s schedule task primarily measures waiting strategies which reflect hyperactivity-impulsivity behaviors associated with ADHD. Animals were trained until performances on the DRL 36 sec schedule had stabilized (approximately 25 sessions). All training sessions lasted 60 min and were conducted 5 days per week from Monday-Friday. The total number of lever presses (responses), the total number of reinforcements, and the inter-response times (IRT) are recorded.

Data were analyzed as described elsewhere (Richards et al., J. Exp. Anal. Behav. 60:361-385, 1993; Sabol et al., Psychopharmacology 121:57-65, 1995). The inter-response time (IRT) analysis included three measures for the characterization of DRL 36 sec IRT distributions: peak area, peak location and burst ratio. Only peak area (PkA) and peak location (PkL) are presented. The PkA measure is the area of the obtained IRT distribution of a mouse above the corresponding negative exponential, a computation based on mean of obtained IRT durations excluding the burst component of IRT<3 sec (see Richards et al., supra, for details). The largest possible PkA value (1.0) only occurs if all the obtained IRT distributions had exactly the same value, whereas the smallest PkA value (0) indicates that the obtained IRT distributions and corresponding negative exponential are identical. Thus, decreases in PkA indicate that the mouse's IRT distribution becomes more similar to random performance indicating loss of schedule control. PkL is calculated as the median of the area of the obtained IRT distribution above the corresponding negative exponential.

Results

The autoshaping behavior of the operant conditioning procedure for wild type, 1BKO and 1AKO mice is depicted in FIG. 9. The time needed to reach criterion (FIG. 9A) was different between genotypes (ANOVA $F(2,24)=13.45$, $p<0.001$). Further analyses revealed that both 1AKO and 1BKO mice were faster in acquiring the autoshaping procedure. In addition, the mean number of nose pokes per minute, a putative measure of activity, was different between genotypes (ANOVA, F(2,24)=12.14, p<0.001), with 1BKO making the most nose pokes per minute (FIG. 9B). A non-parametric correlation (Kendall's τ) indicated that nose poke behavior and time needed to reach criterion were negatively correlated in all genotypes (r=−0.88, p<0.001). The increased nose poke responding in 1BKO mice reflects an autoshaped conditioned response and may be a form of impulsive responding (Tomie et al., Psychopharmacology, 139:376-382, 1998). Nose poke activity was not significantly increased in 1AKO mice during autoshaping phase.

Figure 10:
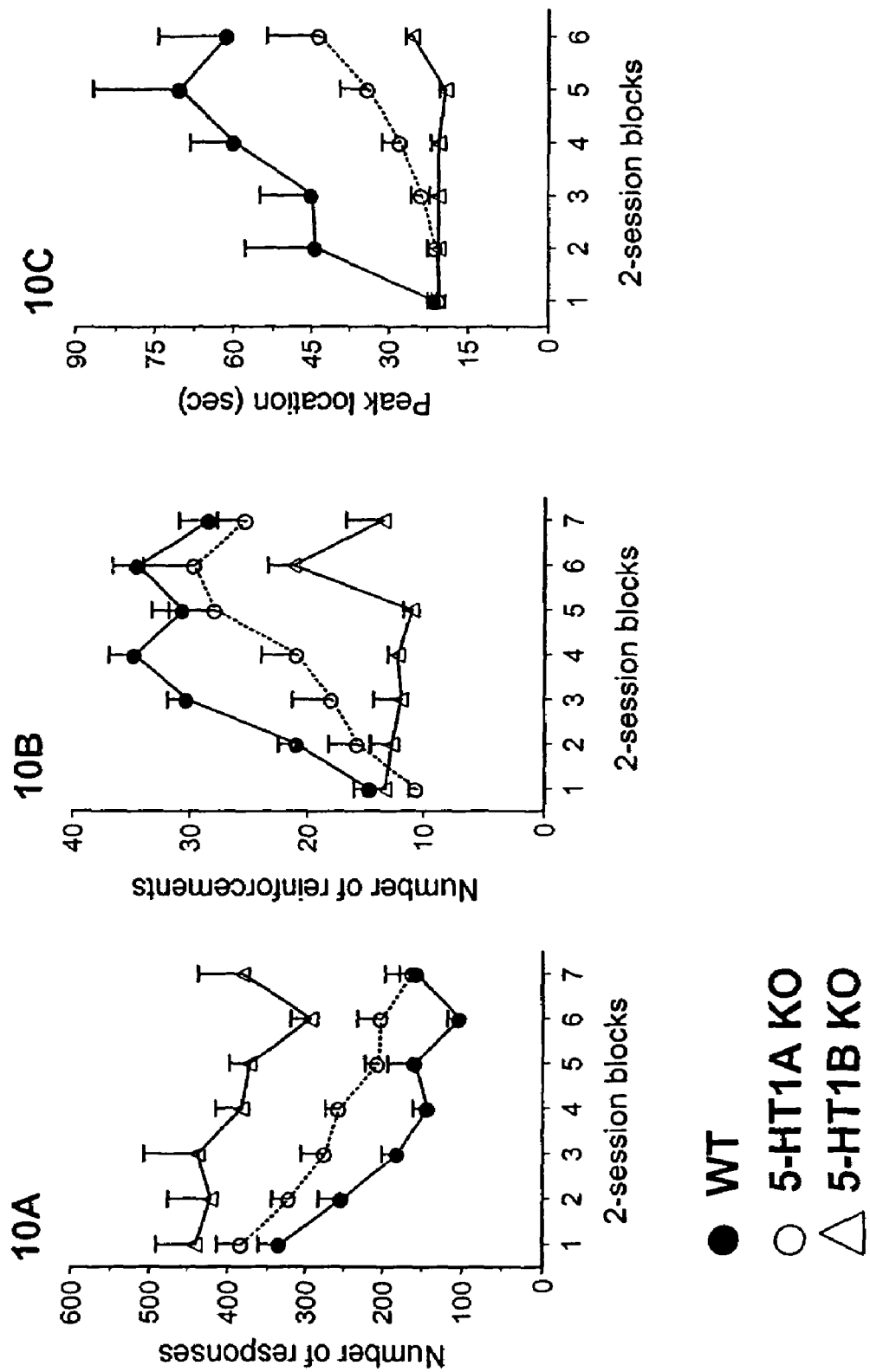
FIGS. 10 A-C—Graphs depict acquisition of a differential reinforcement of low rates-36 second (DRL-36s) schedule by 5-$HT_{1B}$ receptor knockout mice compared to wild-type mice; 10A: comparison of the number of responses made over the course of training session; 10B: comparison of the number of reinforcements received over course of training session; 10C: comparison of peak wait time to respond over course of training session.

FIG. 10 shows the difficulty the 1BKO mice have, in contrast to wild-type or 1AKO, learning the DL-36s schedule. The 1BKO mice exhibited severe time discrimination problems. The 1BKO mice consistently had a higher response rate, as depicted in FIG. 10A, and a lower reinforcement rate, as depicted in FIG. 10B, over the course of the first fourteen session compared to wild-type or 1AKO mice, indicating poor acquisition of the task. By contrast, wild-type and 1AKO mice progressively responded less frequently, as they learned the DRL 36s, waiting the appropriate interval in order to receive reinforcement. As a consequence, the wild-type and 1AKO mice received more reinforcements over the course of training. FIG. 10A shows that response rates decreased in all genotypes (F(6,114)=15.70, p<0.001), however the block× genotype interaction effect was not significant (F(12,114)=1.50, p=0.14). Moreover, there was a significant difference in response rates between genotypes (F(2,19)=20.15, p<0.001). Post hoc comparisons indicated that all genotypes differed, with 1BKO mice having the highest response rates and WT having the lowest response rates. The number of reinforcements were significantly increased for wild-type and 1AKO, but not for 1BKO mice (F(6,114)=16.48, p<0.001; block×genotype interaction effect, F(12,114)=4.06, p<0.001). Response rate of all genotypes differed significantly from one another (F(2,19)=22.06, p<0.001).

FIG. 10C shows that 1BKO mice did not lengthen their wait time to respond until towards the end of training, unlike the wild-type and 1AKO mice. Peak deviation analysis showed that PkL increased over blocks in all mice (F(6,114)=2.73, p<0.05), but there was a significant genotype difference (F(2,19)=17.12, p<0.001); there was no significant block×genotype interaction effect (F(12,114)=1.46, p=0.15).

Figure 11:
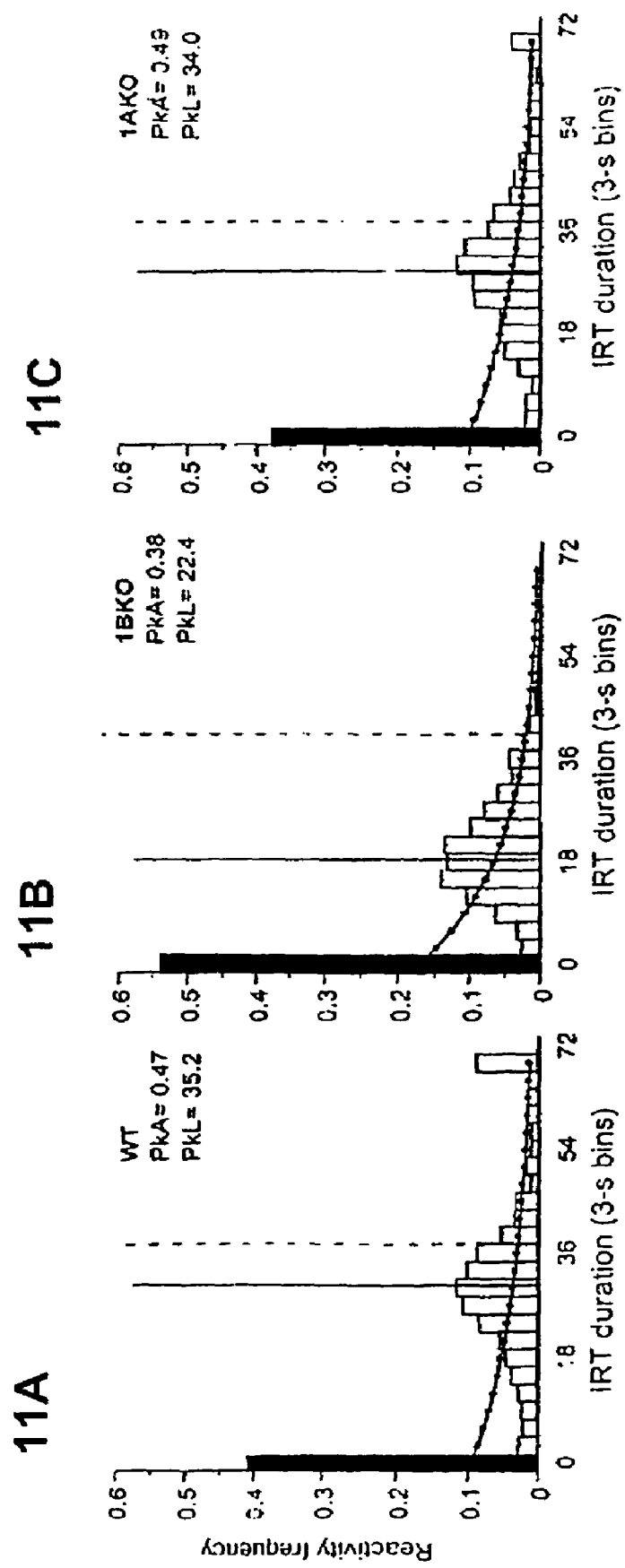
FIGS. 11 A-C—Graphs depict the inter-response time (IRT) histograms of performance under stable DRL-36 sec responding in WT (11A), 1AKO (11B) and 1BKO mice (11C). Frequency, as decimal fraction of whole, is plotted against IRT, in 3 second bins, with 36 seconds marked as the target for reinforcement. The bimodal IRT distribution of the DRL-36 sec is depicted, with one mode at short IRT durations (IRT<3 sec, grey bar on left) indicating bursting and a second mode at longer IRT durations indicating pausing (IRT>3 sec, white bars). The connected dots indicate the corresponding negative exponential which depicts random performance. Peak location (PkL or the "median" of the curve) was 35.2, 22.4, and 34 sec. for wild-type, 1BKO, and 1AKO mice, respectively.

Once the DRL performance had stabilized, the response rate of 1BKO mice remained significantly higher and the reinforcement rate lower than wild-type or 1AKO mice. The IRT histograms of stable DRL performance of wild-type, 1BKO, and 1AKO mice are shown in FIGS. 11A, 11B, and 11C, respectively. FIG. 11 demonstrates that the PkL remained much shorter (22.4 sec) than wild-type (35.2 sec) or 1AKO mice (34.0 sec). In summary, a mouse (like the 1BKO) showing a disruptive DRL-strategy is a useful model for assessing the ability of a drug to alter animal behavior which may reflect the hyperactivity-impulsivity symptoms of ADHD. Thus, the DRL-36s schedule can be used to measure anti-impulsive effects of psychotropic agents on 1BKO mice. The behavior of 1BKO mice in the DRL-36s paradigm is in general agreement with the type of behaviors observed in ADHD children, indicating 1BKO mice are a useful animal model of ADHD.

EXAMPLE 8

Since impulsivity with hyperactivity are behaviors associated with ADHD, 1BKO mice were further tested on a DRL-36s schedule to evaluate the potential therapeutic effect of eltoprazine. The effects of eltoprazine and d-amphetamine on the performance of 1BKO and wild-type mice on DRL-36s schedule were compared to determine whether these drugs influenced the behavior of 1BKO and wild-type mice in the same manner.

Behavioral Testing

Mice were conditioned and challenged on a DRL-36s schedule according to the methods of Example 7, with the following modifications. Because 1BKO mice had difficulty learning the DRL-36s schedule following conditioning on an FR1, wild-type and 1BKO mice were conditioned on a fixed rate 5 (FR5) schedule. In FR5, instead of pressing the lever once for a reward, animals have to press 5 times. The rationale for changing the operant conditioning was that by increasing the number of responses necessary for reinforcement, the wild-type mice should have greater difficulty and the 1BKO (which have higher response rates anyway) should have less difficulty getting reinforcements. In fact, we found that following FR5 conditioning, wild-type and 1BKO mice did not differ dramatically in their DRL-36s performance.

Figure 12:
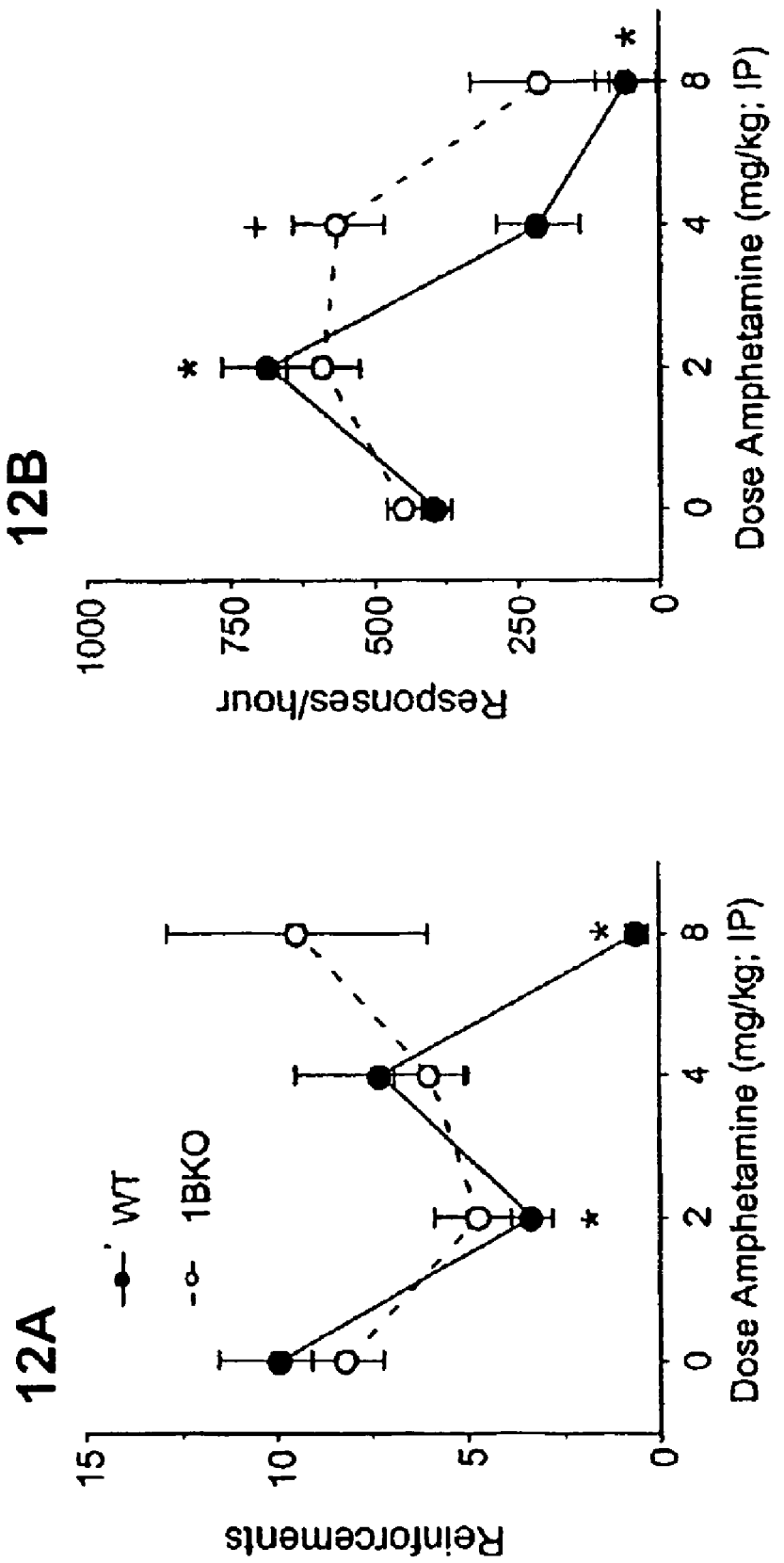
FIGS. 12 A-B—Graphs depict the effect of d-amphetamine (2, 4 or 8 mg/kg, i.p.) on 12A: the number of reinforcements and 12B: the response rate of wild-type (WT) and 5-$HT_{1B}$ knockout (1BKO) mice trained on a fixed-rate 5 (FR5) DRL-36s schedule. * p<0.05 compared to vehicle; +p<0.05 WT vs. 1BKO.

Results d-Amphetamine, at 2 and 8 mg/kg, significantly decreased the number of reinforcements in wild-type mice but had no significant effect on number of reinforcements in 1BKO mice, as depicted in FIG. 12. ANOVA revealed a significant dose main effect (F(3,92)=3.53, p<0.05) and a significant dose×genotype interaction (F(3,92)=4.44, p<0.01), but genotype main effect was not significant. The effect of amphetamine on response rates in 1BKO mice was not statistically significant at any dose, but amphetamine significantly increased response rate in wild-types at 2 mg/kg and decreased response rate in wild-types at 8 mg/kg. At 4 mg/kg, amphetamine significantly decreased response rate in wild-types compared to 1BKO mice. ANOVA revealed significant dose main effect (F(3,92)=17.0, p<0.001), dose×genotype interaction (F(3,92)=3.48, p<0.05), and genotype main effect (F(1,92)=5.26, p<0.05). The increased response rate and decreased reinforcement rate at the lowest dose of amphetamine is indicative of disruption of the behavior.

By contrast, eltoprazine had comparable effects on the behavior of wild-type and 1BKO mice in the DRL-36s task, as depicted in FIG. 13. Eltoprazine significantly decreased reinforcements equivalently in wild-type and 1BKO mice at 0.5 mg/kg and 1 mg/kg, and significantly decreased response rates equivalently in wild-type and 1BKO mice at 0.5 mg/kg in the DRL-36s schedule. ANOVA revealed a significant dose main effect for reinforcements (F(3,57)=8.57, p<0.001) and response rates (F(3,92)=5.59, p<0.001), but no significant genotype main effect or dose×genotype interaction for either reinforcements or response rates. A comparison of FIGS. 12 and 13 demonstrate that eltoprazine exhibits amphetamine-like properties in both genotypes.

To summarize, the wild-type and 1AKO mice learn to wait at least 36 seconds before responding and receive a greater number of reinforcements. By contrast, the 1BKO knockout mice respond too early and their behavior does not improve very much over successive trials, indicative of their hyperactive-impulsive tendency and the lack of involvement of 5-HT$_{1B}$ receptors. Eltoprazine shares some of the properties of d-amphetamine in its effects on DRL-36s behavior. Similarities are particularly notable in the number of reinforcements, where genotype-independent decreases are present. The eltoprazine profile is different from d-Amphetamine, however, perhaps reflecting an anti-ADHD profile distinct from psychostimulants.

EXAMPLE 9

To further determine what if any role 5-$HT_{1B}$ receptors play in the anti-ADHD effects of eltoprazine of this invention, in the context of DA and 5-HT interactions, DA and 5-HT release were examined in eltoprazine treated mice using in vivo microdialysis. Eltoprazine-induced changes in basal DA and 5-HT release were then compared with the effects of a specific 5-$HT_{1B}$ receptor agonist CP 93129. In vivo microdialysis permits measurement of extracellular neurotransmitter concentrations in awake, freely moving animals.

In Vivo Microdialysis and HPLC-ECD Analysis

Wild-type and 5-$HT_{1B}$ knock out mice were implanted with microdialysis probes according to the methods of DeGroote et al., incorporated herein by reference, with the following modifications. (DeGroote et al., Eur. J. Pharmacol., 439:93-100, 2002). The dialysis probe was placed in the dorsal striatum, at coordinates AP +0.80, ML −1.7 mm from bregma, DV −4.0 mm from the dura, according to the stereotaxic atlas of the mouse brain (Franklin and Paxinos, 1997), and with the toothbar set at 0 mm. Microdialysis experiments were begun 16-20 hours after surgery, using previously described methods, which are incorporated herein by reference (DeGroote et al., 2002). After the start of the dialysis probe perfusion, mice were left undisturbed for three hours. Mice were tested in their home cage during the light period. Samples were collected every 20 minutes in vials containing 7.5 μl acetic acid and stored at −80° C. until HPLC analysis.

Release of DA and 5-HT was measured after peripheral administration of eltoprazine or intrastriatal administration of the selective 5-$HT_{1B}$ receptor agonist CP 93129 dihydrochloride (1,4-Dihydro-3-(1,2,3,6-tetrahydro-4-pyridinyl)-5H-pyrrolo[3,2-b]pyridin-5-one, obtained from Tocris, UK.) Drugs were dissolved in distilled water and further diluted in Ringer solution to the final concentration on the day of the experiment. 5-HT and DA were analyzed by HPLC with electrochemical detection. Samples (25 μl) were injected onto an Inertsil ODS-3 column (3 μM, 2.1×100 mm, Aurora Borealis, The Netherlands) using a Gilson pump and autosampler (Separations, The Netherlands). Separation was performed at 40° C. with the electrochemical detector (Intro, ANTEC Leyden, The Netherlands) set at a potential of 600 mV against an Ag/AgCl reference electrode. The signal was analyzed using Gynkotek software. The mobile phase consisted of 5 g/l $(NH_4)_2SO_4$, 150 mg/l heptane sulphonic acid sodium salt, 0.5 g/l EDTA, 5% methanol, 30 μl/l triethylamine, 30 μl/l acetic acid, pH 4.6. Flow rate was 0.3 ml/min. The detection limit for 5-HT was 0.5 fmol/25 μl sample (signal to noise ratio 2).

Values for the first four consecutive microdialysis samples were averaged to calculate the basal levels of extracellular 5-HT and DA, uncorrected for probe recovery. Student's t-tests were used to compare basal 5-HT and DA values between the two genotypes. Effects of drug treatment were analyzed by a repeated multivariate analysis of variance (ANOVA) with time as 'within' and treatment (or dose) and genotype as 'between' factors.

Results

Basal levels of extracellular 5-HT and DA levels in the dorsal striatum were not different between wild-type and 1BKO mutants. Basal 5-HT levels were 4.0±0.3 fmol/sample in wild-type and 5.0±0.6 fmol/sample in 1BKO mice. Basal DA levels were 181.3±14.6 fmol/sample in wild-type and 183.1±15.9 fmol/sample in 1BKO mice.

Eltoprazine effects on DA and 5-HT release were similar and independent of genotype. Eltoprazine (0.1 mg/kg, i.p.) decreased basal release of both DA and 5-HT release in dorsal striatum of awake wild-type mice within 20 minutes after administration, as depicted in FIG. 13. In these animals, striatal release of DA and 5-HT remained below basal levels for at least 100 minutes after drug administration.

Figure 14:
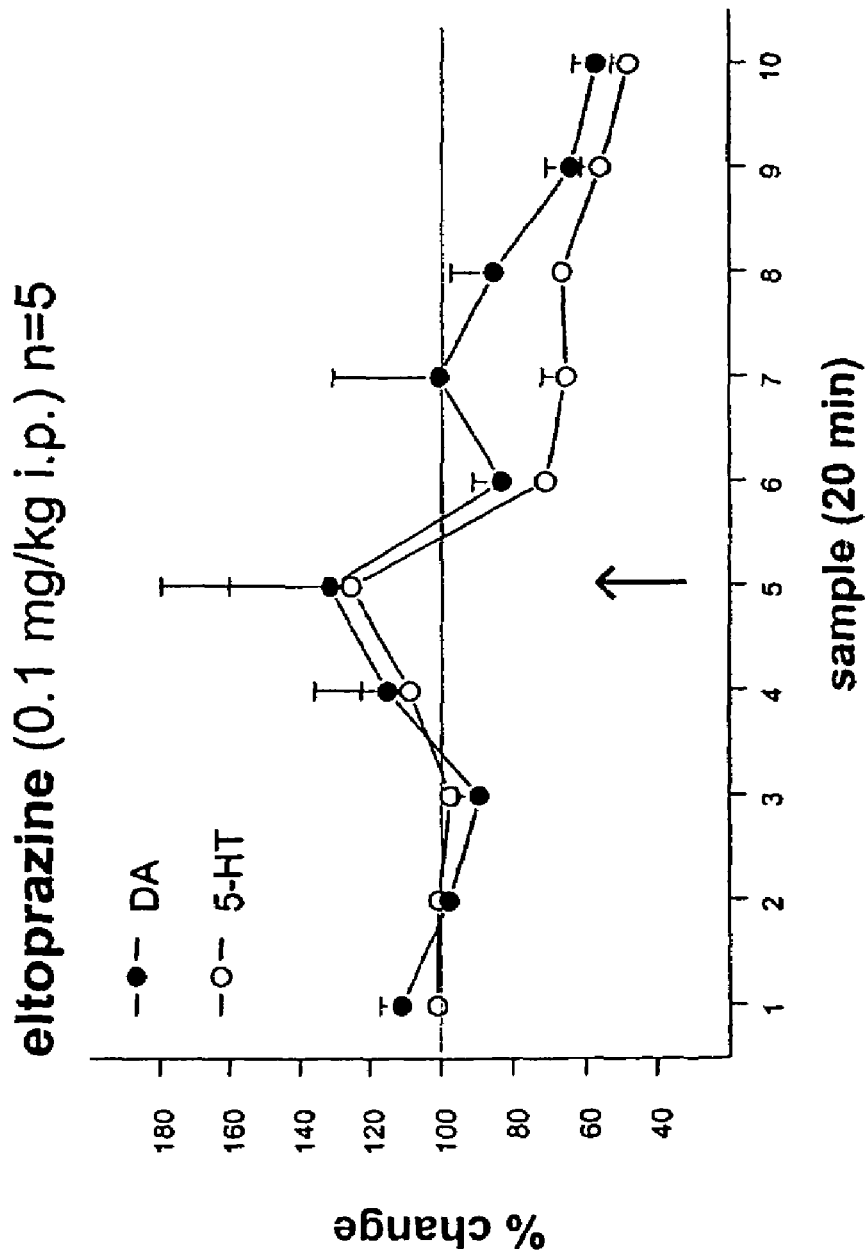
FIG. 14—Graph depicts the effect of eltoprazine (0.1 mg/kg, i.p.) on percent change in basal DA and 5-HT outflow in dorsal striatum of awake, freely moving wild-type mice. DA and 5-HT release was measured by in vivo microdialysis coupled to HPLC-ECD. DA or 5-HT levels are expressed as percentages of basal levels±SEM. Dialysate was sampled every 20 minutes; time of drug administration is indicated by the arrow.
Figure 15:
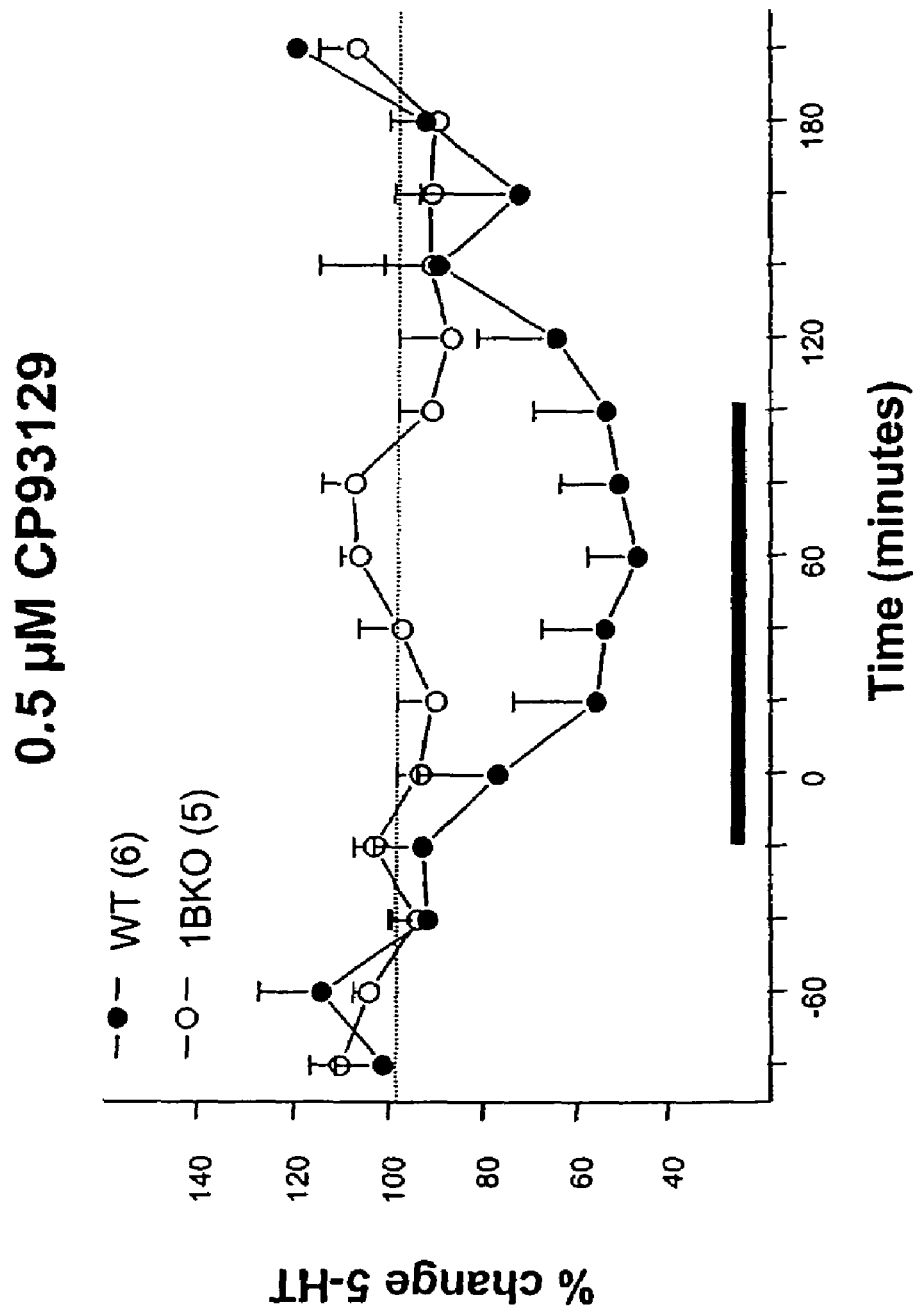
FIG. 15—Graph depicts the effect of local administration of the 5-$HT_{1B}$ receptor agonist CP 93129 (0.5 µM) on percent change in basal 5-HT outflow in dorsal striatum of awake, freely moving wild-type and 5-$HT_{1B}$ knockout (1BKO) mice. 5-HT release was measured by in vivo microdialysis coupled to HPLC-ECD. Dialysate was sampled every 20 minutes; time of drug introduction through microdialysis probe is indicated by the solid black bar.
Figure 16:
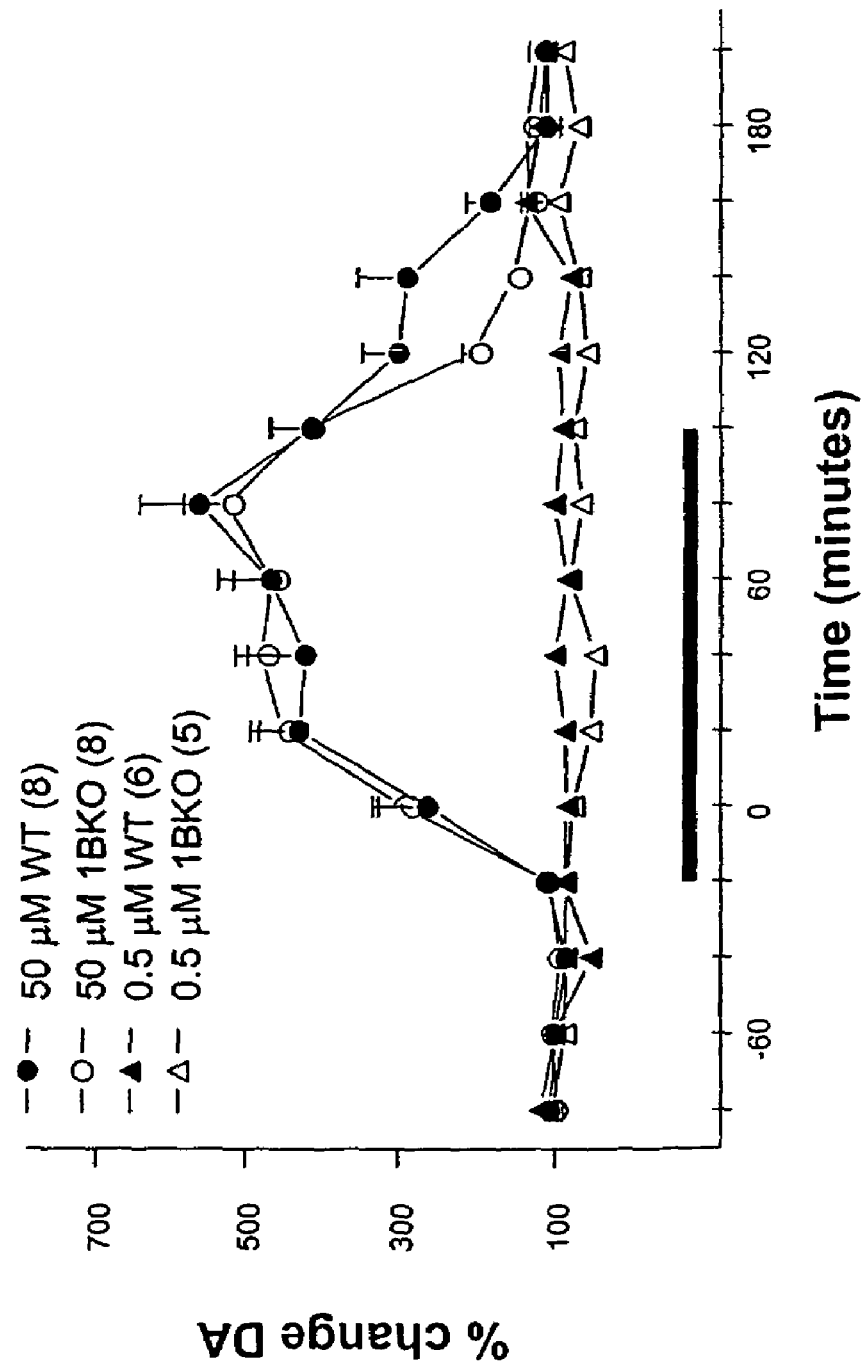
FIG. 16—Graph depicts the effect of local administration of the 5-$HT_{1B}$ receptor agonist CP 93129 (0.5 or 50 µM) on percent change in basal DA outflow in dorsal striatum of awake, freely moving wild-type and 5-$HT_{1B}$ knockout (1BKO) mice. DA release was measured by in vivo microdialysis coupled to HPLC-ECD. Dialysate was sampled every 20 minutes; time of drug introduction through microdialysis probe is indicated by the solid black bar.

In contrast to eltoprazine, CP 93129 had differing effects on 5-HT and DA release that were genotype specific at low dose. Local administration of CP 93129 (0.5 μm) decreased striatal 5-HT release in wild-type mice (FIG. 14), an effect similar to that observed with eltoprazine. Repeated measures ANOVA revealed a dose main effect (F(1,17)=6.2, p<0.05) and genotype main effect (F(1,17)=13.5, p<0.01). In wild-type mice, CP93129 (0.5 μM) reduced 5-HT to 51±9% as compared to vehicle (F(1,10)=11.2, p<0.01). 5-HT release returned toward basal levels within 40 minutes after cessation of CP 93129. In contrast to eltoprazine, however, DA release was unaffected by 0.5 μM CP 93129 (FIG. 15). The CP 93129 attenuation of basal 5-HT release was mediated through the 5-$HT_{1B}$ receptor. As FIG. 14 illustrates CP 93129 did not decrease 5-HT release in mice lacking the 5-$HT_{1B}$ receptor (i.e., 1BKO).

Striatal release of DA in 1BKO mice was similarly unaffected by CP 93129 (FIG. 15). As FIG. 15 further shows, a very high concentration of CP 93129 (50 μM) increased DA release in striatum of wild-type mice. This CP 93129-induced stimulation of DA release was independent of 5-$HT_{1B}$ receptor activation, since a comparable increase in DA release was observed in 1BKO mice. A repeated measures ANOVA of the CP 93129 data revealed dose main effect for (F(2,32)=55.6, p<0.001) and a time×dose interaction effect (F(16, 256)=7.9, p<0.001), but not a genotype main effect (F(2,32)=0.5, p=0.98). The high dose of CP 93129 increased DA levels in 1BKO mice to the same extent as in wild-types when compared to vehicle (p<0.001). These CP 93129-induced increases were 525±79% and 527±67% in wild-type and 1BKO, respectively.

In summary, because eltoprazine affects both 5-HT and DA release, it is presumed that its mechanism of action in alleviating behaviors associated with ADHD is different from its 5-$HT_{1B}$ agonist properties. Moreover, while both eltoprazine and the psychostimulant anti-ADHD agent amphetamine attenuate ADHD-associated behaviors, inattentiveness, and hyperactivity with impulsivity, the mechanism of action of eltoprazine may be differentiated from that of amphetamine. Eltoprazine was observed to decrease striatal DA release, whereas amphetamine is well known to increase extracellular striatal DA levels (see Hess et al., 1996, supra).

The above Examples are for illustrative purposes only and are not intended to limit the scope of the invention.

We claim:

1. A method of treating attention-deficit/hyperactivity disorder (ADHD) in humans comprising administering to humans in need thereof a therapeutically effective amount of a compound according to the formula

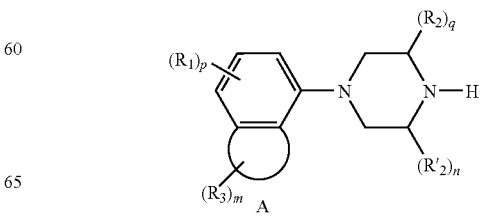

wherein
R₁ is hydrogen, alkyl, cycloalkyl, optionally esterified hydroxyalkyl, alkoxyalkyl, optionally substituted phenyl or heteroaryl, alkoxy, aryloxy, alkylthio, arylthio, alkoxycarbonyl, aminocarbonyl, alkyl- or dialkyl-aminocarbonyl, nitro, amino, alkyl- or dialkyl-amino, alkylsulfonylamino, arylamino, cyano, halogen, trifluoromethyl, trifluoromethoxy, optionally esterified hydroxyl, alkyl- or amino-sulphonyl or -sulphinyl, alkyl- or dialkyl-aminosulphonyl or -sulphinyl, and p has the value 0-3;

R₂ and R'₂ are independently hydrogen or an alkyl group and n and q can have the value 0 or 1;

R₃ is hydrogen, and m has the value 0-2;

A forms, with the two carbon atoms of the phenyl group, an optionally entirely or partly unsaturated cyclic group having 6 atoms in the ring, which comprises 2 or 3 hetero atoms selected from the group consisting of O, S, and N, with the proviso that the sum of the number of oxygen and sulphur atoms is at most 2;

wherein
the compound may be a racemate or a single diastereomer or enantiomer;
or a pharmaceutically acceptable acid addition salt thereof.

2. The method according to claim 1, wherein the compound is administered to either an adult or an adolescent.

3. The method according to claim 1, wherein the compound is administered to an adult.

4. The method according to claim 1, wherein the compound is administered to an adolescent.

5. The method according to claim 1, wherein R₁, R₂ and R'₂ are hydrogen.

6. The method according to claim 1, wherein the compound is administered at a dose of about 0.1 mg/day to 100 mg/day.

7. The method according to claim 1, wherein the compound is administered at a dose of about 0.1 mg/day to 30 mg/day.

8. The method according to claim 1, wherein the compound is administered at a dose of about 0.1 mg/day to 10 mg/day.

9. The method according to claim 1, wherein the compound is administered to achieve a plasma concentration in a human of between 0.06 nglml and 200 ng/ml.

10. The method according to claim 9, wherein the compound is administered to achieve a plasma concentration in a human of between 0.2 nglml and 65 ng/ml.

11. A method of treating ADHD of the hyperactive/impulsive type in humans comprising administering to humans in need thereof a therapeutically effective amount of a compound according to the formula

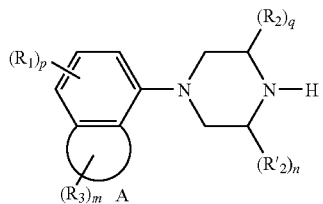

wherein R₁ is hydrogen, alkyl, cycloalkyl, optionally esterified hydroxyalkyl, alkoxyalkyl, optionally substituted phenyl or heteroaryl, alkoxy, aryloxy, alkylthio, arylthio, alkoxycarbonyl, aminocarbonyl, alkyl- or dialkyl-aminocarbonyl, nitro, amino, alkyl- or dialkyl-amino, alkylsulfonylamino, arylamino, cyano, halogen, trifluoromethyl, trifluoromethoxy, optionally esterified hydroxyl, alkyl- or amino-sulphonyl or sulphinyl, alkyl- or dialkyl-aminosuiphonyl or -sulphinyl, and p has the value 0-3; R₂ and R'₂ are independently hydrogen or an alkyl group and n and q have the value 0 or 1; R₃ is hydrogen, and m has the value 0-2; A forms, with the two carbon atoms of the phenyl group, an optionally entirely or partly unsaturated cyclic group having 6 atoms in the ring, which comprises 2 or 3 hetero atoms selected from the group consisting of O, S, and N, with the proviso that the sum of the number of oxygen and sulphur atoms is at most 2;

wherein
the compound may be a racemate or a single diastereomer or enantiomer; or a pharmaceutically acceptable acid or salt thereof.

12. The method according to claim 11, wherein the compound is administered at a dose of about 0.1 mg/day to 100 mg/day.

13. The method according to claim 11, wherein the compound is administered at a dose of about 0.1 mg/day to 30 mg/day.

14. The method according to claim 11, wherein the compound is administered at a dose of about 0.1 mg/day to 10 mg/day.

15. The method according to claim 11, wherein the compound is administered to achieve a plasma concentration in a human of between 0.06 ng/ml and 200 ng/ml.

16. The method according to claim 15, wherein the compound is administered to achieve a plasma concentration in a human of between 0.2 ng/ml and 65 ng/ml.

17. The method according to claim 11, wherein the compound is administered to either an adult or an adolescent.

18. The method according to claim 11, wherein the compound is administered to an adult.

19. The method according to claim 11, wherein the compound is administered to an adolescent.

20. A method of treating ADHD of the inattentive type in humans comprising administering to humans in need thereof a therapeutically effective amount of a compound according to the formula

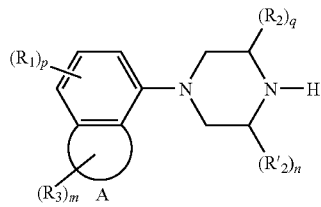

wherein R₁ is hydrogen, alkyl, cycloalkyl, optionally esterified hydroxyalkyl, alkoxyalkyl, optionally substituted phenyl or heteroaryl, alkoxy, aryloxy, alkylthio, arylthio, alkoxycarbonyl, aminocarbonyl, alkyl- or dialkyl-aminocarbonyl, nitro, amino, alkyl- or dialkyl-amino, alkylsulfonylamino, arylamino, cyano, halogen, trifluoromethyl, trifluoromethoxy, optionally esterified hydroxyl, alkyl- or aminosulphonyl or sulphinyl, alkyl- or dialkyl-aminosulphonyl or sulphinyl, and p has the value 0-3; R₂ and R'₂ are independently hydrogen or an alkyl group and n and q have the value 0 or 1; R₃ is hydrogen, and m has the value 0-2; A forms, with the two carbon atoms of the phenyl group, an optionally entirely or partly unsaturated cyclic group having 6 atoms in the ring, which comprises 2 or 3 hetero atoms selected from the group consisting of O, S, and N, with the proviso that the sum of the number of oxygen and sulphur atoms is at most 2;

wherein
the compound may be a racemate or a single diastereomer or enantiomer; or a pharmaceutically acceptable acid or salt thereof.

21. The method according to claim 20, wherein the compound is administered at a dose of about 0.1 mg/day to 100 mg/day.

22. The method according to claim 20, wherein the compound is administered at a dose of about 0.1 mg/day to 30 mg/day.

23. The method according to claim 20, wherein the compound is administered at a dose of about 0.1 mg/day to 10 mg/day.

24. The method according to claim 20, wherein the compound is administered to achieve a plasma concentration in a human of between 0.06 ng/ml and 200 ng/ml.

25. The method according to claim 24, wherein the compound is administered to achieve a plasma concentration in a human of between 0.2 ng/ml and 65 ng/ml.

26. The method according to 20, wherein the compound is administered to either an adult or an adolescent.

27. The method according to 20, wherein the compound is administered to an adult.

28. The method according to 20, wherein the compound is administered to an adolescent.

* * * * *

UNITED STATES PATENT AND TRADEMARK OFFICE
CERTIFICATE OF CORRECTION

PATENT NO. : 7,557,109 B2
APPLICATION NO. : 11/219416
DATED : July 7, 2009
INVENTOR(S) : Brunner et al.

It is certified that error appears in the above-identified patent and that said Letters Patent is hereby corrected as shown below:

Column 23, claim 1, line 24, please amend "acid addition salt" to --acid or salt--;

Column 23, claim 9, line 42, please amend "0.06 nglml" to --0.06 ng/ml--; and

Column 23, claim 10, line 45, please amend "0.2 nglml" to --0.2 ng/ml--.

Signed and Sealed this

Twenty-seventh Day of October, 2009

David J. Kappos
*Director of the United States Patent and Trademark Office*